US011697689B2

(12) United States Patent
Birkle et al.

(10) Patent No.: US 11,697,689 B2
(45) Date of Patent: Jul. 11, 2023

(54) USE OF ANTIBODY AGAINST O-ACETYLATED GD2 GANGLIOSIDE TO IMPROVE THE THERAPEUTIC POTENTIAL OF DRUGS

(71) Applicants: OGD2 PHARMA, Nantes (FR); NANTES UNIVERSITÉ, Nantes (FR); CENTRE NATIONAL DE LA RECHERCHE SCIENTIFIQUE (CNRS), Paris (FR); INSTITUT NATIONAL DE LA SANTE ET DE LA RECHERCHE MEDICALE (INSERM), Paris (FR); INSTITUT DE CANCEROLOGIE DE L'OUEST, Angers (FR)

(72) Inventors: Stéphane Birkle, Nantes (FR); Julien Fleurence, Nantes (FR); Sébastien Faraj, Nantes (FR); Jean-Marc Le Doussal, Lausanne (CH); Denis Cochonneau, Coueron (FR); Mickaël Terme, Nantes (FR); Brigitte Assouline, Courbevoie (FR)

(73) Assignees: OGD2 PHARMA, Nantes (FR); NANTES UNIVERSITÉ, Nantes (FR); CENTRE NATIONAL DE LA RECHERCHE SCIENTIFIQUE (CNRS), Paris (FR); INSTITUT NATIONAL DE LA SANTE ET DE LA RECHERCHE MEDICALE (INSERM), Paris (FR); INSTITUT DE CANCEROLOGIE DE L'OUEST, Angers (FR)

( * ) Notice: Subject to any disclaimer, the term of this patent is extended or adjusted under 35 U.S.C. 154(b) by 649 days.

(21) Appl. No.: 16/466,769

(22) PCT Filed: Dec. 5, 2017

(86) PCT No.: PCT/EP2017/001406
§ 371 (c)(1),
(2) Date: Jun. 5, 2019

(87) PCT Pub. No.: WO2018/103884
PCT Pub. Date: Jun. 14, 2018

(65) Prior Publication Data
US 2019/0375853 A1 Dec. 12, 2019

(30) Foreign Application Priority Data
Dec. 5, 2016 (EP) .................................... 16002576

(51) Int. Cl.
*C07K 16/30* (2006.01)
(52) U.S. Cl.
CPC ...... *C07K 16/3084* (2013.01); *C07K 2317/24* (2013.01); *C07K 2317/565* (2013.01); *C07K 2317/622* (2013.01)

(58) Field of Classification Search
CPC ............ C07K 16/3084; C07K 2317/24; C07K 2317/565; C07K 2317/622; C07K 2317/73; A61P 35/00; A61P 35/02; A61P 35/04; A61K 2039/505; A61K 39/39558
See application file for complete search history.

(56) References Cited

U.S. PATENT DOCUMENTS

| 5,730,969 | A | 3/1998 | Hora et al. |
| 8,951,524 | B2 | 2/2015 | Birkle et al. |
| 2010/0150910 | A1 | 6/2010 | Birkle et al. |
| 2015/0140023 | A1 | 5/2015 | Birkle et al. |
| 2016/0068608 | A1* | 3/2016 | Birkle ..................... A61P 35/00 424/137.1 |
| 2016/0272722 | A1 | 9/2016 | Le Doussal et al. |
| 2017/0226183 | A1 | 8/2017 | Schiffer-Mannioui |

FOREIGN PATENT DOCUMENTS

| EP | 2076542 B1 | 8/2012 |
| FR | 2906808 A1 | 4/2008 |
| WO | 2014/177271 A1 | 11/2014 |
| WO | 2015/067375 A1 | 5/2015 |
| WO | 2016/016343 A1 | 2/2016 |

OTHER PUBLICATIONS

Mariuzza (Annu. Rev. Biophys. Biophys. Chem., 16: 139-159, 1987).*
Brent P. Mahoney et al., "Tumor acidity, ion trapping and chemotherapeutics. I. Acid pH affects the distribution of chemotherapeutic agents in vitro", Biochemical Pharmacology, Oct. 2003, vol. 66, No. 7, pp. 1207-1218 (12 pp.), doi: 10.1016/s0006-2952(03)00467-2.
Pedro Barata et al., "RNA-targeted therapeutics in cancer clinical trials: Current status and future directions", Cancer Treatment Reviews, Nov. 2016, vol. 50, pp. 35-47 (13 pp.), doi: 10.1016/j.ctrv.2016.08.004.
Ying-Zheng Zhao et al., "Phospholipids-based microbubbles sonoporation pore size and reseal of cell membrane cultured in vitro", Journal of Drug Targeting, Jan. 2008, vol. 16, No. 1, pp. 18-25 (8 pp.), doi: 10.1080/10611860701637792.
Masayuki Hiraki et al., "Concurrent Targeting of KRAS and AKT by MiR-4689 Is a Novel Treatment Against Mutant KRAS Colorectal Cancer", Molecular Therapy—Nucleic Acids, Mar. 10, 2015, vol. 4, No. 3, Article e231, pp. 1-13 (13 pp.), doi: 10.1038/mtna.2015.5.
Yingnan Sun et al., "MiR-429 inhibits cells growth and invasion and regulates EMT-related marker genes by targeting Onecut2 in colorectal carcinoma", Molecular and Cellular Biochemistry, May 2014, vol. 390, No. 1-2, pp. 19-30 (12 pp.), doi: 10.1007/s11010-013-1950-x.
E. Richard Cohen et al., "Quantities, Units and Symbols in Physical Chemistry", IUPAC Green Book, Third Edition, 2007, 250 pp.

(Continued)

*Primary Examiner* — Nelson B Moseley, II
(74) *Attorney, Agent, or Firm* — Nixon & Vanderhye

(57) ABSTRACT

Disclosed is a method for delivery of an anti-cancer agent into a cell expressing the OAcGD2 ganglioside by using an antibody recognizing the OAcGD2 ganglioside.

18 Claims, 8 Drawing Sheets

Specification includes a Sequence Listing.

(56) References Cited

OTHER PUBLICATIONS

Katherine K. Matthay et al., "Treatment of high-risk neuroblastoma with intensive chemotherapy, radiotherapy, autologous bone marrow transplantation, and 13-cis-retinoic acid. Children's Cancer Group", The New England Journal of Medicine, Oct. 14, 1999, vol. 341, No. 16, pp. 1165-1173 (9 pp.), doi: 10.1056/NEJM199910143411601.

Anroop B. Nair and Shery Jacob, "A simple practice guide for dose conversion between animals and human", Journal of Basic Clinical Pharmacology, Mar. 2016, vol. 7, No. 2, pp. 27-31 (5 pp.), doi: 10.4103/0976-0105.177703.

Angela Di Giannatale et al., "Phase II study of temozolomide in combination with topotecan (TOTEM) in relapsed on refractory neuroblastoma: a European Innovative Therapies for Children with Cancer-SIOP-European Neuroblastoma study", European Journal of Cancer, Jan. 2014, vol. 50, No. 1, pp. 170-177 (8 pp.), doi: 10.1016/j.ejca.2013.08.012.

Henry S. Friedman et al., "Bevacizumab alone and in combination with irinotecan in recurrent glioblastoma", Journal of Clinical Oncology, Oct. 1, 2009, vol. 27, No. 28, pp. 4733-4740 (8 pp.), doi: 10.1200/JCO.2008 19.8721.

Alice L. Yu et al., "Anti-GD2 antibody with GM-CSF, interleukin-2, and isotretinoin for neuroblastoma", The New England Journal of Medicine, Sep. 30, 2010, vol. 363, No. 14, pp. 1324-1334 (11 pp.), doi: 10.1056/NEJMoa0911123.

J. A. Kohler et al., "Treatment of children over the age of one year with unresectable localised neuroblastoma without MYCN amplification: results of the SIOPEN study", European Journal of Cancer, Nov. 2013, vol. 49, No. 17, pp. 3671-3679 (9 pp.), doi: 10.1016/j.ejca.2013.07.002.

L. K. Gilliland et al., "Rapid and reliable cloning of antibody variable regions and generation of recombinant single chain antibody fragments", Tissue Antigens, Jan. 1996, vol. 47, No. 1, pp. 1-20 (20 pp.), doi: 10.1111/i.1399-0039.1996.tb02509.x.

Temple F. Smith and Michael S. Waterman, "Comparison of biosequences", Advances in Applied Mathematics, Dec. 1981, vol. 2, No. 4, pp. 482-489 (8 pp.), https://doi.org/10.1016/0196-8858(81)90046-4.

Saul B. Needleman and Christian D. Wunsch, "A general method applicable to the search for similarities in the amino acid sequence of two proteins", Journal of Molecular Biology, Mar. 1970, vol. 48, No. 3, pp. 443-453 (11 pp.), doi: 10.1016/0022-2836(70)90057-4.

William R. Pearson and David J. Lipman, "Improved tools for biological sequence comparison", Proc. Natl. Acad. Sci. USA, Apr. 1988, vol. 85, No. 8, pp. 2444-2448 (5 pp.), doi: 10.1073/pnas.85.8.2444.

Robert C. Edgar, "Muscle: multiple sequence alignment with high accuracy and high throughput", Nucleic Acids Research, Mar. 19, 2004, vol. 32, No. 5, pp. 1792-1797 (6 pp.), doi: 10.1093/nar/gkh340.

Ulrich H Weidle et al., "The intriguing options of multispecific antibody formats for treatment of cancer", Cancer Genomics & Proteomics, Jan.-Feb. 2013, vol. 10, pp. 1-18 (18 pp.).

Ting-Chao Chou, "Theoretical basis, experimental design, and computerized simulation of synergism and antagonism in drug combination studies", Pharmacology Reviews, Sep. 2006, vol. 58, No. 3, pp. 621-681 (60 pp.), doi: 10.1124/pr.58.3.10.

Nidia Alvarez-Rueda et al., "A Monoclonal Antibody to O-Acetyl-GD2 Ganglioside and Not to GD2 Shows Potent Anti-Tumor Activity without Peripheral Nervous System Cross-Reactivity", PloS One, 2011, vol. 6, No. 9, pp. 1-12 (12 pp.), Article e25220, doi: 10.1371/journal.pone.0025220.

Michael Rebhan et al., "Altered ganglioside expression by SH-SY5Y cells upon retinoic acid-induced neuronal differentiation" Neuroreport, Apr. 14, 1994, vol. 5, No. 8, pp. 941-944 (4 pp.), doi: 10.1097/00001756-199404000-00022.

Evelyne Cerato et al., "Variable region gene segments of nine monoclonal antibodies specific to disialogangliosides (GD2, GD3) and their O-acetylated derivatives", Hybridoma, Aug. 1997, vol. 16, No. 4, pp. 307-316 (10 pp.), doi: 10.1089/hyb.1997.16.307.

Holger N. Lode et al., "Targeted interleukin-2 therapy for spontaneous neuroblastoma metastases to bone marrow", Journal of the National Cancer Institute, Nov. 5, 1997, vol. 89, No. 21, pp. 1586-1594 (9 pp.), doi: 10.1093/inci/89.21.1586.

Marie-Paule Lefranc et al., "IMGT, the international ImMunoGeneTics database", Nucleic Acids Research, Jan. 1, 1999, vol. 27, No. 1, pp. 209-212 (4 pp.), doi: 10.1093/nar/27.1.209.

Cyrus Chothia and Arthur M. Lesk, "Canonical structures for the hypervariable regions of immunoglobulins", Journal of Molecular Biology, Aug. 20, 1987, vol. 196, No. 4, pp. 901-917 (17 pp.), doi: 10.1016/0022-2836(87)90412-8.

Julien Fleurence et al., "Targeting and killing glioblastoma with monoclonal antibody to O-acetyl GD2 ganglioside", Oncotarget, Jul. 5, 2016, vol. 7, No. 27, pp. 41172-41185 (14 pp.), doi: 10.18632/oncotarget.9226.

S. Hettmer et al., "Alterations in neuroblastoma ganglioside synthesis by induction of GD1 b synthase by retinoic acid", British Journal of Cancer, Jul. 19, 2004, vol. 91, No. 2, pp. 389-397 (9 pp.), doi: 10.1038/sj.bjc.6601914.

International Search Report, dated Mar. 16, 2018, from corresponding PCT application No. PCT/EP2017/001406.

Ahmed et al., "Engineering anti-GD2 monoclonal antibodies for cancer immunotherapy", FEBS Letters, 2014, pp. 288-297, vol. 588.

Cochonneau et al., "Cell cycle arrest and apoptosis induced by O-acetyl-GD2-specific monoclonal antibody 8B6 inhibits tumor growth in vitro and in vivo", Cancer Letters, Jun. 10, 2013, vol. 333, No. 2, pp. 194-204, https://doi.org/10.1016/j.canlet.2013.01.032.

* cited by examiner

FIGURE 4 (suite)
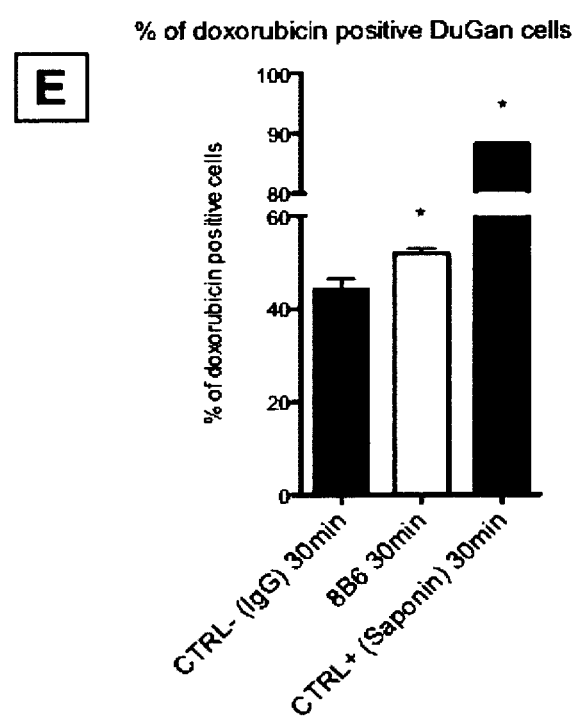

A

B

C

USE OF ANTIBODY AGAINST O-ACETYLATED GD2 GANGLIOSIDE TO IMPROVE THE THERAPEUTIC POTENTIAL OF DRUGS

The present patent application claims the priority of the European patent application EP 16002576.3 filed on Dec. 5, 2016, which is herein incorporated by reference.

FIELD OF THE INVENTION

The present invention relates to compositions comprising an anti-cancer agent and an antibody recognizing the specific O-acetylated form of GD2 ganglioside (namely OAcGD2 ganglioside) that enhances the uptake of said anti-cancer agent by cancer cells, and their uses in methods of treating, preventing and/or managing specific cancers characterized by cells expressing the OAcGD2 ganglioside.

BACKGROUND OF THE INVENTION

Delivery of anti-cancer agents to cells is a central aspect of therapeutic approaches against cancer. Biochemical properties of the anti-cancer agents rely on their molecular weight, on the environmental pH and also on their lipophilic versus hydrophilic profile.

The crossing of the cell membrane which is negatively charged is the first step for delivering anti-cancer agents to cells. It is now well established that a pH gradient occurs in animal tumors. Since anti-cancer agents are ionizable in aqueous medium, the acidic extracellular pH in tumor cells differentially modulates the activity of weakly basic or acid anti-cancer agents (MAHONEY et al., Biochemical Pharmacology, vol. 66, p: 1207-1218, 2003). In solution, most anti-cancer agents are present as both the non-ionized and ionized forms. Non-ionized anti-cancer agents are usually more lipid-soluble and can diffuse readily across the cell membrane. By contrast, ionized anti-cancer agents have low lipid solubility and are unable to penetrate the lipid membrane without parasitizing a transporter normally used for physiological substrates. This ion trapping mechanism can then alter drug accumulation, then significantly modulating chemotherapy efficiency.

Ability to overcome the biological barriers that face transferring an anti-cancer agent into cancer cells and tumors has to be balanced with the extent of toxicity. Among conventional anti-cancer agents, alkylating agents, antimetabolites or anti-tumor antibiotics directly damage or interfere with DNA or RNA to keep cancer cells from growing and multiplying. Other drugs, such as topoisomerase inhibitors or mitotic inhibitors, specifically target enzymes involve in cell cycle. Differentiating agents or hormones are also used either to make cancer cells mature into normal cells or to slow the growth of cancer. Almost all anti-cancer agents are toxic, and chemotherapy causes significant and often dangerous side effects including severe nausea, bone marrow depression, and immunosuppression.

Additionally, exposure to conventional anti-cancer agents may lead to chemotherapy failure and tumor progression, even with administration of combinations of anti-cancer agents. This phenomenon is often due to pre-existing precursor cells or newly emerging drug-resistant clones. Moreover, anti-cancer agents may cause serious side effects such as heart or nerve damage, or even more dramatically, can increase the risk of a second cancer a few years after the drugs are given.

More recently, the ability of RNA interference to silence target genes with high efficiency and specificity was used to develop drugs targeting RNA in human cells (BARATA et al., Cancer Treatment Reviews, vol. 50, p: 35-47, 2016). RNA-based therapies developed for cancer treatment rely on the use of double-stranded synthetic short RNA molecules (miRNAs) or synthetic DNA/RNA-like oligonucleotides (ASOs). The transfer of these molecules through the cell membrane of cancer cells is quite problematic due to their negative charge. This drawback can be attenuated by doing chemical modifications on oligonucleotides structure and/or by using delivery systems including viral vectors, biocompatible cationic polymers and copolymers, inorganic nanoparticles, atelocollagen and liposomes. However, these delivery systems influence pharmacokinetic processes of miRNA-based therapeutics and can also have toxicity. Moreover, delivery systems often require parameter optimization for every cell type.

Thus, new compositions and methods are needed to overcome the drawbacks of the drugs uptake in cancer cells and tumors to improve their therapeutic potential and also to reduce their side effects such as toxicity.

SUMMARY OF THE INVENTION

The inventors have previously demonstrated that a mouse therapeutic antibody targeting specifically the O-acetylated form of GD2 ganglioside (namely OAcGD2 ganglioside) show beneficial effects in treating cancers expressing the OAcGD2 ganglioside (EP 2076542 B1).

The inventors have now surprisingly found that this antibody, in addition to its own anti-cancer activity, is effective for treating cancer when used as an adjuvant for another anti-cancer agent. They have more particularly shown a synergistic effect on cancers expressing the OAcGD2 ganglioside of the combined treatment of an antibody targeting specifically the OAcGD2 ganglioside and of different anti-cancer agents, making it possible to reduce the dosage, and hence the toxic side effects, of the anti-cancer agents.

Consequently, the present invention relates to a composition for delivery of an anti-cancer agent into a cell expressing the OAcGD2 ganglioside comprising: (i) at least one anti-cancer agent, and (ii) at least one antibody recognizing the OAcGD2 ganglioside, a functional fragment or a derivative thereof, wherein the at least one antibody recognizing the OAcGD2 ganglioside favors the uptake of the at least one anti-cancer agent by the cell, and in turn its activity. Now, said at least one antibody, functional fragment or derivative thereof recognizing the OAcGD2 ganglioside is specific for said ganglioside.

In an embodiment, the at least one antibody recognizing the OAcGD2 ganglioside, a functional fragment or a derivative thereof, comprises a) a light chain variable region (VL) polypeptide having the amino acid sequence SEQ ID NO:1; and b) a heavy chain variable region (VH) having the amino acid sequence SEQ ID NO:2.

Also in certain embodiments, the at least one anti-cancer agent is selected from the group comprising or consisting of anti-cancer agents, such alkylating agents, anti-metabolites, anti-tumor antibodies, anti-tumor antibiotics, topoisomerase inhibitors, mitotic inhibitors, tyrosine kinase inhibitors, corticosteroids, hormones or hormone-like drugs, cytokines, nucleoside analogs, nucleic acids, such double-stranded synthetic short RNA molecules (miRNAs) or synthetic DNA/RNA-like oligonucleotides (ASOs).

The at least one anti-cancer agent may be unable to cross the cell membrane of cancer cells by themselves.

The at least one anti-cancer agent has a molecular mass ranging from 100 Daltons to 200,000 Daltons.

Another object of the present invention is to provide an antibody recognizing the OAcGD2 ganglioside, a functional fragment or a derivative thereof, for use in the selective delivery into a cell expressing the OAcGD2 ganglioside of an anti-cancer agent to treat cancer expressing the OAcGD2 ganglioside.

Another object of the present invention is to provide a method for delivery of an anti-cancer agent into a cell expressing the OAcGD2 ganglioside comprising contacting the cancer cell with at least one antibody recognizing the OAcGD2 ganglioside in an amount and concentration effective to enhance uptake of the anti-cancer agent by the cell, wherein the antibody causes permeability defects, such as pore formation, within the cell membrane.

Still another object of the present invention is to provide a method of preventing and/or treating cancer expressing the OAcGD2 ganglioside, comprising administering to a patient in need thereof a composition comprising: (i) at least one anti-cancer agent and, (ii) at least one antibody recognizing the OAcGD2 ganglioside, a functional fragment or a derivative thereof, and optionally (iii) a pharmaceutically acceptable carrier.

Still another object of the present invention is to provide a method of increasing sensitivity to an anti-cancer agent in a patient suffering from a cancer expressing the OAcGD2 ganglioside, comprising administering to a patient in need thereof a composition comprising: (i) at least one anti-cancer agent, (ii) at least one antibody recognizing the OAcGD2 ganglioside, a functional fragment or a derivative thereof, and optionally (iii) a pharmaceutically acceptable carrier.

Still another object of the present invention is to provide a method of preventing or delaying development of cancer resistant to an anti-cancer agent in a patient suffering from a cancer expressing the OAcGD2 ganglioside, comprising administering to a patient in need thereof a composition comprising (i) at least one anti-cancer agent, (ii) at least one antibody recognizing the OAcGD2 ganglioside, a functional fragment or a derivative thereof, and optionally (iii) a pharmaceutically acceptable carrier.

Another object of the present invention is to provide a method of identifying synergistic combination of (i) at least one anti-cancer agent and, (ii) at least one antibody recognizing the OAcGD2 ganglioside, a functional fragment or a derivative thereof, suitable for the prevention/and or the treatment of cancer expressing the OAcGD2 ganglioside.

Still another object of the present invention is to provide a new use of an antibody recognizing the OAcGD2 ganglioside, a functional fragment or a derivative thereof, for enhancing intracellular uptake of an anti-cancer agent in a cell expressing the OAcGD2 ganglioside.

Finally, the present invention relates to a kit comprising: (i) at least one anti-cancer agent, (ii) at least one antibody recognizing the OAcGD2 ganglioside, a functional fragment or a derivative thereof, and optionally (iii) a pharmaceutically acceptable carrier.

DETAILED DESCRIPTION OF THE INVENTION

Figure 1:
FIG. 1: Scanning electron microscopy was performed on neuroblastoma cell lines and glioblastoma primary cells incubated with 40 µg/ml of anti-OAcGD2 mAb 8B6 for 30 minutes. Untreated (or treated with an isotype-matched negative control mouse IgG3) IMR5 (panel A), LAN-1 (panel C) and DUASOII (panel E) cells share a continuous round shape whereas some pores appear in the membrane of anti-OAcGD2 mAb 8B6 treated IMR5 (panel B), LAN-1 (panel D) and DUASOII (panel F) cells. Magnifications are respectively of 2.5 Kilo fold (K×) (panels A, B, C, D and F) and 2.0 K× (panel E).
Figure 1:
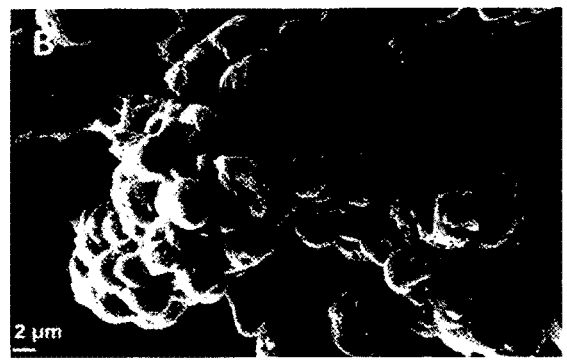
Figure 1:
Figure 1:
Figure 1:
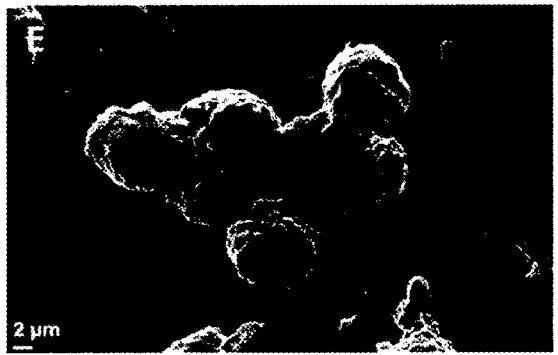
Figure 1:
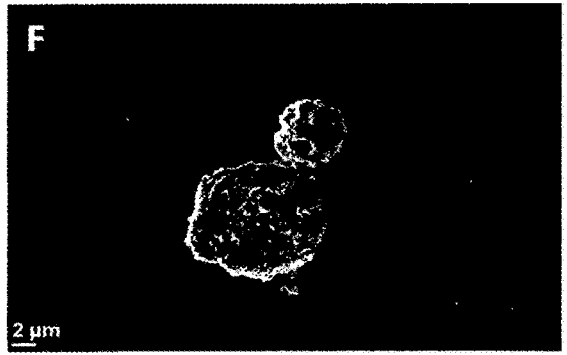

In a first aspect, the present invention relates to a method for delivery of an anti-cancer agent into a cell expressing the OAcGD2 ganglioside comprising contacting the cell with at least one antibody recognizing the OAcGD2 ganglioside, a functional fragment or a derivative thereof, in an amount and concentration effective to enhance uptake of the anti-cancer agent by the cell, wherein the antibody causes defects, such as pore formation, within the cell membrane.

Preferably, said at least one antibody recognizing the OAcGD2 ganglioside is a multimeric antibody.

In fact, the inventors have established that the antibodies recognizing the OAcGD2 ganglioside and having simultaneously multimerization properties (e.g. the 8B6 IgG3 antibody having aggregation properties and a chimerized 8B6 antibody comprising a chimerized IgG1 constant region having multimerization properties (i.e. hexamer formation)) induce penetration of an anti-cancer agent, whereas an antibody having no such multimerization properties (e.g. a chimerized 8B6 antibody comprising IgG1 constant region) has no effect on such penetration. Accordingly, it seems that both OAcGD2 ganglioside binding and multimerization properties are necessary for pores formation in the cell membrane of cells expressing OAcGD2 ganglioside. As used herein, the term "multimeric antibody" may refer to a dimer, a trimer, a quadrimer, . . . or to an aggregate.

For the purpose of the present invention, the terms cell membrane, cytoplasmic membrane, outer cell membrane and plasma membrane are equivalent and can be used indifferently.

The term "delivery of an anti-cancer agent into a cell" refers to the release of the anti-cancer agent inside a cell, so that the anti-cancer agent can reach its intracellular target.

According to a preferred embodiment, the cell expressing the OAcGD2 ganglioside is a tumor cell, a cancer cell, a cancer stem cell, or a hyperproliferative cell having the OAcGD2 ganglioside anchored to the cell membrane. The term "cancer stem cells" has its general meaning in the art and refers to a subpopulation of cancer cells (found within solid tumors and hematological cancers) that possess characteristics associated with normal stem cells, specifically the ability to give rise to all cell types found in a particular cancer sample. They have the capacity for self-renewal, differentiation into multiple cancer cell lineages and extensive proliferation. They can initiate new tumor with only a small amount of cancer stem cells and tend to be resistant to conventional therapy including chemotherapy and radiotherapy. Cancer stem cells have been identified in very different types of cancers, including, but not limited to, leukemia including acute myeloid leukemia and acute lymphoid leukemia, breast cancer, glioma including glioblastoma, colorectal cancer, pancreatic cancer, prostate cancer, lung cancer, liver cancer, bladder cancer or gastric cancer. Different markers have been observed as identifying cancer stem cells among the bulk of cancer cells, such markers varying and depending on the type of cancer. Examples of markers that can be used to identify cancer stem cells comprise, but are not limited to, CD34, CD38, CD19, interleukin-3-receptor a (CD123), CD33, CD44, CD44v6, CD47, CD24, EpCAM (ESA), Lin, CD133, A2B5, SSEA-1, CD166, CD26, CD200, 2β1, Sca, CD45, Pecam, ALDH, ALDH1, Oct4, ABCG2, CXCR4, AFP, EMA, IGF-IR.

The term "the uptake of an anti-cancer agent by a cell" refers to the contact and internalization/penetration of an anti-cancer agent into a target cell, such as a tumor cell, a cancer cell, a cancer stem cell, or a hyperproliferative cell. It is now well established that the crossing of the cell membrane is the first limiting step for an anti-cancer agent to reach its intracellular target.

The term "defects" refers to local cell membrane perturbation that causes cell transient deformation leading to an increase in cell membrane permeability. For example, local invagination or evagination of the cell membrane can result from the binding of at least one antibody recognizing the OAcGD2 ganglioside, a functional fragment or a derivative thereof, to a cell expressing the OAcGD2 ganglioside. In other words, transient increase in the cell membrane permeability of a cell expressing the OAcGD2 ganglioside occurs only in the presence of at least one antibody recognizing the OAcGD2 ganglioside, a functional fragment or a derivative thereof. The defects can be transient so that the cell membrane can retract back to its original conformation.

The term "pore formation" refers to a physical modification or disruption of the glycerophospholipid bilayer leading to the formation of holes within the cell membrane. This leads to transient increase in the permeability of cell membranes and may also play a role in endocytosis of extracellular molecules. The pore formation allows the entry of a molecule from the extracellular compartment to the intracellular compartment. The number and the diameter of the pores depend on several parameters such as cell type, cell membrane composition, quantity and duration of the antibody contacting the cell. The pore size determines the size of agents that can be delivered into the cytoplasm of the cell using the method of the invention. Scanning electron microscopy (SEM) and atomic force microscopy (AFM) can be used to gauge pore size (ZHAO et al, Journal of Drug Targeting, 16:1, 18-25, 2008).

According to a preferred embodiment, the mean diameter of the membrane pore is between about 1 nm to about 100 nm, preferably between about 1 nm to about 50 nm, and most preferably between about 1 nm to about 10 nm.

Lipid bilayer cell membranes are 4-10 nm thick. Hence, the mean diameter of the pore can be, in some cases, largely superior to cell membrane thickness.

In all embodiments, the antibody recognizing the OAcGD2 ganglioside, a functional fragment or a derivative thereof, creates on the cell membrane non-selective pores. By "non-selective pore" is intended pore allowing uncharged or charged molecules, such as ionized anti-cancer agent to diffuse through the phospholipid bilayer of the cell membrane. The pore size is a relevant criterion for the selection of uncharged or charged compounds that cross the cell membrane.

When brought into contact with a cell expressing the OAcGD2 ganglioside under appropriate conditions, the antibody recognizing the OAcGD2 ganglioside, a functional fragment or a derivative thereof, has the capability of inducing cell penetration of an anti-cancer agent within part or all cells of a given cell culture population by causing pore within the cell membrane. By "cell penetration" is intended the passing of an anti-cancer agent from the external environment in the intracellular environment in conditions significantly better than passive diffusion.

This discovery provides an entirely new approach to treating cancer expressing OAcGD2 ganglioside. By performing non-selective pores in cancer cells, the antibody recognizing the OAcGD2 ganglioside, a functional fragment or a derivative thereof, greatly enhance the permeability of cancer cells to anti-cancer agents. This may result not only to an increase of their therapeutic affect but also to a reduction of their related potential side effects.

When employed in vitro and/or ex vivo, the method of the invention is implemented for drug screening purposes. Hence, a method for in vitro and/or ex vivo delivery of an anti-cancer agent into a cell, preferably a tumor cell, expressing the OAcGD2 ganglioside is suitable for the screening of synergistic combinations of anti-cancer agents and antibodies recognizing the OAcGD2 ganglioside, a functional fragment or a derivative thereof.

Thus, the present invention also relates to a composition for delivery of an anti-cancer agent into a cell, preferably a tumor cell, expressing the OAcGD2 ganglioside comprising: (i) at least one anti-cancer agent, (ii) at least one antibody recognizing the OAcGD2 ganglioside, a functional fragment or a derivative thereof, wherein the at least one antibody recognizing the OAcGD2 ganglioside enhances the uptake of the at least one anti-cancer agent by the cell, preferably the tumor cell.

When employed in vivo, the method of the invention is implemented for therapeutic purposes. Hence, a method for in vivo delivery of an anti-cancer agent into a cell, preferably a tumor cell, expressing the OAcGD2 ganglioside is suitable for the treatment of cancer expressing the OAcGD2 ganglioside.

Thus, the present invention also relates to a composition comprising: (i) at least one anti-cancer agent, (ii) at least one antibody recognizing the OAcGD2 ganglioside, a functional fragment or a derivative thereof, and optionally (iii) a pharmaceutically acceptable carrier, for use in a method for the treatment and/or prevention of cancer expressing the OAcGD2 ganglioside.

The present invention also relates to an antibody recognizing the OAcGD2 ganglioside, a functional fragment or a derivative thereof, for use in the selective delivery into cell expressing the OAcGD2 ganglioside of at least one anti-cancer agent to treat and/or to prevent cancer.

The present invention also relates to a method of preventing and/or treating cancer expressing the OAcGD2 ganglioside, comprising administering to a patient in need thereof an effective amount of a composition comprising: (i) at least one anti-cancer agent and, (ii) at least one antibody recognizing the OAcGD2 ganglioside, a functional fragment or a derivative thereof, and optionally (iii) a pharmaceutically acceptable carrier.

The terms "method for the treatment of cancer expressing the OAcGD2 ganglioside" or "method of treating cancer expressing the OAcGD2 ganglioside" are equivalent and refer to curing, reversing, attenuating, alleviating, minimizing, suppressing or halting the deleterious effects of a cancer expressing the OAcGD2 ganglioside or cancer expressing the OAcGD2 ganglioside progression or attenuating the progression of a cancer expressing the OAcGD2 ganglioside. Preferably, such treatment also leads to the regression of tumor growth or metastasis spread, i.e., the decrease in size of a measurable tumor. Most preferably, such treatment leads to the complete regression of the tumor.

The term "cancer expressing the OAcGD2 ganglioside" refers to cancer having cells expressing the O-acetylated form of GD2 ganglioside on their surface. Typically, said cells express more than 1,000 OAcGD2 ganglioside molecules on their cell surface, preferably more than 10,000, and more preferably more than 50,000 OAcGD2 ganglioside molecules on their cell surface. Said cancer expressing the OAcGD2 ganglioside are selected from the group comprising or consisting of neuroblastoma, glioma, retinoblastoma, Ewing's family of tumors, sarcoma (i.e. rhabdomyosarcoma, osteosarcoma, leiomyosarcoma, liposarcoma, and fibrosarcoma), small cell lung cancer, breast cancer, melanoma, metastatic renal carcinoma, head and neck cancer and hematological cancers (i.e. leukemia, Hodgkin lymphoma, non Hodgkin lymphoma and myeloma). More generally, term "cancer expressing the OAcGD2 ganglioside" refers to cancer presenting more than 10% of cells expressing the OAcGD2 ganglioside, preferably more than 15%, and still more preferably more than 20%. Preferably, said cells are Cancer Stem Cells (CSCs). Treatment" of cancer expressing the OAcGD2 ganglioside refers to the administration of the composition comprising: (i) at least one anti-cancer agent, (ii) at least one antibody recognizing the OAcGD2 ganglioside, a functional fragment or a derivative thereof, and optionally (iii) a pharmaceutically acceptable carrier to destroy the tumor or to destroy cancer cells expressing the OAcGD2 ganglioside on their surface.

"Prevention" of cancer expressing the OAcGD2 ganglioside refers to the administration of the composition comprising: (i) at least one anti-cancer agent, (ii) at least one antibody recognizing the OAcGD2 ganglioside, a functional fragment or a derivative thereof, and optionally (iii) a pharmaceutically acceptable carrier to reduce tumor growth or to imped metastasis spread or even to block tumor returning. Preferably, an outcome of prevention may be preventing metastasis spread from occurring if the treatment is administered prior to the relapse in a subject already suffering from a cancer expressing the OAcGD2 ganglioside. Most preferably, another outcome of prevention may be preventing the tumor return in a subject having already being treated for a cancer expressing the OAcGD2 ganglioside.

As used herein, the term "patient" refers to any mammals, including humans. It is not intended that the term be limited to a particular age or sex. Thus, adult and newborn subjects, as well as children, whether male or female, are encompassed by the term.

The term "anti-cancer agent" refers to chemical, physical or biological agent or compound with anti-proliferative, anti-oncogenic and/or carcinostatic properties which can be used to inhibit tumor growth, proliferation and/or development. Preferably, the anti-cancer agent has an anti-cancer expressing the OAcGD2 ganglioside activity.

The at least one anti-cancer agent can be selected from the group comprising or consisting of anti-cancer agent such as alkylating agents, anti-metabolites, anti-tumor antibodies, anti-tumor antibiotics, topoisomerase inhibitors, mitotic inhibitors, tyrosine kinase inhibitors, corticosteroids, hormones or hormone-like drugs, cytokines, nucleoside analogs, nucleic acids, such double-stranded synthetic short RNA molecules (miRNAs) or synthetic DNA/RNA-like oligonucleotides (ASOs).

The at least one anti-cancer agent may be unable to cross the cell membrane of cancer cells for itself.

In all embodiments, the anti-cancer agent has a steric hindrance compatible with the size of the pore ranging from about 1 nm to about 2 µm, so that it can cross the cell membrane through the pore resulting from contacting a cell with an antibody recognizing the OAcGD2 ganglioside, a functional fragment or a derivative thereof.

In some embodiments, anti-cancer agent can be embedded in biocompatible and biodegradable nanoparticles. This is particularly appropriated when anti-cancer agent is a nucleic acid, such double-stranded synthetic short RNA molecules (miRNAs) or synthetic DNA/RNA-like oligonucleotides (ASOs) or a short polypeptide to protect them from being cleaved by nucleases or proteases.

In this case, the type of nanoparticles can be selected by the skilled artisan based on their size as well as their physicochemical and pharmacokinetic characteristics. For example, miRNA was successfully delivered to cancer cells by using iron oxide nanoparticles in animal model of gastric adenocarcinoma (HIRAKI et al., Molecular Therapy—Nucleic Acids (2015) 4, e231), and carbonate apatite nanoparticles in animal model of colorectal adenocarcinoma (SUN et al., 2014, Mol Cell Biochem, vol. 390, pp 19-30). The size distribution of nanoparticles can be measured using different techniques, such as atomic force microscopy (AFM), transmission electron microscopy (TEM) and dynamic light scattering (DLS). For example, single particle size of iron oxide nanoparticles was being 10-60 nm, and that composed of carbonate apatite nanoparticles was 70-80 nm and up to 200-300 nm if they form an aggregate.

Nanoparticles can also be used for the anti-cancer agents used in chemotherapy that are distributed evenly within the body of the patient and which cannot distinguish the cancer cells from the healthy ones.

In recent years, considerable effort has been directed towards ultrasmall inorganic particles (USNPs) for therapy of cancer. Gold USNPs have a core size ranging from 1 to 3 nm.

The size of nanoparticles and ultrasmall nanoparticles is compatible with the size of the pore observed within the cell membrane of cancer cells expressing the OAcGD2 ganglioside when incubated with the antibody recognizing the OAcGD2 ganglioside.

In some embodiments, anti-cancer agents are not embedded in nanoparticles. In this case, anti-cancer agents in solution are non-spherical, dynamic (tumbling) and solvated. The apparent size of the dynamic, hydrated, solvated anti-cancer agent can thus be determined using the diffusional properties of the anti-cancer agent. Dynamic Light Scattering (DLS) is considered as the best technique to calculate the hydrodynamic radius (Rh) which is defined as the radius of an equivalent hard sphere diffusing at the same rate as the molecule under observation. Rh is indicative of the apparent size of the dynamic hydrated/solvated molecule. Rh is generally calculated from the diffusion coefficient using the Stokes-Einstein equation. Radius of gyration (Rg), defined as the mass weighted average distance from the core of a molecule to each mass element in the molecule, is another parameter allowing the determination of the size of molecule. It is possible, however, to obtain Rg for molecules using other techniques such as small angle neutron scattering (SANS) and small angle x-ray scattering (SAXS) or from high resolution x-ray structures.

It can be also appropriate to characterize the anti-cancer agent forming part of the composition use to treat cancer by its molecular mass.

In a preferred embodiment, the anti-cancer agent has a molecular mass ranging from 100 Daltons to 200,000 Daltons.

By "molecular mass" is meant the average mass of a molecule, calculated by summing the atomic weights of atoms in the molecular formula defining said molecule. The words mass and weight are used interchangeably in the present invention. By "atomic weight" is meant weighted average of isotopic masses found in a typical terrestrial sample of the element as disclosed on the periodic table of Mendeleyev.

A definition of the Dalton can be found in the Green Book (IUPAC, Green book, Third Edition, "Quantities, Units and Symbols in physical chemistry", 2007). The Dalton, symbol Da, is used as an alternative name for the unified atomic mass unit, symbol u. The Dalton is related to the mass of the carbon-12 nuclide and is defined as the $1/12$ mass of carbon-12 atom ($m_a(^{12}C)/12 \approx 1.666\ 538\ 782\ (83) \times 10^{-27}$ kg=$10^{-3}$/ Na (kg), wherein Na is the Avogadro constant being equal to $6.022\ 14 \times 10^{23}$ mol$^{-1}$). It follows therefore that the molar mass of carbon-12 is 12 g/mol exactly. This has the consequence that molar masses are numerically identical to atomic weights when they are expressed in the SI units of g/mol (eq. to g·mol$^{-1}$). As an example, the molar mass of water ($H_2O$) is 18 g·mol$^{-1}$ and its molecular mass is 18 Da. The Dalton may be combined with the SI prefixes to express the masses of large molecules in kilodalton (kDA) or megadalton (MDa). For example, an anti-cancer agent with a molar mass of 200,000 g·mol$^{-1}$ has a molecular mass of 200,000 Da, which also can be defined as 200 kDa.

Also, in certain embodiments, the anti-cancer agent of the compositions according to the invention has a molecular mass ranging from 10 kDa to 15 kDa, more preferably from 11 kDa to 14 kDa, more preferably from 12 kDa to 13 kDa. Most preferably, the anti-cancer agent of the compositions according to the invention has a molecular mass ranging from 10 kDa to 13 kDa.

In other embodiments, the anti-cancer agent of the compositions according to the invention has a molecular mass ranging from 80 kDa to 200 kDa, more preferably from 100 kDa to 180 kDa, more preferably from 120 kDa to 160 kDa. Most preferably, the anti-cancer agent of the compositions according to the invention has a molecular mass ranging from 150 kDa to 200 kDa.

In other embodiments, the anti-cancer agent of the compositions according to the invention has a molecular mass ranging from 120 Daltons to 800 Daltons, more preferably from 150 Daltons to 600 Daltons, more preferably from 250 Daltons to 550 Daltons. Most preferably, the anti-cancer agent of the compositions according to the invention has a molecular mass ranging from 120 Daltons to 550 Daltons.

Also in certain embodiments, the at least one anti-cancer agent is selected from the group of anti-cancer agents comprising or consisting of anti-tumor antibiotics, such as anthracyclines, topoisomerase inhibitors, such as camptothecins, alkylating agents, such as imidazotetrazines or cyclophosphamide, prenol lipids, antimetabolites, such as diazines and transition metal salts.

Anthracyclines are one of the most efficient classes of drugs in the treatment of cancer. Originated in the 1950's, these molecules were firstly identified from the soil bacterium *Streptomyces peucetius*. Anthracyclines are composed of a rigid planar tetracyclic structure with adjacent quinone and hydroquinone moieties, a short side chain with a carbonyl group at C-13, and an aminosugar daunosamine attached by a glycosidic bond to the C-7 of the tetracyclic ring. Anthracyclines enter the cell through passive diffusion and are able to interact with the topoisomerase-DNA complex, thereby inhibiting cellular growth. Despite an efficient activity in killing cancer cells, only a few of them has been approved for medicinal use such as daunorubicin, doxorubicin, idarubicin, epirubicin, valrubicin, mitoxantrone or pixantrone. Moreover, their clinical usefulness is limited by a cumulative dose-dependent cardiotoxicity, which can cause irreversible heart failure. Preferably, the anthracycline used in the composition of the invention is selected from the group comprising or consisting of daunorubicin, doxorubicin, idarubicin, valrubicin and other derivatives thereof. Most preferably, the anthracycline used in the composition of the invention is doxorubicin, or one of its derivatives thereof.

In all embodiments, the composition according to the present invention contains therapeutically effective amount of at least one anti-cancer agent and therapeutically effective amount the at least one antibody recognizing the OAcGD2 ganglioside, a functional fragment or a derivative thereof.

As used herein, the term "therapeutically effective amount" is intended to encompass any amount that will achieve the desired therapeutic or biological effect. The therapeutic effect is dependent upon the cancer expressing the OAcGD2 ganglioside treated or the biological effect desired. As such, the therapeutic effect can be a decrease in the severity of symptoms associated with the cancer expressing the OAcGD2 ganglioside and/or inhibition (partial or complete) of progression of the cancer expressing the OAcGD2 ganglioside. The amount needed to elicit the therapeutic response can be determined based on cancer type, the age, health, size and sex of the patient.

According to a preferred embodiment, doxorubicin or one of its derivatives can be administered at a dose comprised between 40 mg/m$^2$ and 60 mg/m$^2$ for an adult subject, during 1 to 3 days, every 3 or 4 weeks. The maximal cumulative dose of doxorubicin or one of its derivatives should not exceed 600 mg/m$^2$. The dose is reduced between 25 mg/m$^2$ and 30 mg/m$^2$ for a child (MATTHAY et al., N Engl J Med, 1999, vol. 341, pp. 1165-1173). To convert dose in mg/m$^2$ to dose in mg/kg, simply divide by 37 for human (NAIR and JACOB, J Basic Clin Pharm., 2016, vol. 7(2):pp. 27-31)

Doses given herein are for adult and/or child humans, but can be adjusted to the size of other mammals, in accordance with weight or square meter size.

Camptothecins are heterocyclic compounds comprising a planar pentacyclic ring structure, that includes a pyrrolo[3,4-beta]-quinoline moiety (rings A, B and C), conjugated pyridone moiety (ring D) and one chiral center at position 20 within the alpha-hydroxy lactone ring with (5) configuration (the E-ring). These quinoline-based alkaloids were initially extracted from the Asian tree *Camptotheca acuminate*. Topotecan and irinotecan are the only two camptothecins derivatives drugs approved for their use in treating cancer. Preferably, the camptothecin used in the composition of the invention is selected from the group comprising or consisting of topotecan, irinotecan, rubitecan and other derivatives. Most preferably, the camptothecin used in the composition of the invention is topotecan, irinotecan or one of their derivatives.

According to a preferred embodiment, topotecan or one of its derivatives can be administered for an adult subject at a starting dose of 1.5 mg/m$^2$ during 5 days, every 3 weeks and then at a dose comprised between 1 mg/m$^2$ and 1.5 mg/m$^2$, during 5 days, every 3 weeks. The dose is reduced to 0.75 mg/m$^2$ for a child, during 5 days, every 28 days (DI GIANNATALE et al. Phase II study of temozolomide in combination with topotecan (TOTEM) in relapsed or refractory neuroblastoma: a European Innovative Therapies for Children with Cancer-SIOP-European Neuroblastomastudy and Reza Rahbar, Carlos Rodriguez-Galindo, John G. Meara, Edward R. Smith, Antonio R. Perez-Atayde. 2 decembre 2013 Springer Science & Business Media).

According to another preferred embodiment, irinotecan or one of its derivatives can be administered for an adult subject at a of 340-350 mg/m$^2$ by an i.v infusion of 90 minutes, every 3 weeks (FRIEDMAN et al., J. Clin. Oncol., vol. 27(28), p: 4733-4740, 2009).

Doses given herein are for adult and/or child humans, but can be adjusted to the size of other mammals, in accordance with weight or square meter size.

Imidazotetrazines are a class of heterobicyclic compounds containing ortho-fused imidazole and tetrazine rings. Among these compounds, temozolomide (Temodar®, Temodal®, TMZ) has been approved for the treatment of newly diagnosed glioblastoma multiforme (GBM) and also for refractory anaplastic astrocytoma. This pro-drug needs to be activated to be active. Despite a clear benefit to a subset of patients suffering from glioblastoma, TMZ also induces progressive tumor growth associated with emergence of TMZ resistance. Preferably, the imidazotetrazine used in the composition of the invention is temozolomide or one of its derivatives.

According to a preferred embodiment, temozolomide or one of its derivatives can be administered at a dose comprised between 75 mg/m$^2$ and 200 mg/m$^2$ for an adult subject, during 1 day.

Doses given herein are for humans, but can be adjusted to the size of other mammals, as well as children, in accordance with weight or square meter size.

Prenol lipids are synthesized from the five carbon precursor isopentenyl diphosphate and dimethylallyl diphosphate that are produced mainly via the mevalonic acid pathway. Because the simple isoprenoids (linear alcohols, diphosphates, etc.) are formed by the successive addition of C5 units, it is convenient to classify them in this manner, with a polyterpene subclass for those structures containing more than 40 carbons (i.e., >8 isoprenoid units). For example, vitamin A and its derivatives and phytanic acid and its oxidation product pristanic acid are grouped under C20 isoprenoids. Carotenoids are important simple isoprenoids that function as antioxidants and as precursors of vitamin A. Another biologically important class of molecules is exemplified by the quinones and hydroquinones, which contain an isoprenoid tail attached to a quinonoid core of nonisoprenoid origin. Vitamins E and K as well as the ubiquinones are examples of this class. Among prenol lipids, retinoids are natural and synthetic derivatives of vitamin A. Several studies reported their use as powerful differentiation inducers or inducer of tumor cell apoptosis for treating cancer such as acute myeloid leukemia (AML). For example, vitamin A derivatives include retinoic acid (RA), all-trans retinoic acid (ATRA), 9-cis RA, 4-HPPR, 13-cis RA and synthetic analogs of retinoic acid such as AM 580. Recently, 13-cis RA was found beneficial in the treatment of high-risk neuroblastoma after bone marrow transplantation (Matthay et al., N Engl 1 Med; 341:1165-1173, 1999). Preferably, the prenol lipid used in the composition of the invention is selected from the group comprising or consisting of ATRA, 9-cis RA and 13-cis RA. Most preferably, the prenol lipid used in the composition of the invention is 13-cis RA, also called isotretinoin.

According to a preferred embodiment, isotretinoin can be administered at a dose comprised between 80 mg/m$^2$ and 160 mg/m$^2$ for an adult subject (Y U et al., N Engl J Med., 2010, vol. 363(14):pp. 1324-1334).

Doses given herein are for humans, but can be adjusted to the size of other mammals, as well as children, in accordance with weight or square meter size.

Diazines are organic compounds containing a five-member heterocyclic compound with five nitrogen atoms, and two nitrogen atoms at positions 1 and 2 (Pyridazines), 1 and 3 (Pyrimidines), or 1 and 4 (Pyrazines). Preferably, the diazine used in the composition of the invention is selected from the group of pyrimidines and pyrimidines derivatives comprising or consisting of thioguanine, fludarabine, cladribine, cytarabine, gemcitabine, 6-Mercaptopurine, 5-Fluorouracil (5-FU) and relatives. Most preferably, the diazine used in the composition of the invention is 5-FU or fludarabine.

According to a preferred embodiment, 5-FU can be administered at a dose comprised between 350 mg/m$^2$ and 400 mg/m$^2$ for an adult subject, during 4 to 5 days, every 4 weeks.

According to a preferred embodiment, fludarabine can be administered at an oral dose of 40 mg/m$^2$/day for 5 consecutive days, every 28 days. Doses given herein are for humans, but can be adjusted to the size of other mammals, as well as children, in accordance with weight or square meter size.

IUPAC defines the transition metals as any element with an incompleted subshell or that may form stable ions only with an incomplete d subshell. The transition metals are the forty chemical elements 21 to 30, 39 to 48, 71 to 80, and 103 to 112 in the periodic table of elements. Preferably, the transition metal used in the composition of the invention is selected from the group comprising or consisting of cisplatin, oxaliplatine, eptaplatin, lobaplatin, nedaplatin, carboplatin, iproplatin, satraplatin, tetraplatin, DCP, PLD-147, JM118, JM126, JM335 and other derivatives. Most preferably, the transition metal used in the composition of the invention is carboplatin or cisplatin.

According to a preferred embodiment, cisplatin can be administered for an adult subject at a dose comprised between 50 mg/m$^2$ and 100 mg/m$^2$, every 3 or 4 weeks. The dose is 60 mg/m$^2$ for a child, every 28 days.

According to a preferred embodiment, carboplatin can be administered at a dose comprised between 300 mg/m$^2$ and 400 mg/m$^2$ for an adult subject, every 3 or 4 weeks. The dose is 200 mg/m$^2$ for a child, every 21 days (Kohler et al., European Journal of Cancer (2013) 49, 3671-3679).

Doses given herein are for adult and/or child humans, but can be adjusted to the size of other mammals, in accordance with weight or square meter size.

Nitrogen mustard compounds are compounds having two beta-haloalkyl groups bound to a nitrogen atom. Among this class of compounds, cyclophosphamide has been used in the treatment of variety of cancers.

According to a preferred embodiment, cyclophosphamide can be administered for an adult subject at a dose comprised between 400 mg/m$^2$ and 1800 mg/m$^2$, divided over 2-5 days; may be repeated at intervals of 2-4 weeks for intermittent therapy and between 60 mg/m$^2$ and 120 mg/m$^2$/day for continuous daily therapy. The dose is between 1.5 mg/m$^2$ and 3 mg/m$^2$/day for 5 days in a child.

Doses given herein are for adult and/or child humans, but can be adjusted to the size of other mammals, in accordance with weight or square meter size.

According to a preferred embodiment, when the composition comprising at least one antibody recognizing the OAcGD2 ganglioside, a functional fragment or a derivative thereof is used to prevent and/or to treat a cancer expressing the OAcGD2 ganglioside selected from the group comprising or consisting of neuroblastoma, glioma, retinoblastoma, Ewing's family of tumors, sarcoma (i.e. rhabdomyosarcoma, osteosarcoma, leiomyosarcoma, liposarcoma, and fibrosarcoma), small cell lung cancer, breast cancer, melanoma, metastatic renal carcinoma, head and neck cancer and hematological cancers (i.e. leukemia, Hodgkin lymphoma, non Hodgkin lymphoma and myeloma), the at least one anti-cancer agent is selected from the group comprising or consisting of cyclophosphamid, doxorubicin, topotecan, irinotecan, temozolomide (TMZ), retinoic acid (RA), 5-Fluorouracil (5-FU), fludarabine, carboplatin and cisplatin.

According to a another preferred embodiment, when the composition comprising at least one antibody recognizing the OAcGD2 ganglioside, a functional fragment or a derivative thereof is used to prevent and/or to treat neuroblastoma, the anti-cancer agent is temozolomide, topotecan, irinotecan, fludarabine, cyclophosphamide or a mixture thereof.

In this preferred embodiment, each of the compounds (i.e. the antibody recognizing the OAcGD2 ganglioside and the anti-cancer agent) claimed in combination as a treatment for cancer expressing the OAcGD2 ganglioside is separately known to possess a therapeutic activity against the same disease or related conditions. Combining the antibody recognizing the OAcGD2 ganglioside and the anti-cancer agent gives rise to an unexpected technical effect, i.e. synergy.

In certain embodiment, the at least one antibody recognizing the OAcGD2 ganglioside, a functional fragment or a derivative thereof, comprises:

a) a light chain variable region (VL) polypeptide having the amino acid sequence SEQ ID NO:1; and b) a heavy chain variable region (VH) having the amino acid sequence SEQ ID NO:2.

The term "variable region" refers to the domains of an antibody heavy (VH) and light chain (VL) that is involved in binding the antibody to antigen.

According to a preferred embodiment, the light chain variable region (VL) polypeptide is the amino acid sequence SEQ ID NO:3.

Preferably, the light chain variable region (VL) polypeptide is selected in the group comprising or consisting of SEQ ID NO:4, SEQ ID NO:5, SEQ ID NO:6 and SEQ ID NO:7.

According to another preferred embodiment, the light chain variable region (VL) polypeptide has the amino acid sequence selected in the group comprising or consisting of SEQ ID NO: 34, SEQ ID NO: 35, SEQ ID NO: 36, SEQ ID NO: 37, SEQ ID NO: 38, SEQ ID NO:39 and SEQ ID NO: 40.

Preferably, the light chain variable region (VL) polypeptide has the amino acid sequence selected in the group comprising or consisting of SEQ ID NO:39 and SEQ ID NO: 40.

According to another preferred embodiment, the heavy chain variable region (VH) polypeptide is the amino acid sequences SEQ ID NO:8.

Preferably, the heavy chain variable region (VH) polypeptide is selected in the group comprising or consisting of SEQ ID NO:9, SEQ ID NO:10 and SEQ ID NO:11.

According to another preferred embodiment, the heavy chain variable region (VH) polypeptide has the amino acid sequence selected in the group comprising or consisting of SEQ ID NO: 41, SEQ ID NO: 42, SEQ ID NO: 43, SEQ ID NO:44, SEQ ID NO:45, SEQ ID NO:46, SEQ ID NO: 47, SEQ ID NO:48, SEQ ID NO:49, SEQ ID NO: 50, and SEQ ID NO:51.

Preferably, the heavy chain variable region (VH) polypeptide has the amino acid sequence selected in the group comprising or consisting of SEQ ID NO:48, SEQ ID NO:49, and SEQ ID NO: 50.

According to another preferred embodiment, the light chain variable region (VL) polypeptide is the amino acid sequence SEQ ID NO:12.

According to another preferred embodiment, the heavy chain variable region (VH) polypeptide is the amino acid sequences SEQ ID NO:13.

Still more preferably, the at least one antibody recognizing the OAcGD2 ganglioside, a functional fragment or a derivative thereof, comprises:

a) a light chain variable region (VL) polypeptide having the amino acid sequence SEQ ID NO:14; and b) a heavy chain variable region (VH) having the amino acid sequence SEQ ID NO:15.

The complementarity-determining regions (CDRs) of the heavy (VH) chain variable region having amino acid sequences represented in SEQ ID NO:16, SEQ ID NO:17 and SEQ ID NO:18, and the complementarity-determining regions of the light (VL) chain variable region having amino acid sequences represented in SEQ ID NO:19, SEQ ID NO:20 and SEQ ID NO:21.

In another particular embodiment, the at least one antibody recognizing the OAcGD2 ganglioside, a functional fragment or a derivative thereof, comprising:

a) a heavy chain comprising three heavy chain complementary regions (CDRs) having the amino acid sequences SEQ ID NO:16, SEQ ID NO:17 and SEQ ID NO:18, and a heavy chain framework sequence from an immunoglobulin heavy chain, and b) a light chain comprising three light chain complementary regions (CDRs) having the amino acid sequences SEQ ID NO:19, SEQ ID NO:20 and SEQ ID NO:21, and a light chain framework sequence from an immunoglobulin light chain.

The complementarity-determining regions (CDRs) occur respectively at amino acid residues 26-35 (CDR1_VH), 50-68 (CDR2_VH), 99-108 (CDR3_VH) of SEQ ID NO:15 and at amino acid residues 24-39 (CDR1_VL), 54-60 (CDR2_VL), 94-102 (CDR3_VL) of SEQ ID NO:14.

The assignment of amino acids to each CDR is in accordance with well-known numbering systems including IMGT, Kabat and Chothia systems (IMGT, The International Immunogenetics Information System®, LEFRANC et al., Nucleic Acids Research, vol. 27, p: 209-212, 1999; KABAT, sequences of Proteins of Immunological Interest, 5th edition. U.S. Department of Health and Human Services, Public Health Service, National Institutes of Health, NIH publication, No91-3242, 991; CLOTHIA & LESK, J Mol Biol., vol. 196(4), p: 901-917, 1987).

The term "an antibody recognizing the OAcGD2 ganglioside" refers to an equilibrium association constant ($K_A$) of an antibody for OAcGD2 ganglioside of more than $2 \times 10^5$ M at 25° C., preferably a $K_A$ of equal to or less than $2 \times 10^6$ M, more preferably a $K_A$ of equal to or more than $1 \times 10^7$ M or even $2 \times 10^7$ M. Such affinity can be simply measured by techniques available in the art, e.g. Scatchard assay, competition ELISA, BIACORE assay or KINEXA assay.

According to the present invention, the antibody used in the compositions according to the invention is not specific for GD2 ganglioside. The equilibrium association constant ($K_A$) of the antibody used in the composition according to the invention is at least 10 fold weaker, more preferably of at least 100 fold weaker for GD2 ganglioside than for OAcGD2 ganglioside. Preferably, the equilibrium association constant ($K_A$) of the antibody for GD2 ganglioside of less than $10^5$ M at 25° C., preferably a $K_A$ of less than $10^4$ M for GD2 ganglioside.

The term "functional fragment" refers to antibody fragments, which bind specifically to the OAcGD2 ganglioside. Such fragments can be simply identified by the skilled person and comprise, as an example, scFv fragment, Fab fragment (e.g., by papain digestion), Fab' fragment (e.g., by pepsin digestion and partial reduction), F(ab')2 fragment (e.g., by pepsin digestion), Facb (e.g., by plasmin digestion), and also Fv and Fd (e.g., by pepsin digestion, partial reduction and re-aggregation) fragments are encompassed by the invention.

Such fragments can be produced by enzymatic cleavage, synthetic or recombinant technique using well known method in the art, such as described in STANWORTH et al (Handbook of Experimental Immunology, vol. 1, chapter 8, Blackwell Scientific Publications, 1978). Antibodies can also be produced in a variety of truncated forms using antibody genes in which one or more stop codons have been introduced upstream of the natural stop site. For example, a combination gene encoding a F(ab')2 heavy chain portion can be designed to include DNA sequences encoding the CH1 domain and/or hinge region of the heavy chain. The various portions of antibodies can be joined together chemically by conventional techniques, or can be prepared as a contiguous protein using genetic engineering techniques.

Now, these fragments comprise at least the variable regions of the heavy and light chains described previously. These fragments can be soluble, but also anchored within the cell membrane, as a single-chain variable part of a chimeric antigen receptor (CAR).

The term "chimeric antigen receptors (CARs)," as used herein, refers to an artificial hybrid polypeptide comprising at least one antigen binding domain of an antibody and at least one effector cell signaling domain. Such CARs encompass engineered receptors that graft an artificial specificity onto a particular immune effector cell (e.g. T cells, NK cells and NKT cells). CARs may be employed to impart the specificity of a monoclonal antibody onto a T cell in a non-MHC-restricted manner, thus exploiting the antigen-binding properties of monoclonal antibodies. When expressed in T-cells, CARs recognize unprocessed antigens independently of their expression of major histocompatibility antigen which is unlike the physiologic T-Cell Receptors (TCR), thus bypassing two major mechanisms of tumor escape, the downregulation of HLA expression or proteosomal antigen processing. The binding of CARs to a specific antigen elicits an immune response.

In particular aspects, CARs comprise an ectodomain, a transmembrane domain and an endodomain. Now, the arrangement could be multimeric, such as a diabody or also multimers (e.g., the multi-chain chimeric antigen receptor described in International Patent application PCT WO 2016/016343).

The ectodomain corresponds to the antigen binding domain and to the spacer domain (stalk region). The antigen binding domain is preferably a single-chain variable fragment (scFv). Such scFv is a genetically engineered antibody fragment that usually consists of the heavy chain and light chain of an immunoglobulin, or parts thereof such as VH and VL, joined together by a flexible peptide linker as disclosed as an example in PLUCKTHUN (The Pharmacology of Monoclonal Antibodies, vol. 113, Rosenburg and Moore eds., Springer-Verlag, New York, p: 269-315, 1994). The flexible peptide linker can be a peptide of between 6 to 40 amino acid residues. The use of small amino acids such as alanine and glycine are of use in creating flexible linker. Exemplary flexible linkers include glycine polymers (G)n, glycine-serine polymers such as for example $(GS)_n$, $GSGGS_n$ (SEQ ID NO:22)n, $GGGS_n$ (SEQ ID NO:23)n and $GGGGS_n$ (SEQ ID NO:24)n, where n is an integer of at least one, glycine-alanine polymers or glycine-serine polymers, or other flexible linkers known in the art. As example of useful polymers, one can cite GGGGSGGGGSGGGGS ((G4S)3; SEQ ID NO:25), GSTSGSGKPGSGEGSTKG (CD19 linker; SEQ ID NO:26), GGSSRSSSSGGGGSGGGG (18mer; SEQ ID NO:27), GGGGSGGGGSGGGGSGGGGS ((G4S)4; SEQ ID NO:28), KESGSVSSEQLAQFRSLD (SEQ ID NO:29), EGKSSGSGSESKST (SEQ ID NO:30), GSAGSAAGSGEF (SEQ ID NO:31), GGGGGGGG (SEQ ID NO:32) or GGGGGG (SEQ ID NO:33). Finally, these scFv fragments can be obtained by methods well known to those skilled in the art, such as described by GILLILAND et al. (Tissue Antigens, vol. 47, pp. 1-20, 1996). The term "stalk region" also called as "spacer or hinge domain" as used herein refers to any oligo- or polypeptide that functions to link the transmembrane domain to the ectodomain. In particular, stalk region are used to provide more flexibility and accessibility for the ectodomain. The spacer elements play a predominantly structural role in the CAR. The spacer physically separates the targeting moiety from the T-cell membrane. The optimum distance required is likely to be different for each antigen. To enable efficient target access, a spacer appears to be required if a CAR binds an epitope that lies close to the target cell membrane, or when an antigen is complex in size and glycosylation status. Human IgG-derived spacers (Hinge-CH2-CH3) are commonly used due to their stabilizing action on CAR expression but interactions between the Fc domain of the spacer and Fc gamma receptors (FcgRs) on myeloid cells can lead to activation-induced cell death of T-cells and limited persistence in-vivo. This can be overcome by deleting or modifying regions of the constant heavy (CH)2 domain that are essential for FcgR binding thereby improving CAR T-cell persistence and anti-tumour activity in-vivo in pre-clinical models.

Other Hinge domains commonly used include those derivated from CD28 or CD8 or other truncated fragments from Human IgG-derived spacers. In a preferred embodiment, the CAR comprises a stalk region between the ectodomain and the transmembrane domain. A stalk region may comprise up to 300 amino acids, preferably 10 to 100 amino acids and most preferably 25 to 50 amino acids. This stalk region may be derived from all or part of naturally occurring molecules, such as part of the extracellular region of CD8, CD4 or CD28, or from all or part of an antibody constant region. Alternatively, this stalk region may be a synthetic sequence.

The transmembrane domain is a membrane anchor domain and also a linker between the ectodomain and the endomain. This transmembrane domain may be a human IgG4Fc hinge region, a Fc region, a CD4 transmembrane domain, a T cell receptor transmembrane, or other transmembrane domains from other human transmembrane signaling proteins, such as CD16, TCR Zeta chain (CD3), CD28 and CD8 and erythropoietin receptor, and mutants thereof. Preferably, this transmembrane domain is a T cell receptor transmembrane domain. Preferably, the T cell receptor transmembrane domain is issued from a transmembrane protein able to form a complex with the T cell receptor for antigen (TCR). Preferably, the T cell receptor transmembrane domain comprises part or all of one or more of TCR Zeta chain (CD3), CD28, OX40/CD134, 4-1BB/CD137/TNFRSF9, FcεRIγ, ICOS/CD278, ILRB/CD122, IL-2RG/CD132, CD27, DAP10 and CD40.

The endodomain is an intracellular signaling domain, which is responsible for intracellular signaling following the binding of the ectodomain to the target antigen resulting in the activation of the immune cell. In other word, the intracellular signaling domain is responsible for the activation of at least one of the normal effector functions of the immune cell in which the chimeric receptor is expressed. The term "effector function" refers to a specialized function of a T cell, which can be a cytolytic activity or helper activity including the secretion of cytokines. Thus the term "intracellular signaling domain" refers to the portion of a protein that transduces the effector function signal and directs the cell to perform a specialized function. While usually the entire intracellular signaling domain will be employed, in many cases it will not be necessary to use the entire intracellular polypeptide. To the extent that a truncated portion of the intracellular signaling domain may find use, such truncated portion may be used in place of the intact chain as long as it still transduces the effector function signal. The term intracellular signaling domain is thus meant to include any truncated portion of the intracellular signaling domain sufficient to transduce the effector function signal.

Preferred examples of signal transducing domain for use in multi-chain CAR can be the cytoplasmic sequences of the Fc receptor or T cell receptor and co-receptors that act in concert to initiate signal transduction following antigen receptor engagement, as well as any derivate or variant of these sequences and any synthetic sequence that as the same functional capability. Signal transduction domain comprises two distinct classes of cytoplasmic signaling sequence, those that initiate antigen-dependent primary activation, and those that act in an antigen-independent manner to provide a secondary or co-stimulatory signal. Primary cytoplasmic signaling sequence can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Examples of ITAM used in the invention can include as non limiting examples those derived from TCRzeta, FcRgamma, FcRbeta, FcRepsilon, CD3gamma, CD3delta, CD3epsilon, CD5, CD22, CD79a, CD79b and CD66d. In a preferred embodiment, the signaling transducing domain of the multi-chain CAR can comprise the CD3zeta signaling domain, or the intracytoplasmic domain of the Fc epsilon RI beta or gamma chains.

In particular embodiment the signal transduction domain of the multi-chain CAR of the present invention comprises a co-stimulatory signal molecule. A co-stimulatory molecule is a cell surface molecule other than an antigen receptor or their ligands that is required for an efficient immune response.

"Co-stimulatory ligand" refers to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatory ligand (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4), an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-IBB, OX40, CD30, CD40, PD-1, ICOS, DAP-10, lymphocyte function-associated antigen-1 (LFA-1), CD2, CD7, LTGHT, NKG2C, B7-H3, a ligand that specifically binds with CD83.

A "co-stimulatory molecule" refers to the cognate binding partner on a T-cell that specifically binds with a co-stimulatory ligand, thereby mediating a co-stimulatory response by the cell, such as, but not limited to proliferation. Co-stimulatory molecules include, but are not limited to an MHC class I molecule, BTLA and Toll ligand receptor. Examples of costimulatory molecules include CD27, CD28, CD8, 4-1BB (CD137), OX40, CD30, CD40, PD-1, ICOS, DAP-10, lymphocyte function-associated antigen-1 (LFA-1), CD2, CD7, LIGHT, NKG2C, B7-H3 and a ligand that specifically binds with CD83 and the like.

The term "derivative thereof" refers to an amino acid sequence having a percentage of identity of at least 90%, preferably at least 95%, most preferably at least 98% (i.e. corresponding to about 12, 6 and 2 amino acids substitutions respectively) with an amino acid sequence selected in the group comprising or consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50 and SEQ ID NO:51, preferably of at least 99% (i.e. corresponding to about 1 amino acid substitution).

When related to CDRs sequences, the term derivative thereof" refers to an amino acid sequence having a percentage of identity of at least 80%, and preferably at least 90% (i.e. corresponding to about 2, and 1 amino acids substitutions respectively) with an amino acid sequence selected in the group comprising or consisting of, SEQ ID NO:16, SEQ ID NO:17, SEQ ID NO:18, SEQ ID NO:19, SEQ ID NO:20, and SEQ ID NO:21.

Such derivatives can be simply identified by the skilled person in view of its personal knowledge and of the teaching of the present patent application. It will also be understood that natural amino acids may be replaced by chemically modified amino acids. Typically, such chemically modified amino acids increase the polypeptide half-life.

As used herein, "percentage of identity" between two amino acids sequences, means the percentage of identical amino-acids, between the two sequences to be compared, obtained with the best alignment of said sequences, this percentage being purely statistical and the differences between these two sequences being randomly spread over the amino acids sequences. As used herein, "best alignment" or "optimal alignment", means the alignment for which the determined percentage of identity (see below) is the highest. Sequences comparison between two amino acids sequences are usually realized by comparing these sequences that have been previously aligned according to the best alignment; this comparison is realized on segments of comparison in order to identify and compare the local regions of similarity. The best sequences alignment to perform comparison can be realized, beside by a manual way, by using the local homology algorithm developed by Smith and Waterman (Ad. App. Math., vol. 2, p: 482, 1981), by using the global homology algorithm developed by Neddleman and Wunsch (J. Mol. Biol., vol. 48, p: 443, 1970), by using the method of similarities developed by Pearson and Lipmolan (Proc. Natl. Acad. Sci. USA, vol. 85, p: 2444, 1988), by using computer softwares using such algorithms (GAP, BESTFIT, BLAST P, BLAST N, FASTA, TFASTA in the Wisconsin Genetics software Package, Genetics Computer Group, 575 Science Dr., Madison, Wis. USA), by using the MUSCLE multiple alignment algorithms (Edgar, Robert C., Nucleic Acids Research, vol. 32, p: 1792, 2004). To get the best local alignment, one can preferably use the BLAST software with the BLOSUM 62 matrix. The identity percentage between two sequences of amino acids is determined by comparing these two sequences optimally aligned, the amino acids sequences being able to encompass additions or deletions in respect to the reference sequence in order to get the optimal alignment between these two sequences. The percentage of identity is calculated by determining the number of identical position between these two sequences, and dividing this number by the total number of compared positions, and by multiplying the result obtained by 100 to get the percentage of identity between these two sequences.

The antibody used in the compositions of the invention is produced recombinantly.

The antibody used in the compositions of the invention may or may not be glycosylated, though glycosylated antibodies are preferred. In a preferred embodiment, the antibody used in the compositions of the invention may be low fucose.

The antibody used in the compositions of the invention may be an immunoconjugate.

As used herein, the term "immunoconjugate" refers to a conjugate molecule comprising at least one antibody, a functional fragment or derivative thereof, bound to a second molecule, preferably an immunomodulating agent, a cytotoxic agent or a radioisotope.

Such immunoconjugate may be Antibody Drug Conjugates (ADCs), Immunocytokines (ICK) or Antibody Radio Conjugates (ARC). Now, this second molecule may be an antibody having a binding specificity for another antigen, the formed immunoconjugate being a bispecific antibody such as BiTEs (Bi-specific T-cell engagers). Said antibody or fragment thereof is complexed or covalently bound (e.g. fusion protein) to said second molecule. Preferably, said antibody or fragment thereof is bound to said second molecule by covalent linkage. This second molecule may be a protein or a glycoprotein capable of specifically interacting with saccharides to form non-covalent bonds such as lectins.

The antibody used in the compositions of the invention may be bi-specific or multi-specific antibody. Several formats such as dual-variable domain immunoglobulins (DVDs), bispecific T-cell engagers (BiTEs), diabodies, tetravalent tandem antibodies (TandAbs) or dual affinity retargeting molecules (DART) are suitable format of antibody used in the compositions (WEIDLE et al., Cancer Genomics & Proteomics, 2013, vol. 10, pp. 1-18).

Preferably, when the patient is a human, the antibodies that are used in the treatment of cancer expressing OAcGD2 ganglioside are human or humanized (CDR-grafted) versions of antibodies; although murine versions of antibodies can be used. When considering repeated treatments, a human or humanized IgG antibody is less likely to generate an anti-IgG immune response from patients.

In all embodiments, the composition according to the present invention contains therapeutically effective amount of at least one anti-cancer agent and therapeutically effective amount the at least one antibody recognizing the OAcGD2 ganglioside, a functional fragment or a derivative thereof.

According to a preferred embodiment, the antibody, functional fragment or derivative thereof can be administered by injection at a dose comprised between 2 and 2,000 mg/m$^2$ of subject, preferably a dose comprised between 5 and 1,000 mg/m$^2$, and most preferably at a dose comprised between 10 and 500 mg/m$^2$.

Doses given herein are for humans, but can be adjusted to the size of other mammals, as well as children, in accordance with weight or square meter size.

As used herein, the term "therapeutically effective amount" is intended to encompass any amount that will achieve the desired therapeutic or biological effect. The therapeutic effect is dependent upon the cancer expressing the OAcGD2 ganglioside treated or the biological effect desired. As such, the therapeutic effect can be a decrease in the severity of symptoms associated with the cancer expressing the OAcGD2 ganglioside and/or inhibition (partial or complete) of progression of the cancer expressing the OAcGD2 ganglioside. The amount needed to elicit the therapeutic response can be determined based on cancer type, the age, health, size and sex of the patient.

Optimal amounts can also be determined based on monitoring of the patient's response to treatment.

In certain embodiments, the composition also comprises a pharmaceutically acceptable carrier for use in therapy.

The expression "pharmaceutically acceptable" refers to molecular entities and compositions that are physiologically tolerable and do not typically produce allergic or similar undesirable reactions, such as gastric upset, dizziness and the like when administered to a human. Preferably, as used herein, the expression "pharmaceutically acceptable" means approvable by a regulatory agency of the Federal or state government or listed in the U.S. Pharmacopeia or other generally recognized pharmacopeia for use in animals, and more particularly in humans.

The term "carrier" refers to a solvent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like.

Said composition may be in any pharmaceutical form suitable for administration to a patient, including but not limited to solutions, suspensions, lyophilized powders, capsule and tablets. Now, the route of administration of the composition of the invention is preferably parenteral; as used herein, the term "parenteral" includes intravenous, intramuscular, subcutaneous, intraperitoneal, rectal, vaginal, mucosal, intrathecal, intracranial, or intratumoral administration. Thus, the pharmaceutical composition contains vehicles which are pharmaceutically acceptable for a formulation intended to be injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. Suitable pharmaceutical carriers are described in "Remington's Pharmaceutical Sciences" by E. W. Martin.

Most preferably, the composition is in any pharmaceutical form suitable for intravenous administration to a patient.

The antibody, functional fragment or derivative of the invention may be solubilized in a buffer or water or incorporated in emulsions, microemulsions, hydrogels (e.g. PLGA-PEG-PLGA triblock copolymers-based hydrogels), in microspheres, in nanospheres, in microparticles, in nanoparticles (e.g. poly(lactic-co-glycolic acid) microparticles (e.g. poly lactic acid (PLA); poly (lactide-co-glycolic acid) (PLGA); polyglutamate microspheres, nanospheres, microparticles or nanoparticles), in liposomes, or other galenic formulations. In all cases, the formulation must be sterile and fluid to the extent of acceptable syringability. It must be stable under the conditions of manufacture and storage and must be preserved against the contaminating action of microorganisms, such as bacteria and fungi.

Dispersions can also be prepared in glycerol, liquid polyethylene glycols, and mixtures thereof and in oils. Under ordinary conditions of storage and use, these preparations contain a preservative to prevent the growth of microorganisms.

The antibody, functional fragment or derivative of the invention can be formulated into a composition in a neutral or salt form. Pharmaceutically acceptable salts include the acid addition salts (formed with the free amino groups of the protein) which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or a dispersion medium containing, for example, water, ethanol, polyol (for example, glycerol, propylene glycol, and liquid polyethylene glycol, and the like), suitable mixtures thereof, and vegetables oils. The antibodies of the invention may also be modified, by pegylation as an example, so as to increase its biodisponibility.

The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride.

Prolonged absorption of the injectable compositions can be brought about by the use in the compositions of agents delaying absorption, for example, aluminium monostearate, gelatin, polyols, and half-life enhancing covalent and noncovalent formulations.

There are numerous causes of peptide instability or degradation, including hydrolysis and denaturation. Hydrophobic interaction may cause clumping of molecules together (i.e. aggregation). Stabilizers may be added to reduce or prevent such problems.

Stabilizers include cyclodextrine and derivatives thereof (see U.S. Pat. No. 5,730,969). Suitable preservatives such as sucrose, mannitol, sorbitol, trehalose, dextran and glycerin can also be added to stabilize the final formulation. A stabilizer selected from ionic and non-ionic surfactants, D-glucose, D-galactose, D-xylose, D-galacturonic acid, trehalose, dextrans, hydroxyethyl starches, and mixtures thereof may be added to the formulation. Addition of alkali metal salt or magnesium chloride may stabilize a peptide. The peptide may also be stabilized by contacting it with a saccharide selected from the group consisting of dextran, chondroitin sulphuric acid, starch, glycogen, dextrin, and alginic acid salt. Other sugars that can be added include monosaccharides, disaccharides, sugar alcohols, and mixtures thereof (E.g., glucose, mannose, galactose, fructose, sucrose, maltose, lactose, mannitol, xylitol). Polyols may stabilize a peptide, and are water-miscible or water-soluble. Suitable polyols may be polyhydroxy alcohols, monosaccharides and disaccharides including mannitol, glycerol, ethylene glycol, propylene glycol, trimethyl glycol, vinyl pyrrolidone, glucose, fructose, arabinose, mannose, maltose, sucrose, and polymers thereof. Various excipients may also stabilize peptides, including serum albumin, amino acids, heparin, fatty acids and phospholipids, surfactants, metals, polyols, reducing agents, metal chelating agents, polyvinyl pyrrolidone, hydrolysed gelatin, and ammonium sulfate.

In all embodiments, the at least one anti-cancer agent having a molecular mass ranging from 100 Daltons to 200,000 Daltons, and the at least one antibody recognizing the OAcGD2 ganglioside, a functional fragment or a derivative thereof may be administered separately, simultaneously or sequentially.

In certain embodiments, the at least one anti-cancer agent administered separately, simultaneously or sequentially with the at least one antibody recognizing the OAcGD2 ganglioside, a functional fragment or a derivative has a molecular mass ranging from 10 kDa to 15 kDa.

Also in certain embodiments, the at least one anti-cancer agent administered separately, simultaneously or sequentially with the at least one antibody recognizing the OAcGD2 ganglioside, a functional fragment or a derivative has a molecular mass ranging from 80 kDa to 200 kDa.

Also in certain embodiments, the at least one anti-cancer agent administered separately, simultaneously or sequentially with the at least one antibody recognizing the OAcGD2 ganglioside, a functional fragment or a derivative has a molecular mass ranging from 120 to 800 Daltons.

For example, the at least one antibody recognizing the OAcGD2 ganglioside, a functional fragment or a derivative thereof may be administered previously to the administration of the at least one anti-cancer agent having a molecular mass ranging from 100 Daltons to 200,000 Daltons. The way and the sequence of administration aim to obtain the maximum effectiveness of the combination; it is possible for each administration to have a variable duration ranging from a rapid total administration to a continuous infusion. As a consequence, the combination of at least one anti-cancer agent having a molecular mass ranging from 100 Daltons to 200,000 Daltons, and at least one antibody recognizing the OAcGD2 ganglioside, a functional fragment or a derivative thereof are not limited to those which are obtained by physical association of them, but also to those which allow a separate administration that can be simultaneous or sequential.

In certain embodiments, the pharmaceutical composition also comprises a second, a third, a fourth, a $n^{th}$ anti-cancer agent including, but not limited to, alkylating agents, anti-metabolites, anti-tumor antibodies, anti-tumor antibiotics, topoisomerase inhibitors, mitotic inhibitors, tyrosine kinase inhibitors, corticosteroids, hormones or hormone-like drugs, cytokines, nucleoside analogs, etc.

Examples of other anti-cancer agents that may be combined with a composition comprising: (i) at least one anti-cancer agent having a molecular mass ranging from 100 Daltons to 200,000 Daltons, (ii) at least one antibody recognizing the OAcGD2 ganglioside, a functional fragment or a derivative thereof, and optionally (iii) a pharmaceutically acceptable carrier, for use in a method for the treatment and/or prevention of cancer expressing the OAcGD2 ganglioside, either administered separately or in the same compositions, include, but are not limited to:

(a) alkylating agents: mechloramine, chlorambucil, ifosfamide, melphalan and the likes,
(b) anti-metabolites: 6-mercaptopurine (6-MP), capecitabine, cytarabine, floxuridine, fludarabine, gemcitabine, hydroxyurea, methotrexate, pemetrexed and the likes,
(c) anti-tumor antibiotics: actinomycin-D, bleomycin, mitomycin-C, mitoxanthrone and the likes,
(d) topoisomerase inhibitors: etoposide (VP-16), teniposide and the likes,
(e) mitotic inhibitors: paclitaxel, docetaxel and the likes,
(f) tyrosine kinase inhibitors: imatinib, gefininib, sunitinib and the likes,
(g) corticosteroids: prednisone, methylprednisone, dexamethasone and the likes,
(h) hormones or hormone-like drugs: fulvestrant, tamoxifen, toremifene, anastrozole, exemestane, letrozole, megestrol acetate, estrogens, bicalutamide, flutamide, nilutamide, leuprolide, goserelin and the likes,
(i) cytokine: a soluble small protein of approximately 5-20 kDa that is released by one cell population (e.g., primed T-lymphocytes) on contact with specific antigens, and which acts as an intercellular mediator between cells. Examples of cytokines include lymphokines, monokines, interleukins, and several related signaling molecules, such as tumor necrosis factor (TNF) and interferons,
(j) nucleoside analogs: cladribine, fludarabine, pentostatin and the likes.

In certain embodiments, the pharmaceutical composition also comprises a second, a third, a fourth, a $n^{th}$ anti-cancer agent including, but not limited to nucleic acids, such double-stranded synthetic short RNA molecules (miRNAs) or synthetic DNA/RNA-like oligonucleotides (ASOs). MicroRNAs (miRNAs) are endogenous single stranded non-coding RNAs ranging from 16 to 25 nucleotides involved in post-transcriptional attenuation of mRNA translation. Their deregulation is frequently observed in many diseases, including cancer. The importance of mir-34 family and mir-17-92 cluster has been established for both tumorigenesis and metastasis in neuroblastoma, whereas overexpression of mir-184 reduces neuroblastoma tumor growth (Chu and Lee, 2012, Intech, MicroRNA target signatures in Advanced stage Neuroblastoma, Neuroblastoma—Present and future, Prof. Hiroyuki Shimada, IBSN 978-953-307-016-2, chapter 13, pp. 271-286). Thus, by designing different types of small single or double stranded, chemically-synthesized and optimized nucleic acids (from about 22 nucleotides) such as miRNA mimics or agomirs that up-regulate miRNA activity, miRNA inhibitors or antagomir that knockdown individual miRNA molecules, it is possible to control specific miRNA activity or to tightly regulate miRNA cellular levels in cells. Such short chemically-synthesized nucleic acids targeting miRNA involved in cancer expressing the OAcGD2 ganglioside can be used in the compositions according to the invention.

A second aspect of the present invention concerns a method of increasing the efficacy of a cancer expressing the OAcGD2 ganglioside treatment comprising an anti-cancer agent, comprising administering to a patient in need thereof an effective amount of a composition comprising: (i) at least one anti-cancer agent having a molecular mass ranging from 100 Daltons to 200,000 Daltons, (ii) at least one antibody recognizing the OAcGD2 ganglioside, a functional fragment or a derivative thereof, and optionally (iii) a pharmaceutically acceptable carrier.

In certain embodiments, in the composition used in the method of increasing the efficacy of a cancer expressing the OAcGD2 ganglioside treatment, the at least one anti-cancer agent has a molecular mass ranging from 10 kDa to 15 kDa.

Also in certain embodiments, in the composition used in the method of increasing the efficacy of a cancer expressing the OAcGD2 ganglioside treatment, the at least one anti-cancer agent has a molecular mass ranging from 80 kDa to 200 kDa.

Also in certain embodiments, in the composition used in the method of increasing the efficacy of a cancer expressing the OAcGD2 ganglioside treatment, the at least one anti-cancer agent has a molecular mass ranging from 120 to 800 Daltons.

The expression "increasing the efficacy of a treatment" refers to an increase in the number of cancer cells death obtained by the method of the invention compared to a treatment using the sole anti-cancer agent.

The effectiveness of anti-cancer agents having a molecular mass ranging from 100 Daltons to 200,000 Daltons can be considerably improved when they are administered in combination with at least one antibody recognizing the OAcGD2 ganglioside, a functional fragment or a derivative thereof in anticancer treatments which has a mechanism of action different than that of anti-cancer agents having a molecular mass ranging from 100 Daltons to 200,000 Daltons.

The improved effectiveness of a combination according to the invention can be demonstrated by determining the therapeutic synergism. A clear and well-accepted definition of "synergism" is: it represents greater effects for drugs in combination than the simple additive effect expected from the knowledge of the effects of each drug individually. A possible favorable outcome for synergism may be increasing the efficacy of the therapeutic effect. Preferably, the cancer expressing OAcGD2 ganglioside is treated more effectively when using the composition of the invention.

The effectiveness of a combination of at least one anti-cancer agents having a molecular mass ranging from 100 Daltons to 200,000 Daltons, and at least one antibody recognizing the OAcGD2 ganglioside, a functional fragment or a derivative thereof can be interpreted from measured experimental data using the Combination Index (CI) approach developed by Chou and Talalay (Chou T C, Pharmacol Rev 58:621-681, 2006). Briefly, for the combination of two drugs $(D)_1$ and $(D)_2$ at the combination ratio of $(D)_1:(D)_2=P:Q$, in the combination, $(D)_{1,2}=(D)_1+(D)_2$, we get $(D)_1=(D)_{1,2}\times[P/(P+Q)]$ and $(D)_2=(D)_{1,2}\times[Q/(P+Q)]$. The combination index equation $CI_x=[(D)_2/(D_x)_1]+[(D)_2/(D_x)_2]$ indicates that for a given effect of $(F_a)_x$ for x % inhibition of system, $D_x$, the combined additive effect for the sum of the fractional doses of each drug, $(D)_2/(D_x)_1$ and $(D)_2/(D_x)_2$ should be equal to unity. CI=1, it indicates an additive effect, CI<1, it indicates a synergistic effect, and CI>1, it indicates an antagonistic effect. The effectiveness of the combinations on solid tumors can also be determined experimentally by, for example, comparing the number of tumor size before and after treatment. Preferably, the combinations of at least one anti-cancer agent having a molecular mass ranging from 100 Daltons to 200,000 Daltons, and at least one antibody recognizing the OAcGD2 ganglioside, a functional fragment or a derivative thereof as disclosed herein are effective when tumor size is reduced by at least 5%, at least 10%, at least 20%, at least 30%, at least 40%, at least 50%, at least 60%, at least 70%, at least 80%, at least 90%, 100%, and more preferably at least 50 to 70%.

The effectiveness of the combinations on solid tumors can also be determined by, for example, following up of the number of cancer cells, cancer cell infiltration into peripheral organs, or tumors metastasis.

Cancer therapy efficacy can also be measured by assessing duration of survival of patient suffering from a cancer expressing the OAcGD2 ganglioside, duration of progression free survival (PFS), the response rate (RR), the duration of the response and/or quality of life.

In preferred embodiments, the at least one anti-cancer agent having a molecular mass ranging from 100 Daltons to 200,000 Daltons of the composition according to the invention is the same than that initially selected for treating cancer expressing OAcGD2 ganglioside as single agent.

Another possible favorable outcome for synergism may be decreasing the dosage of the at least one anti-cancer agent but increasing or maintaining the same efficacy to avoid toxicity.

A third aspect of the present invention concerns a method of increasing sensitivity to an anti-cancer agent in a patient suffering from a cancer expressing the OAcGD2 ganglioside, comprising administering to a patient in need thereof an effective amount of a composition comprising: (i) at least one anti-cancer agent having a molecular mass ranging from 100 Daltons to 200,000 Daltons, (ii) at least one antibody recognizing the OAcGD2 ganglioside, a functional fragment or a derivative thereof, and optionally (iii) a pharmaceutically acceptable carrier.

In certain embodiments, in the composition used in the method of increasing the sensitivity to an anti-cancer agent in a patient suffering from a cancer expressing the OAcGD2 ganglioside, the at least one anti-cancer agent has a molecular mass ranging from 10 kDa to 15 kDa.

Also in certain embodiments, in the composition used in the method of increasing the sensitivity to an anti-cancer agent in a patient suffering from a cancer expressing the OAcGD2 ganglioside, the at least one anti-cancer agent has a molecular mass ranging from 80 kDa to 200 kDa.

Also in certain embodiments, in the composition used in the method of increasing the sensitivity to an anti-cancer agent in a patient suffering from a cancer expressing the OAcGD2 ganglioside, the at least one anti-cancer agent has a molecular mass ranging from 120 to 800 Daltons.

In addition to providing improved treatment for cancer, administration of certain combinations described herein may improve the quality of life for a patient compared to the quality of life experienced by the same patient receiving a different treatment. For example, administration of a combination of the at least one antibody recognizing the OAcGD2 ganglioside, a functional fragment or a derivative thereof and the anti-cancer agent, as described herein to a patient in need thereof may provide an improved quality of life compared to the quality of life the same patient would experience if they received only anti-cancer agent as therapy. For example, the combined therapy with the combination described herein may lower the dose of anti-cancer agent needed, thereby lessening the side-effects associated with the therapeutic (e.g. nausea, vomiting, hair loss, rash, decreased appetite, etc.). The combination may also cause reduced tumor burden and the associated adverse events, such as pain, organ dysfunction, weight loss, etc.

Another possible favorable outcome for synergism may be minimizing or slowing down the development of drug resistance and its dramatic consequence, a recurrence of the cancer expressing the OAcGD2 ganglioside.

A fourth aspect of the present invention concerns a method of preventing or delaying development of cancer resistant to an anti-cancer agent in a patient suffering from a cancer expressing the OAcGD2 ganglioside, comprising administering to a patient in need thereof an effective amount of a composition comprising: (i) at least one anti-cancer agent having a molecular mass ranging from 100 Daltons to 200,000 Daltons, (ii) at least one antibody recognizing the OAcGD2 ganglioside, a functional fragment or a derivative thereof, and optionally (iii) a pharmaceutically acceptable carrier.

In certain embodiments, in the composition used in the method of preventing or delaying development of cancer resistant to an anti-cancer agent in a patient suffering from a cancer expressing the OAcGD2 ganglioside, the at least one anti-cancer agent has a molecular mass ranging from 10 kDa to 15 kDa.

Also in certain embodiments, in the composition used in the method of preventing or delaying development of cancer resistant to an anti-cancer agent in a patient suffering from a cancer expressing the OAcGD2 ganglioside, the at least one anti-cancer agent has a molecular mass ranging from 80 kDa to 200 kDa.

Also in certain embodiments, in the composition used in the method of preventing or delaying development of cancer resistant to an anti-cancer agent in a patient suffering from a cancer expressing the OAcGD2 ganglioside, the at least one anti-cancer agent has a molecular mass ranging from 120 to 800 Daltons.

It is not unusual that after primary treatment (i.e. first line cancer treatment) for a cancer with a single anti-cancer agent, the patient survives without any signs or symptoms of that cancer for a short period of time before the return of the cancer or the signs and symptoms of the cancer. By using the combination of at least one anti-cancer agent having a molecular mass ranging from 100 Daltons to 200,000 Daltons, (ii) at least one antibody recognizing the OAcGD2 ganglioside, a functional fragment or a derivative thereof, the aim is to prevent clonal selection leading to resistant cells grow out.

In a preferred embodiment, the at least one anti-cancer agent having a molecular mass ranging from 100 Daltons to 200,000 Daltons of the composition according to the invention is different from that at the origin of the resistance of cancer.

Mechanisms of therapeutic resistance include increased recognition and repair of DNA damaged by the anti-cancer agent, altered cell cycle checkpoint control, impaired functioning of apoptotic pathways, and reduced drug accumulation as a result of increased expression of ABC transporters that efflux anti-cancer agents. Evidence has emerged that Cancer Stem Cells (CSCs) represent a subpopulation of cells within cancers that is characterized by increased resistance to chemo- and radiotherapy, indicating that conventional anticancer approaches might frequently fail to eradicate the cell subset that initiates and perpetuates tumorigenesis. Now, cancer cells other than CSCs may develop increased resistance to chemo- and radiotherapy, potentially by using similar pathway. Reversing chemoresistance can be achieved through specific blockade of multidrug resistance ABC transporters, as shown in human melanoma.

Surprisingly, the inventors identified a new method for reversing chemoresistance, notably in CSC populations, without needing interfering with multidrug resistance transporters or shuttles involved in anti-cancer agent intake.

This fourth aspect of the present invention also concerns a method of treating a refractory or relapsed cancer in a patient suffering from a cancer expressing the OAcGD2 ganglioside, comprising administering to a patient in need thereof an effective amount of a composition comprising: (i) at least one anti-cancer agent having a molecular mass ranging from 100 Daltons to 200,000 Daltons, (ii) at least one antibody recognizing the OAcGD2 ganglioside, a functional fragment or a derivative thereof, wherein said cancer is refractory to or is in relapse after a first line cancer treatment comprising one or more anti-cancer agent selected from the group consisting of alkylating agents, antimetabolites, anti-tumor antibiotics, topoisomerase inhibitors, mitotic inhibitors, tyrosine kinase inhibitors and nucleoside analogs.

This fourth aspect of the present invention also concerns a composition comprising: (i) at least one anti-cancer agent having a molecular mass ranging from 100 Daltons to 200,000 Daltons, (ii) at least one antibody recognizing the OAcGD2 ganglioside, a functional fragment or a derivative thereof, for use in the treatment of refractory or relapsed cancer in a patient suffering from a cancer expressing the OAcGD2 ganglioside, wherein said cancer is refractory to or is in relapse after a first line cancer treatment comprising one or more anti-cancer agent selected from the group consisting of alkylating agents, antimetabolites, anti-tumor antibiotics, topoisomerase inhibitors, mitotic inhibitors, tyrosine kinase inhibitors and nucleoside analogs.

In certain embodiments, in the composition used in the method of treating a refractory or relapsed cancer in a patient suffering from a cancer expressing the OAcGD2 ganglioside, the at least one anti-cancer agent has a molecular mass ranging from 10 kDa to 15 kDa.

Also in certain embodiments, in the composition used in the method of treating a refractory or relapsed cancer in a patient suffering from a cancer expressing the OAcGD2 ganglioside, the at least one anti-cancer agent has a molecular mass ranging from 80 kDa to 200 kDa.

Also in certain embodiments, in the composition used in the method of treating a refractory or relapsed cancer in a patient suffering from a cancer expressing the OAcGD2 ganglioside, the at least one anti-cancer agent has a molecular mass ranging from 120 to 800 Daltons.

Also in certain embodiments, the refractory or relapsed cancer is neuroblastoma.

According to another preferred embodiment, when the composition is used in a method of treating refractory or relapsed neuroblastoma, the at least one anti-cancer agent is temozolomide, topotecan, irinotecan, cyclophosphamide, fudarabine, cisplatin, doxorubicin, isotretinoin, etoposide or a mixture thereof.

Also in certain embodiments, the refractory or relapsed cancer is glioblastoma.

According to another preferred embodiment, when the composition is used in a method of treating refractory or relapsed glioblastoma, the at least one anti-cancer agent is temozolomide, topotecan, irinotecan, cyclophosphamide, fludarabine, cisplatin, carboplatin or a mixture thereof.

In preferred embodiments, the at least one anti-cancer agent having a molecular mass ranging from 100 Daltons to 200,000 Daltons of the composition used in the method of treating a refractory or relapsed cancer is the same from that used in the first line cancer treatment.

Another possible favorable outcome for synergism may be providing synergistic combination relying on a balance between synergism and cell toxicity.

A fifth aspect of the present invention concerns an in vitro/ex vivo method of identifying synergistic combination of at least one anti-cancer agent having a molecular mass ranging from 100 Daltons to 200,000 Daltons, and (ii) at least one antibody recognizing the OAcGD2 ganglioside, a functional fragment or a derivative thereof comprising the steps of:
  a) incubating primary tumor cells or cancer cell lines cells expressing the 0-acetylated form of GD2 ganglioside in vitro with a composition comprising at least (i) one anti-cancer agent having a molecular mass ranging from 100 Daltons to 200,000 Daltons, and (ii) at least one antibody recognizing the OAcGD2 ganglioside, a functional fragment or a derivative thereof, and
  b) measuring the CI50 index according to the method as disclosed by Chou and Talalay, wherein a CI50 below 1 is indicative of synergism.

Primary tumor cells are for example explanted human tumor cells. Any derivatives of these cells can give rise, for example to cancer cell lines.

In certain embodiments, in the synergistic combination identified by the in vitro/ex vivo method of the invention, the at least one anti-cancer agent has a molecular mass ranging from 10 kDa to 15 kDa.

Also in certain embodiments, in the synergistic combination identified by the in vitro/ex vivo method of the invention, the at least one anti-cancer agent has a molecular mass ranging from 80 kDa to 200 kDa.

Also in certain embodiments, in the synergistic combination identified by the in vitro/ex vivo method of the invention, the at least one anti-cancer agent has a molecular mass ranging from 120 to 800 Daltons.

A sixth aspect of the present invention concerns a kit for in vitro screening of synergistic combination of at least one anti-cancer agent having a molecular mass ranging from 100 Daltons to 200,000 Daltons, and (ii) at least one antibody recognizing the OAcGD2 ganglioside, a functional fragment or a derivative thereof.

In certain embodiments, in the kit for in vitro screening of synergistic combination of the invention, the at least one anti-cancer agent has a molecular mass ranging from 10 kDa to 15 kDa.

Also in certain embodiments, in the kit for in vitro screening of synergistic combination of the invention, the at least one anti-cancer agent has a molecular mass ranging from 80 kDa to 200 kDa.

Also in certain embodiments, in the kit for in vitro screening of synergistic combination of the invention, the at least one anti-cancer agent has a molecular mass ranging from 120 to 800 Daltons.

A seventh aspect of the present invention concerns a kit suitable for treating cancer expressing OAcGD2 ganglioside. In all embodiments, said kit comprises (i) at least one anti-cancer agent having a molecular mass ranging from 100 Daltons to 200,000 Daltons, and (ii) at least one antibody recognizing the OAcGD2 ganglioside, a functional fragment or a derivative thereof, and optionally (iii) a pharmaceutically acceptable carrier.

In certain embodiments, in the kit suitable for treating cancer expressing OAcGD2 ganglioside of the invention, the at least one anti-cancer agent has a molecular mass ranging from 10 kDa to 15 kDa.

Also in certain embodiments, in the kit suitable for treating cancer expressing OAcGD2 ganglioside of the invention, the at least one anti-cancer agent has a molecular mass ranging from 80 kDa to 200 kDa.

Also in certain embodiments, in the kit suitable for treating cancer expressing OAcGD2 ganglioside of the invention, the at least one anti-cancer agent has a molecular mass ranging from 120 to 800 Daltons.

A device capable of delivering the kit components through specific chosen route of administration may also be included.

The kit components may be packaged together or separated into two or more containers. In some embodiments, the containers may be vials that contain sterile, lyophilized formulations of a composition that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and maintained sterilely within the containers. Another component that can be included is instructions to a person using a kit for its use.

The antibody recognizing the OAcGD2 ganglioside, a functional fragment or a derivative thereof, is useful as adjuvant in anti-tumor therapy.

A height aspect of the present invention concerns the use of an antibody recognizing the OAcGD2 ganglioside, a functional fragment or a derivative thereof, for enhancing intracellular uptake of an anti-cancer agent having a molecular mass ranging from 100 Daltons to 200,000 Daltons in a cell expressing the O-acetylated form of GD2 ganglioside.

In certain embodiments, the antibody recognizing the OAcGD2 ganglioside, a functional fragment or a derivative thereof, is used for enhancing intracellular uptake of an anti-cancer agent having a molecular mass ranging from 10 kDa to 15 kDa.

Also in certain embodiments, the antibody recognizing the OAcGD2 ganglioside, a functional fragment or a derivative thereof, is used for enhancing intracellular uptake of an anti-cancer agent having a molecular mass ranging from 80 kDa to 200 kDa.

Also in certain embodiments, the antibody recognizing the OAcGD2 ganglioside, a functional fragment or a derivative thereof, is used for enhancing intracellular uptake of an anti-cancer agent having a molecular mass ranging from 120 to 800 Daltons.

The following examples are provided in order to demonstrate and further illustrate certain preferred embodiments and aspects of the present invention and are not to be construed as limiting the scope thereof.

EXAMPLES

1. Treatment of Neuroblastoma and Glioblastoma Cells with Anti-OAcGD2 mAb 8B6 Induces Pore Formation within Cell Membrane Culture dishes (6 wells) were coated with 500 000 IMR5, LAN-1 or DUASOII cells/well 24 hours before incubation with anti-OAcGD2 mAb 8B6 (murine, IgG3) or an isotype-matched negative control mouse IgG3 (CTRL−). Then, 40 µg/ml of antibodies were added to each well for 30 minutes. Supernatant was spinning down and cells were detached from their support using mechanical strength (without trypsin) and spin down. After being washed with PBS, cells were fixed with glutaraldehyde 2% in 0.1 mol/L sodium phosphate buffer, pH7.4, for 1 h at 4° C. Fixation was pursued with 1% OsO4 for 15 minutes. Deshydratation occurred in ethyl alcohol baths using 25%, 50%, 75% and 100% ethyl alcohol for 15 minutes each bath. Finally, cells were mounted onto metallic stub and analyzed by scanning electron microscopy.

Figure 2:
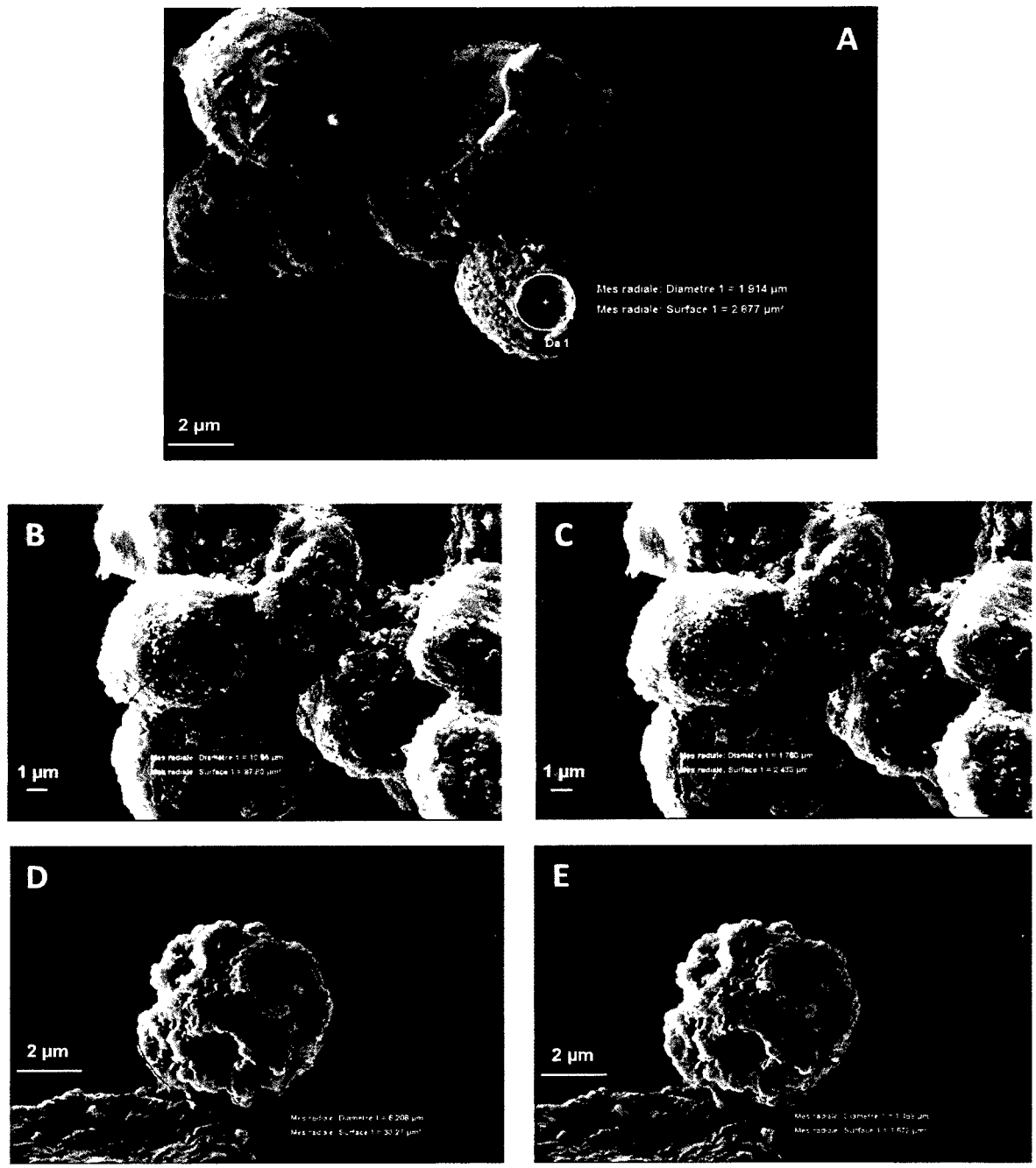
FIG. 2: Measurement of diameter and surface of cell and pore was performed on neuroblastoma cell lines and glioblastoma primary cells incubated with 40 µg/ml of anti-OAcGD2 mAb 8B6 for 30 minutes: IMR5 (panel A), LAN-1 (panels B and C) and DUASOII (panels D and E) cells. Magnifications are respectively of 5.02 K× (panel A), 4.5 K× (panels B and C) and 7.5 K× (panels D and E).

As shown in FIG. 1, the pore formation in the membrane of IMR5 (panel B), LAN-1 (panel D) and DUASOII (panel F) cells appears from 30 minutes of treatment with mAb 8B6. Cell and pore size and diameter were determined for the three cell types. As shown in FIG. 2-A, diameter of the pore induced by mAb 8B6 in IMR5 is about 1.914 µm and its surface is about 2.877 µm$^2$. In this case, the pore covers at least 4% of the total surface of the cell. The results obtained for LAN-1 and DUASOII are quite similar. As shown in FIGS. 2-B and 2-C, diameter of the pore induced by mAb 8B6 in LAN-1 is about 1.760 µm and its surface is about 2.433 µm$^2$. In this case, the pore covers at least 0.7% of the total surface of the cell. As shown in FIGS. 2-D and 2-E, diameter of the pore induced by mAb 8B6 in DUASOII is about 1.459 µm and its surface is about 1.672 µm$^2$. In this case, the pores cover at least 2.8% of the total surface of the cell.

Moreover, the inventors established that a smaller antibody concentration induces an increased penetration of propidium iodure.

2. Treatment with Either Isotretinoin, Topotecan or Doxorubicin does not Affect OAcGD2 Expression on Neuroblastoma Cell Lines We have reported earlier the expression of OAcGD2 in neuroblastoma cell lines (Alvarez-Rueda et al., PLos One 2011 6:e25220). Previous studies showed that GD2 expression—the precursor of OAcGD2—can be altered in neuroblastoma cells upon exposure to retinoic acid (Rebhan et al., Neuroreport. 1994 Apr. 14; 5(8):941-4 and Hettmer et al., Br J Cancer. 2004 Jul. 19; 91(2): 389-397). Thus, we tested if anti-cancer agent exposures would affect the level of mAb 8B6 binding. To this end, we treated the studied murine and human neuroblastoma cell lines with each single agent for 48 hours before studying OAcGD2-expression by flow cytometry analysis. The concentrations of drugs used in these experiments are indicated in the Table 1.

TABLE 1

Drugs concentrations used to treat neuroblastoma cell lines.

| Cell lines | Drug name | Concentration used (µM) |
|---|---|---|
| NXS2 Murine neuroblastoma cell line | Isotretinoin Topotecan Doxorubicin | 75 0.5 3 |
| IMR5 Human neuroblastoma cell line | Isotretinoin Topotecan Doxorubicin | 40 1 7 |
| LAN-1 Human neuroblastoma cell line | Isotretinoin Topotecan Doxorubicin | 40 5 3 |

TABLE 1-continued

Drugs concentrations used to treat neuroblastoma cell lines.

| Cell lines | Drug name | Concentration used (µM) |
|---|---|---|
| LAN-5 Human neuroblastoma cell line | Isotretinoin Topotecan Doxorubicin | 8 1 5 |

Analysis of cell surface OAcGD2-expression on neuroblastoma cell lines was evaluated by indirect immunofluorescence measured by flow cytometry. We incubated 5×10$^5$ cells in 96-well microplates with either mAb 8B6 (Cerato et al., Hybridoma 1997, 16:307-316) or mAb 7H2 (mouse monoclonal against O-acetyl GD3 was used as a negative control antibody) at 10 µg/ml for 60 minutes at 4° C. in PBS 1%-BSA. Antibody binding was analyzed after reaction with the fluorescein-isothiocyanate conjugated F(ab')2 fragment of goat anti-mouse IgG (VH+VL) as a second antibody (Jackson, Immunoresearch, Soham, UK) for 60 min at 4*C. Cell fluorescence was analyzed using a FACSCalibur™ flow cytometer (BD Biosciences, San Jose, Calif., USA) and Cell Quest™ Pro software (BD Biosciences). Relative fluorescence intensities of 10,000 cells were recorded as single-parameter histograms (log scale, 1024 channels, and 4 decades) and mean fluorescence intensity (MFI) was calculated for each histogram. Results were expressed as a MFI ratio calculated by dividing the flow cytometric MFI value of cells stained with antigen-specific mAb by the MFI value for the same cells stained with negative control mAb 7H2.

This approach allows for comparison of multiple test samples within a group and between different groups.

As shown in Table 2, the level of mAb 8B6 binding on NXS2 cells remained unchanged after 48 hours of incubation with isotretinoin, topotecan, or doxorubicin as compared to untreated cells.

We also observed little or no change when we studied the level of mAb 8B6 binding on IMR5, LAN-1 and LAN-S cells 48 hours after drug incubations (Table 2).

TABLE 2

Expression level of OAcGD2 in neuroblastoma cell lines after 48 hours exposure to anti-cancer agents[a]

| Cell lines | Control[b] | Isotretinoin[c] | Topotecan[c] | Doxorubicin[c] |
|---|---|---|---|---|
| NXS2 | 7.3 ± 0.9 | 7.5 ± 1.1 | 7.2 ± 1.4 | 6.48 ± 2.28 |
| IMR5 | 14.6 ± 0.4 | 19.2 ± 0.8 | 15.8 ± 2.3 | 15.24 ± 0.21 |
| LAN-1 | 12.1 ± 0.1 | 12.0 ± 0.1 | 9.6 ± 0.4 | 13.76 ± 1.8 |
| LAN-5 | 13.2 ± 0.7 | 16.8 ± 0.7 | 16.5 ± 1.2 | 14.36 ± 1.4 |

[a]The geometric mean fluorescence intensities (MFIs) of tumor cells stained with anti-OAcGD2 mAb 8B6 were normalized to the MFIs of tumor cells stained with the mAb 7H2-control antibody. Data are indicated as mean ± SD (n = 3).
[b]Untreated cells.
[c]The anti-cancer agent concentrations used in these experiments are indicated in Table 1.

3. Anti-OAcGD2 mAb 8B6 Shows Synergistic Effect with Chemotherapeutic Drugs in Neuroblastoma Cell Lines To test whether anti-OAcGD2 mAb 8B6 could enhance chemotherapy, we next characterized the effects on tumor cell viability of mAb 8B6 in combination with isotretinoin, topotecan and doxorubicin in four different neuroblastoma cell lines.

The antiproliferative activity of the anti-cancer agents was evaluated using the MIT Cell Proliferation Assay Kit (Roche Diagnostic, Indianapolis, USA). The MTT assay is based on the reduction of yellow tetrazolium MTT (3-(4,5-dimethyl-thiazolyl-2)-2,5-diphenyltetrazolium bromide) by metabolically active cells forming purple formazan crystals. The purple formazan is solubilized with detergent and quantified spectrophotometrically at 570 nm.

Cells in the log phase of growth were seeded into 96-well ($5\times10^3$ for LAN-1 and NXS2 cells; $1\times10^4$ for IMR5 and LAN-5 cells) treated plates in 100 μl of complete media. The cells were allowed to attach during an overnight incubation prior to treating with test agents. Test agents were serially diluted in complete culture media and added to each well in a volume of 50/65 μl for a total final volume of 165 μl/well. Equivalent culture media volume was added to control wells. Three conditions were used: anti-cancer agent alone, mAb 8B6 alone, mAb 8B6+anti-cancer agent. Cells were exposed to test agents for 48 hours. Following the exposure to test agents, 15 μl of MIT reagent was added to each well. The plates were returned to the incubator for four hours. Following the incubation period, kit supplied detergent reagent (100 μl) was added to all wells. The plates were wrapped in plastic wrap to prevent evaporation and allowed to sit at room temperature in the dark overnight. The absorbance at 570 nm was measured the following day using a iMark™ Microplate Absorbance Reader plate reader (Bio-Rad). Assays were performed in quadruplicate and experiments were repeated three times. Absorbance values were converted to Percent of Control and plotted against test agent concentrations for half maximal effective concentration (EC50) calculations using CompuSyn® software (ComboSyn, Paramus, N.J., USA). CompuSyn® is a computer software for PCs developed by Chou and Martin (2005, CompuSyn for Drug Combinations: PC Software and User's Guide: A Computer Program for Quantitation of Synergism and Antagonism in Drug Combinations, and the Determination of IC50 and ED50 and LD50 Values. ComboSyn, Paramus, N.J.) that can be used for dose effect analysis for single drugs using the median-effect equation and for multiple drug combinations using both the median-effect equation and the combination index equation. The median-effect equation used by CompuSyn® software derived from the mass-action law principle at equilibrium steady state. The term half maximal effective concentration ($EC_{50}$) refers to the concentration of a drug, antibody which induces a response halfway between the baseline and maximum after a specified exposure time. Percent of Control values were calculated by dividing the absorbance values for each test well by the No Drug Control average and multiplying by 100.

Combination data was analyzed using CompuSyn® software to calculate Combination Index values to assess synergy. The Fraction Affected (Fa) was calculated from the Percent of Control using the formula: 1−Percent Control/100), where 1 corresponds to 100% effect and 0 corresponds to no effect. The dosage, fraction affected and molar ratio of compounds tested in combination were entered into the CompuSyn® software for evaluation of the presence/absence of synergy. CompuSyn® assigns a Combination Index value which rates the level of compounds' inhibiting 50% of the cell proliferation. CI values below 1 indicate the presence of synergy and CI values above 1 indicate antagonism. CI50 values equal to 1 indicate an additive affect. See Chou, PHARMACOL. REV., 58(3):621-81(2006).

NXS2 cells were grown in DMEM 4.5 g/L de glucose with 10% heat-inactivated fetal calf serum, 2 mM L-Glutamine, 100 units/ml penicillin, and 100 μg/ml streptomycin, at 37° C. in 5% $CO_2$. IMR5, LAN-1 and LAN-5 cells were grown in RPMI 1640 with 10% heat-inactivated fetal calf serum, 2 mM L-Glutamine, 100 units/ml penicillin, and 100 μg/ml streptomycin, at 37° C. in 5% $CO_2$.

We found similar observations when we tested the neuroblastoma cell lines NXS2, IMR5, LAN-1 and LAN-5. The calculated EC50 values of each tested chemotherapeutic drug were significantly lower for the two agent-combinations (i.e. anti-cancer agent and mAb 8B6) ($p<0.05$, Table 3).

TABLE 3

Enhancement of drug cytotoxicity after incubation with mAb 8B6 in neuroblastoma cell lines[a]

| Cell line | Chemotherapy | $EC_{50}$ (μM) | $EC_{50}$ (μM) with mAb 8B6[b] |
|---|---|---|---|
| NXS2 | Isotretinoin | 75.7 | 59.3 |
| | Topotecan | 0.45 | 0.15 |
| | Doxorubicin | 2.75 | 0.016 |
| IMR5 | Isotretinoin | 32.9 | 24 |
| | Topotecan | 0.011 | 0.007 |
| | Doxorubicin | 6.3 | 0.01 |
| LAN-1 | Isotretinoin | 7.4 | 4.3 |
| | Topotecan | 0.771 | 0.015 |
| | Doxorubicin | 4.67 | 0.014 |
| LAN-5 | Isotretinoin | 37.2 | 31.3 |
| | Topotecan | 12.4 | 0.004 |
| | Doxorubicin | 2.09 | 0.13 |

[a] EC50 concentrations are shown as the mean of 3 independent experiments.
[b] Anti-OAcGD2 mAb 8B6 was combined with chemotherapy at the concentration of 40 μg/ml.

Finally, we calculated the median combination index values to characterize the effect of all combinations tested. We found that median combination index values were significantly less than 1.0 ($p<0.05$) across all combinations tested, indicating a synergistic interaction (see Table 4). The combination of isotretinoin and mAb 8B6 gave combination index values ranging from 0.33 to 0.81 (NXS2=0.74, IMR 5=0.81, LAN-1=0.47, LAN-5=0.33) (Table 4). Topotecan showed a stronger synergism with combination index values ranging from 0.28 to 0.60 (NXS2=0.60, IMR 5=0.50, LAN-1=0.58, LAN-5=0.28) (Table 4). The combination with doxorubicin yielded the strongest synergy across the tested neuroblastoma cell lines with combination index values equal or lesser than 0.30 (NXS2=0.30, IMR 5=0.10, LAN-1=0.05, LAN-5=0.16) (Table 4). These data suggest a more potent anti-neuroblastoma efficacy of chemotherapy when used with anti-OAcGD2 mAb 8B6.

TABLE 4

Combination index values

| Cell line | Combination | Combination index 50 Values* |
|---|---|---|
| NXS2 | 8B6 + isotretinoin | 0.74 |
| | 8B6 + topotecan | 0.6 |
| | 8B6 + doxorubicin | 0.3 |
| IMR5 | 8B6 + isotretinoin | 0.81 |
| | 8B6 + topotecan | 0.5 |
| | 8B6 + doxorubicin | 0.10 |
| LAN-1 | 8B6 + isotretinoin | 0.47 |
| | 8B6 + topotecan | 0.58 |
| | 8B6 + doxorubicin | 0.05 |
| LAN-5 | 8B6 + isotretinoin | 0.33 |
| | 8B6 + topotecan | 0.28 |
| | 8B6 + doxorubicin | 0.16 |

*0.05-0.90 = synergism; 0.9-1.10, additive; 1.10-10; antagonism.

Combinations of anti-OAcGD2 mAb 8B6 with other anti-cancer agents were also assayed on LAN-1 neuroblastoma cell line. In this experiment, incorporation of 5-FU, Cisplatin and doxorubicin within the cells in the presence of mAb 8B6 or CTRL-(IgG) was detected using flow cytometry (excitation with a 535 nm laser). Anti-cancer agents and mAb were incubated during 30 minutes at 37° C. Positive control (saponin 0.05%) shows maximal incorporation of chemotherapy in LAN-1 cells.

Figure 3:
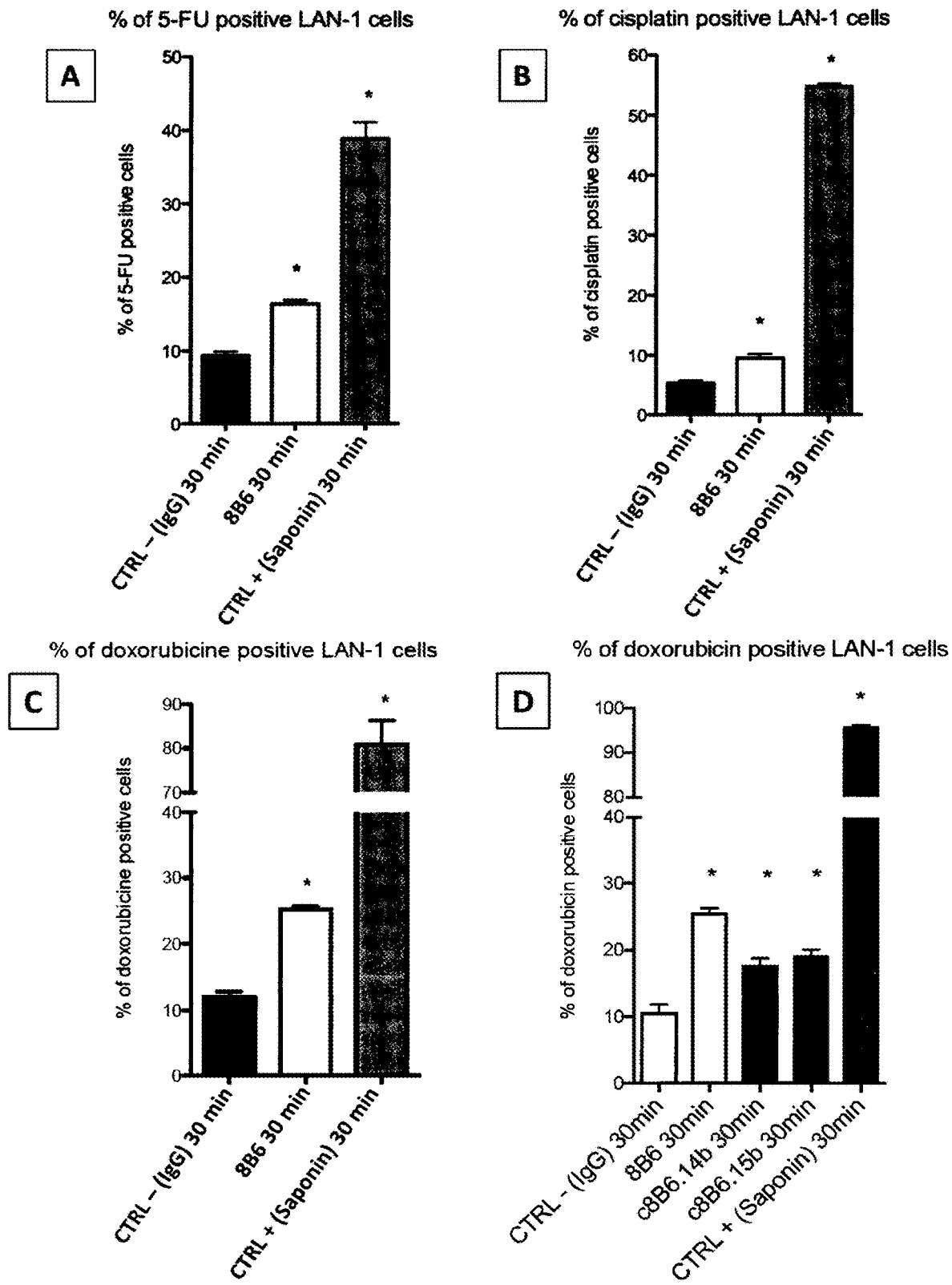
FIG. 3: Internalization of 5-FU, Cisplatin and doxorubicin in neuroblastoma cells. LAN-1 cells were treated with 5-FU (1.52 µM)—Panel A, or Cisplatin (1.52 µM)—Panel B, or doxorubicin (4.7 µM)—Panels C and D with combinations of isotype-matched negative control mouse IgG3 (40 µg/ml) or anti-OAcGD2 mAb 8B6, anti-OAcGD2 mAb c8B6.14b, anti-OAcGD2 mAb c8B6.15b (40 µg/ml). Anti-cancer agents and mAb were incubated during 30 minutes at 37° C. Neuroblastoma cells were fixed with PFA 4% before FACS acquisition. Positive control was performed by treatment of fixed LAN-1 cells with saponin 0.05% in combination with anti-cancer agents during 30 minutes. Incorporation of anti-cancer agents in tumor cells was assessed by flow cytometry (excitation with a 535 nm laser) and results are expressed in percentage of cells having incorporated anti-cancer agent in total cell population.

As shown in FIG. 3, more cells were positive for 5-FU (Panel A), cisplatin (Panel B) at 1.52 µM and doxorubicin (Panel C) at 4.7 µM when incubated with mAb 8B6 than the same cells incubated with anti-cancer agent alone and CTRL-(IgG). Moreover, more cells were positive for doxorubicin (Panel D) at 4.7 µM when incubated with mAb c8B6.14b and mAb c8B6.15b than the same cells incubated with anti-cancer agent alone and CTRL-(IgG).

All these results clearly illustrate that anti-OAcGD2 mAb 8B6 facilitates the penetration of anti-cancer agents in tumor cells.

4. Anti-OAcGD2 mAb 8B6 Shows Synergistic Effect with Temozolomide (TMZ) in Glioblastoma Primary Cells To test whether mAb 8B6 could enhance chemotherapy, we next characterized the effects on tumor cell viability of mAb 8B6 in combination with temozolomide in six different glioblastoma primary cells.

Tumor specimens were collected from patients with a histologic diagnosis of GBM. Tumors were harvested at the time of surgical resection and immediately put into culture after dissociation of the tumors using the gentleMACs™ Dissociator (Miltenyi) according to the manufacturer's instructions. All specimen collection and analysis were performed in accordance with the Institutional Review Board-approved protocol and all patients or their guardians provided written informed consent (Comite de Protection des Personnes Ouest IV, protocol # DC-2012-1555). The cells were maintained in an atmosphere of 5% $CO_2$ and 95% humidity in defined medium (DMEM/Ham F12 containing 2 mM L-glutamine, 100 U/mL penicillin, 100 µg/mL streptomycin, B27 supplement, N2 supplement, 2 µg/ml heparin, 40 ng/ml β-FGF and 40 ng/ml EGF) to form neurospheres.

Cells in the log phase of growth were seeded into 96-well ($1\times10^4$ for AMBMa, DUGAn, DUASOII, GLIO 5, GUITh, and HARCI glioblastoma cells) treated plates in 100 µl of complete media. The cells were allowed to attach during an overnight incubation prior to treating with test agents. Test agents were serially diluted in complete culture media and added to each well in a volume of 50/65 µl for a total final volume of 165 µl/well. Equivalent culture media volume was added to control wells. Three conditions were used: temozolomide alone, mAb 8B6 alone, mAb 8B6+temozolomide. Cells were exposed to test agents for 72 hours. Following the exposure to test agents, 15 µl of MTT reagent was added to each well. The plates were returned to the incubator for four hours. Following the incubation period, kit supplied detergent reagent (100 µl) was added to all wells. The plates were wrapped in plastic wrap to prevent evaporation and allowed to sit at room temperature in the dark overnight. The absorbance at 570 nm was measured the following day using a iMark™ Microplate Absorbance Reader plate reader (Bio-Rad). Assays were performed in quadruplicate and experiments were repeated three times.

Cell viability was measured using the MTT assay and half maximal effective concentration (EC50) was calculated as previously disclosed. Results are illustrated in Table 5 below. We found similar observations when we tested the glioblastoma primary cells AMBMa, DUGAn, DUASOII, GLIO 5, GUITh, and HARCI. The calculated EC50 values of each tested chemotherapeutic drug were lower for the two agent-combinations (i.e. temozolomide and mAb 8B6).

TABLE 5

Enhancement of chemotherapeutic drug cytotoxicity after incubation with mAb 8B6 in glioblastoma primary cells[a]

| Cells | $EC_{50}$ temozolomide (µM) | $EC_{50}$ temozolomide + mAb 8B6[b] |
|---|---|---|
| AMBMa | 783.6 | 238.2 |
| DUASOII | 584.0 | 316.4 |
| DUGAn | 1,119.4 | 592.0 |
| GLIO 5 | 1,589.1 | 972.3 |
| GUITh | 3,159.4 | 2,068.2 |
| HARCI | 13,107 | 3,842.6 |

[a]$EC_{50}$ concentrations are shown as the mean of 3 independent experiments.
[b]Anti-OAcGD2 mAb 8B6 was combined with chemotherapy at the concentration of 40 µg/ml.

Finally, we calculated the median combination index values to characterize the effect of the TMZ and anti-OAcGD2 mAb 8B6 combination tested. We found that median combination index values were significantly less than 1.0 ($p<0.05$) across all combinations tested, indicating a synergistic interaction (see Table 6). The combination of TMZ and mAb 8B6 gave combination index values ranging from 0.27 to 0.66 (GUITh=0.66, DUGAn=0.58, AMBMa=0.27 and HARCI=0.30, GLIO 5=0.41 and DUASOII=0.65) (Table 6). These data suggest a more potent anti-glioblastoma efficacy of TMZ when used with anti-OAcGD2 mAb 8B6.

TABLE 6

Combination index values in glioblastoma primary cells

| Cell line | Combination | Combination index 50 Values* |
|---|---|---|
| AMBMa | 8B6 + Temozolomide | 0.27 |
| DUGAn | 8B6 + Temozolomide | 0.58 |
| DUASOII | 8B6 + Temozolomide | 0.65 |
| GLIO 5 | 8B6 + Temozolomide | 0.41 |
| GUITh | 8B6 + Temozolomide | 0.66 |
| HARCI | 8B6 + Temozolomide | 0.30 |

*0.05-0.90 = synergism; 0.9-1.10, additive; 1.10-10; antagonism.

5. Anti-OAcGD2 mAb 886 Shows Synergistic Effect with Chemotherapeutic Drugs in Other Types of Cancer To test whether anti-OAcGD2 mAb 8B6 could enhance chemotherapy not only in neuroblastoma and glioblastoma, cell lines illustrative for melanoma (M21 cells), breast cancer (MDA-MB-231 cells which overexpress OAcGD2 ganglioside), small cells lung cancer (H524 cells), glioblastoma (DUGAn cells) and Ewing's sarcoma (TC71 cells) were incubated with the specific combination of doxorubicin (0.26 µM, except for MDA-MB-231 cells wherein the concentration of doxorubicin was 0.18 µM; and DUGAn cells wherein the concentration of doxorubicin was 1 µM) and mAb 8B6 or CTRL-(IgG) for 30 minutes. Flow cytometry was used to assess the number of doxorubicin positive cells as previously disclosed in part 3 of the example.

Figure 4:
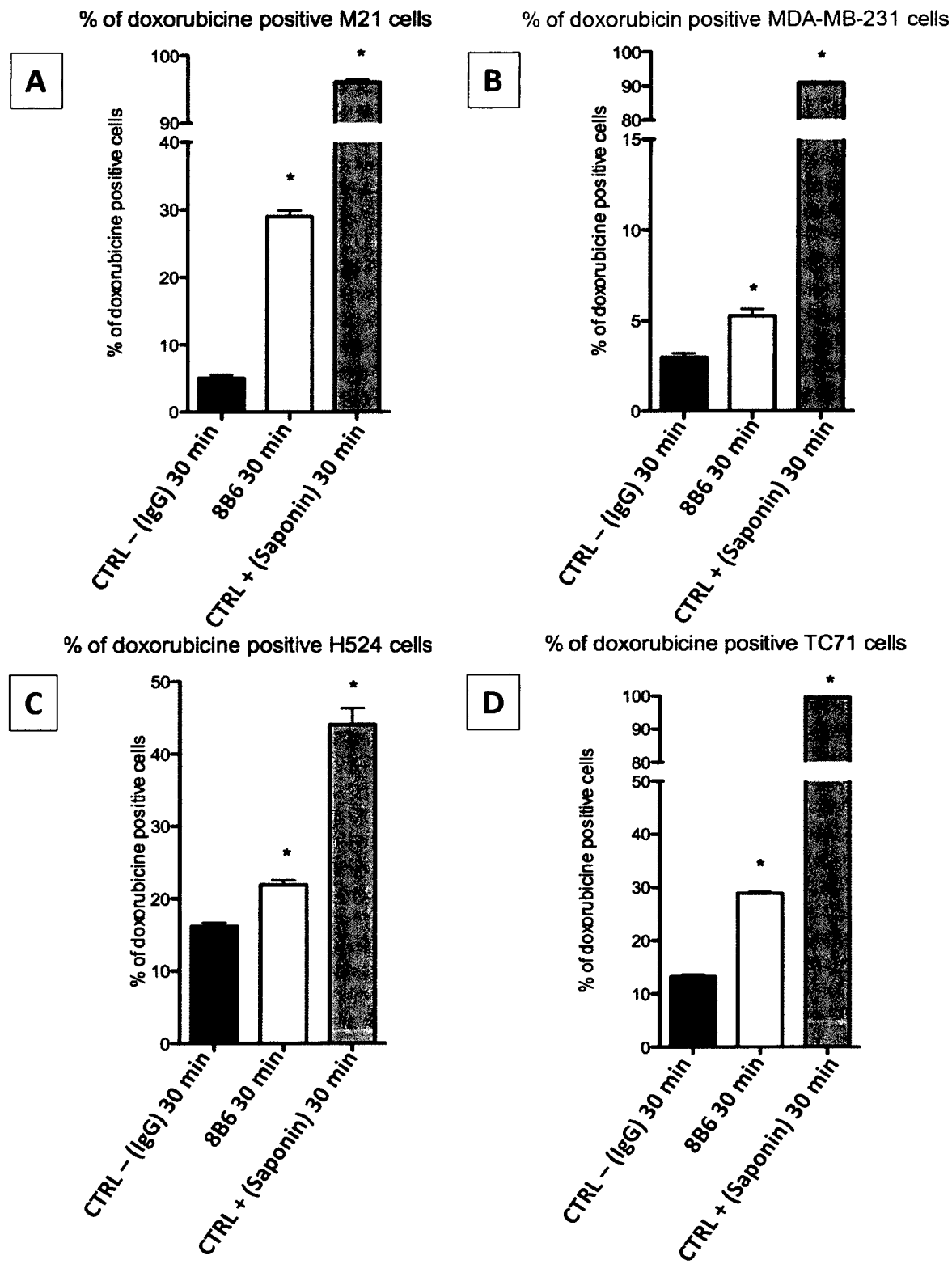
FIG. 4: Internalization of doxorubicin in melanoma (M21 cells), breast cancer (MDA-MB-231 cells), Small cells lung cancer (H524 cells), Ewing's sarcoma cells (TC71 cells) and glioblastoma cells (DuGan). Cells were treated with anti-cancer agents 0.26 µM (except for MDA-MB-231, 0.18 µM) with combinations of isotype-matched negative control mouse IgG3 (40 µg/ml) or anti-OAcGD2 mAb 8B6 (40 µg/ml). Anti-cancer agents and mAb were incubated during 30 minutes at 37° C. Tumor cells were fixed with PFA 4% before FACS acquisition. Positive control was performed by treatment of fixed tumor cells with saponin 0.05% in combination with anti-cancer agents during 30 minutes. Incorporation of anti-cancer agents in melanoma (M21)—Panel A, breast cancer (MDA-MB-231)—Panel B, Small cells lung cancer (H524)—Panel C, Ewing's sarcoma (TC71)—Panel D, and glioblastoma (DuGan)—Panel E cells was assessed by flow cytometry (excitation with a 535 nm laser) and results are expressed in percentage of cells having incorporated anti-cancer agent in total cell population.

As illustrated in FIG. 4, anti-OAcGD2 mAb 8B6 increases significantly the percentage of doxorubicin positive cells in all types of cancer. More specifically, a six fold increase in doxorubicin positive cells is observed for M21 melanoma cell line (panel A), more than two fold increase in doxorubicin positive cells is observed for TC71 Ewing's sarcoma cell line (panel D), almost two fold increase in doxorubicin positive cells is observed for MDA-MB-231 breast cancer cell line (panel B), 1.5 fold increase in doxorubicin positive cells is observed for H524 small cell lung cancer cell line (panel C), 1.16 fold increase in doxorubicin positive cell for DUGAn glioblastoma cells (panel E).

Taken together, these results demonstrated that anti-OAcGD2 mAb 8B6 facilitates the penetration of the anti-cancer agent in several types of cancer, especially those having cells expressing O-acetylated GD2 ganglioside.

6. Anti-OAcGD2 8B6 mAb Enhances Anti-Tumor Activity of Chemotherapeutic Drugs in a Murine Neuroblastoma Liver Metastasis Model 6.1—Murine Tumor Model The anti-neuroblastoma efficacy of anti-OAcGD2 mAb 8B6 and chemotherapeutic treatments was determined in the murine NXS2 neuroblastoma experimental liver metastasis model in A/J mice, previously described by Lode et al. (J Natl Cancer Inst 1997, 89: 1586-1594). This study was carried out in strict accordance with the recommendations in the Guide for the Care and Use of Laboratory Animals of the French Department of Agriculture. The protocol was approved by the Committee on the Ethics of Animal Experiments of the Region Pays de la Loire. Mice were housed at the UTE-UN animal facility (Nantes, France). Female and male A/J mice (6-8 weeks of age) were obtained from Harlan Laboratories (Gannat, France). We inoculated $2.5 \times 10^5$ tumor cells by tail vein in PBS. We grouped the mice into nine groups of 10 mice each: 1) vehicle-treated group; 2) control antibody-treated group; 3) anti-OAcGD2 mAb 8B6-treated group; 4) isotretinoin-treated group; 5) topotecan-treated group; 6) doxorubicin-treated group; 7) Isotretinoin+mAb 8B6-treated group, 8) topotecan+mAb 8B6-treated group; and 9) doxorubicin+mAb 8B6-treated group. Anti-OAcGD2 mAb 8B6 treatment was started at Day 3 after tumor cells injection. Mice received by i.v. injection twice a week 25 µg mAb 8B6 for 3 consecutive weeks; (day 3, 7, 10, 14, 17 and 21; total dose=150 µg). Isotretinoin was given orally diluted in Ora-Plus© at 10 mg/kg daily for 2 consecutive weeks (on days 10-14 and 17-21). Topotecan diluted in PBS was given by i.p. injection at 0.36 mg/kg daily for one week (on days 10-14). Doxorubicin was given by i.p. injection at 1 mg/kg daily for two weeks (on days 10-14 and 17-21). Mice were sacrificed after 28 days post inoculation, and anti-tumor efficacy was evaluated by liver weight of the fresh specimen as well as hepatic metastasis number.

6.2—Results

Figure 5:
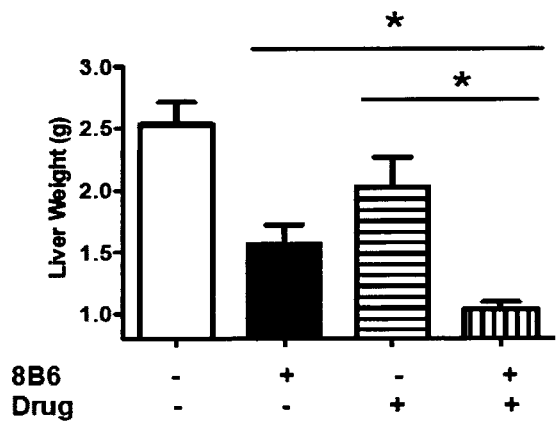
FIG. 5: Enhancement of chemotherapy anti-tumor activity by anti-OAcGD2 mAb 8B6 in in vivo neuroblastoma experimental liver metastasis mice model. Mice (n=10/group) were inoculated with $2.5 \times 10^5$ NXS2 mouse neuroblastoma cells by i.v. injections. 8B6 mAb treatment was started on day 3 after tumor cell inoculation twice a week for 3 consecutive weeks (cumulative dose=150 µg, A-C). All chemotherapeutic treatments were started at day 10 post-tumor inoculation. Panel A: isotretinoin was given at 10 mg/kg, per os, five times weekly for 2 weeks. Panel B: topotecan was given by i.p. injections at 0.36 mg/kg five times weekly for 1 week. Panel C: doxorubicin was given by i.p. injections at 1 mg/kg five times weekly for 2 weeks. Mice were euthanized 28 days post-tumor inoculation. Anti-tumor efficacy was evaluated by determining the liver weight on the fresh specimen compared to the mice treated with vehicle only. The liver weight is indicative of hepatic metastasis number. The y-axis starts at 0.8 g corresponding to the average normal liver weight. Data are presented as the mean±SEM.
Figure 5:
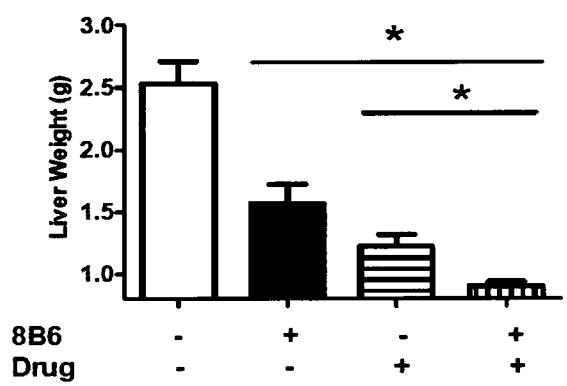
Figure 5:
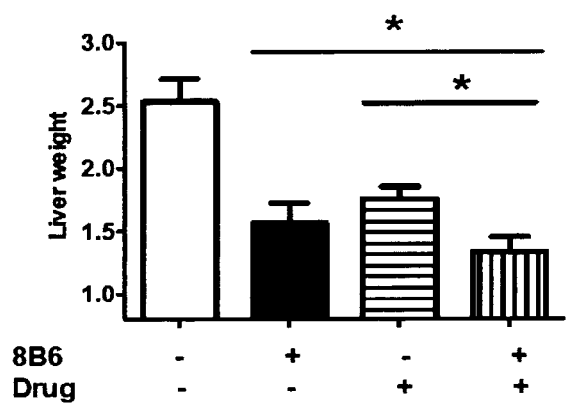

To extend our observations obtained in vitro, we next evaluated the potential therapeutic effects of mAb 8B6/chemotherapy combination in vivo. We performed the in vivo studies using the mouse NXS2 neuroblastoma experimental liver metastasis model as disclosed by Alvarez-Rueda et al. (ALVAREZ-RUEDA et al. PLoS One 2011, vol. 6(9), p:e25220). Anti-cancer agents were given at low doses as previously reported in the literature in order to minimize related side effects. Three days after i.v. NSX2 tumor cell inoculation, ten mice were assigned to treatment with single agent, or combination of mAb 8B6 and anti-cancer agents as described previously. On day 28 after tumor cell inoculation, we determined the number of liver metastases and the liver weight after mice euthanasia. The dose of mAb 8B6 (cumulative dose=150 µg) that we used in this study yielded a significant reduction of NXS2 liver metastasis, as indicated by the liver weight compared to the vehicle treated mice. The mean liver weight in mAb 8B6-treated group was 1.5±0.15 g compared to 2.5±0.18 g for the vehicle-treated group (p<0.05, FIG. 5). The specificity of anti-OAcGD2 mAb 8B6 therapy was demonstrated, since treatment with an equivalent amount of non-specific antibody was completely ineffective (mean liver weight=2.5±0.18 g, p>0.05 compared to vehicle-treated mice, data not shown). Antibody 8B6 cooperated with isotretinoin (10 mg/kg, per os, five times weekly for 2 weeks) resulting in a significant sensitization for isotretinoin inhibition of NXS2 metastasis growth (p<0.05, FIG. 5 panel A). The mean liver weight in the isotretinoin+mAb 8B6-treated group was 1.0±0.06 g and 2.0±0.24 g for the isotretinoin-treated group. The combination of the inhibitor of topoisomerase I topotecan (0.36 mg/kg, i.p., five times weekly for 1 week) plus mAb 8B6 also significantly reduced liver weight (0.9±0.03 g) compared to either topotecan (1.22±0.09 g), or mAb 8B6 alone (p<0.05, FIG. 5 panel B). The combination of the anthracycline antibiotics doxorubicin (1 mg/kg, i.p., five times weekly for 2 weeks) resulted in a significant reduction of the liver weight (1.33±0.12 g) compared to treatment with either doxorubicin (1.75±0.09 g), or mAb 8B6 alone (p<0.05, FIG. 5 panel C). The combination with mAb 8B6 with either isotretinoin or topotecan resulted in the strongest therapeutic efficacy among the three combination regimens tested (FIG. 5).

Figure 6:
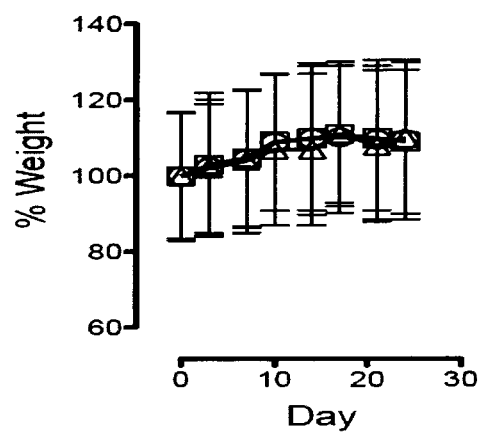
FIG. 6: Systemic tolerability of anti-OAcGD2 mAb 8B6 in combinations with isotretinoin (Panel A), topotecan (Panel B), and doxorubicin (Panel C). Mean weight of group of mice (n=10) presented in FIG. 6 at day 0 was defined as 100% weight. Weight in each group remained stable for the period of treatment. Δ, mice treated with mAb 8B6; ○, mice treated with anti-cancer agent; □, mice treated with chemotherapeutic drug plus mAb 8B6.
Figure 6:
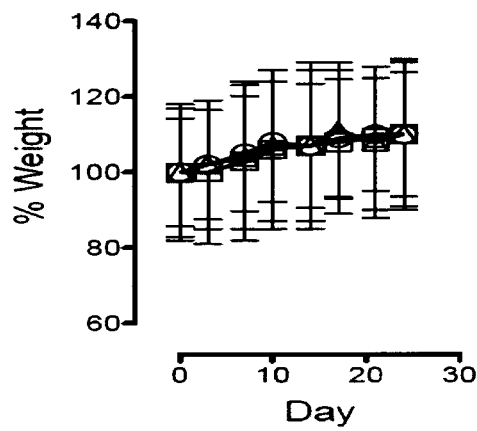
Figure 6:
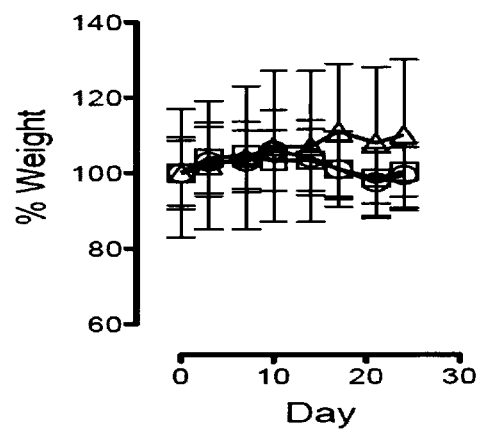

Weight loss is used as a sensitive marker for health monitoring. We therefore performed a parallel analysis of the body weight over the treatment period. We observed no loss of body weight (FIG. 6), suggesting no treatment related toxicity in the mice treated with mAb 8B6, isotretinoin, isotretinoin+mAb 8B6, topotecan, or topotecan+mAb 8B6. Mice receiving doxorubicin or doxorubicin plus mAb 8B6 displayed a loss of body weight after day 17 compared to those mice receiving only mAb 8B6. The body-weight difference between the two groups treated with doxorubicin compared to the non-doxorubicin group, however, fails to be significant during the treatment period (p>0.05). These observations suggest that the combination with anti-cancer agent plus mAb 8B6 presents a more potent anti-tumor efficacy in vivo than either agent alone, without detectable toxicity.

7. Anti-OAcGD2 8B6 mAb Restores the Anti-Cancer Effect of Chemotherapeutic Drugs in a Refractory Glioblastoma Model 7.1—Materials and Methods 7.1.1—Pharmacological Agent.

Anti-OAcGD2 mAb 8B6 and isotype control antibody (CTRL) were obtained as previously described. Temozolomide (TMZ) was purchased from Interchim (Montluçon, France).

TMZ was reconstituted with DMSO and aliquots were stored at −20° C. DMSO at a final percentage equivalent to that of the TMZ solution served as the vehicle control for all studies.

7.1.2—Cell Culture.

Patient-derived glioblastoma GBM-10 cells were maintained as neurospheres in DMEM/Ham F12 containing 1% penicillin and streptomycin supplemented with L-glutamine, B27, N2 supplement, and heparin (2 µg/ml), with additional growth factors β-FGF (40 ng/ml) and EGF (40 ng/ml) added extemporaneously, respectively. Culture reagents were obtained from Gibco Life Technologies (Waltham, Mass.). All Cell types were kept at early passage and routinely tested for *Mycoplasma* by PCR.

7.1.3—O-Acetyl-GD2 Expression in GBM10 Cells.

Analysis of OAcGD2 expression in GBM cells were performed by indirect immunofluorescence measured by flow cytometry. Cells were washed with cold PBS, fixed with PFA 4% (Electron Microscopy Sciences, Hatfield, Pa.) for 10 min at 4° C., and then incubated with mAb 8B6 (10 µg/ml) for 45 min. Antibody 8B6 binding was detected by incubation with a fluorescein isothiocyanate-labeled F(ab')2 fragment of goat anti-mouse IgG (Jackson Immunoresearch, Soham, UK) for 60 min at 4° C. Separate experiments were performed with the control IgG. Cell fluorescence was analyzed using a FACSCanto flow cytometer (BD Biosciences, San Jose, Calif., USA) and the FlowJo software (Flowjo LLC, Oregon, Oreg., USA). Results were expressed by MFI ratios.

7.1.4—Limiting Dilution Analysis.

For limiting dilution assays, GBM tumors were dissociated and isolated cells were seeded at an initial concentration of $10^3$ cells/mL from which serial dilutions were performed in 96-well plate. Cells were cultured for 15 days, after which the fraction of wells that did not contain neurospheres for each cell-plating density was calculated and data were analyzed with the ELDA software (ELDA, Linz, Austria) to quantify the frequency of Glioblastoma Stem Cells (GSC) in sample and the impact of various treatment.

7.1.4—Glioblastoma Xenograft Mouse Model.

NSG (NOD.Cg-Prkdcscid Il2rgtm1Wjl/SzJ) mice purchased Charles River Laboratories, (Wilmington, Mass.) were bred in the animal facility of the University of Nantes (UTE, SFR F. Bonamy) under SPF status and used at 6-12 weeks of age, accordingly to institutional guidelines (Agreement #00186.02; Regional ethics committee of the Pays de la Loire, France). GBM-10 cells ($1 \times 10^6$ in 100 µl Matrigel, Corning, Corning, N.Y., USA) were injected subcutaneously at Day 0. TMZ was administered by i.p. injection at a single dose of 0.05 mg/mouse on Day 12, 22 and 32.

7.2—Results—

Figure 7:
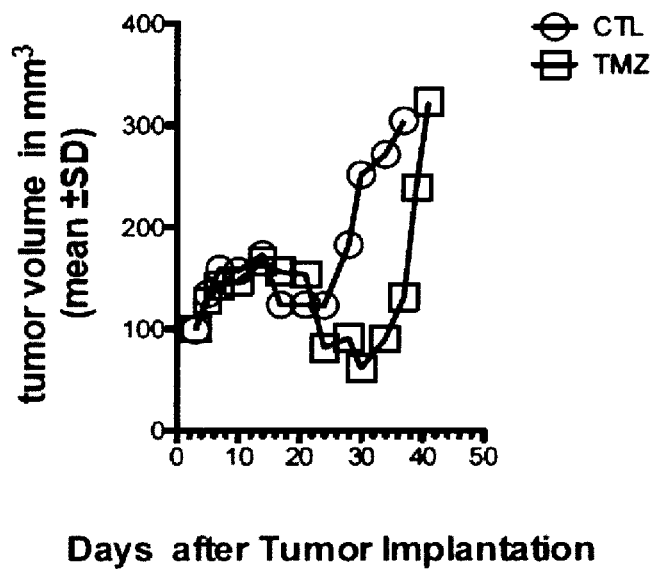
FIG. 7: Anti-OAcGD2 mAb 8B6 overcomes tumor resistance in patient-derived TMZ-refractory GBM-10 cells (GBM-10 $TMZ^R$) in in vivo glioblastoma xenograft mouse model. $1 \times 10^6$ GBM-10 cells were injected subcutaneously in mice at day 0. Mice were then divided in two groups: the first group of mice received Temozolomide (TMZ) by i.p. injection in a single dose of 0.05 mg/mouse on days 12, 22 and 32 whereas the second group of mice was left untreated. Tumor volume (Panel A) was monitored. OAcGD2 expression was assessed in GBM-10 cells isolated from both TMZ treated mice and untreated mice (Panel B). TMZ refractory level was next determined by limiting dilution assay and expressed as glioblastoma cancer stem cells (GSC) frequency in the tumor xenograft. Effects of monotherapy (8B6 or TMZ) and two-agent combination (TMZ+8B6) on GSC survival were compared in the GBM-10 cells isolated from untreated (Panel C, GBM-10 CTL (TMZs)) and relapse GBM-10 xenografts (Panel D, GBM-10 $TMZ^R$).
Figure 7:
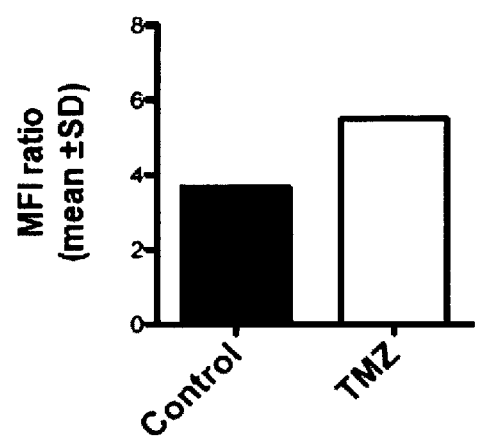
Figure 7:
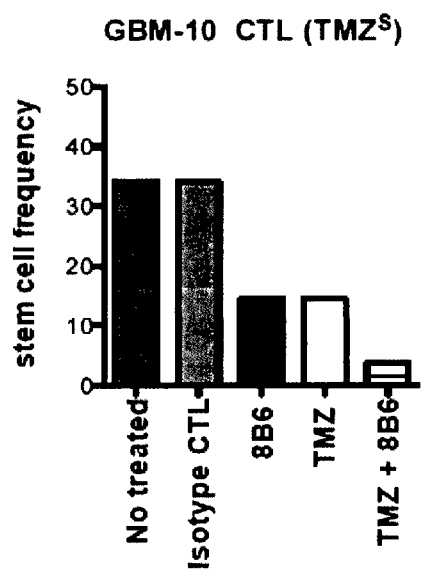
Figure 7:
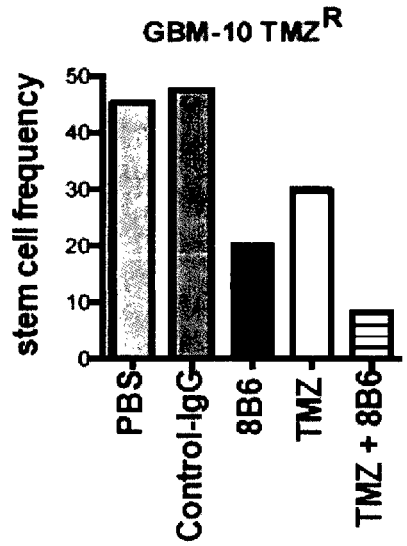

TMZ-refractory GBM-10 cells (GBM-10 $TMZ^R$) was isolated from relapse GBM-10 cells after TMZ chemotherapy (FIG. 7 Panel A). The O-acetyl-GD2 expression level was determined by flow cytometry analysis as describe in the Material & Method Section. Results show that O-acetyl GD2 expression remains after TMZ chemotherapy compared to GBM-10 cell isolated from untreated mice (FIG. 7 Panel B).

TMZ refractory level was next determined by limiting dilution assay and expressed as glioblastoma cancer stem cells frequency in the tumor xenograft. Results indicate that the stem cell frequency was increased upon TMZ chemotherapy (FIG. 7 Panels C & D). Indeed in the untreated mice, both TMZ- or mAb 8B6-exposure decreased the stem cell survival (FIG. 7 Panel C). More importantly, the effect induced by the two-agent combination (TMZ+8B6) was significantly higher than the two agents used as monotherapy, respectively.

Effect of TMZ chemotherapy was far less efficient in inhibiting the stem cell survival in the GBM-10 cells isolated from relapse GBM-10 xenografts (FIG. 7 Panel D). Surprisingly, the two-agent combination (TMZ+8B6) was able to decrease the GSC survival.

SEQUENCE LISTING

```
<160> NUMBER OF SEQ ID NOS: 50

<210> SEQ ID NO 1
<211> LENGTH: 113
<212> TYPE: PRT
<213> ORGANISM: Artificial Sequence
<220> FEATURE:
<223> OTHER INFORMATION: OGD201 Consensus sequence for third humanized
      VL sequence
<220> FEATURE:
<221> NAME/KEY: MISC_FEATURE
<222> LOCATION: (1)..(1)
<223> OTHER INFORMATION: X=D or E
<220> FEATURE:
<221> NAME/KEY: MISC_FEATURE
<222> LOCATION: (9)..(9)
<223> OTHER INFORMATION: X=L or A
<220> FEATURE:
<221> NAME/KEY: MISC_FEATURE
<222> LOCATION: (10)..(10)
<223> OTHER INFORMATION: X=S or T
<220> FEATURE:
<221> NAME/KEY: MISC_FEATURE
<222> LOCATION: (12)..(12)
<223> OTHER INFORMATION: X=P or S
<220> FEATURE:
<221> NAME/KEY: MISC_FEATURE
<222> LOCATION: (13)..(13)
<223> OTHER INFORMATION: X=V or L or A
<220> FEATURE:
<221> NAME/KEY: MISC_FEATURE
<222> LOCATION: (14)..(14)
<223> OTHER INFORMATION: X=S or T
<220> FEATURE:
<221> NAME/KEY: MISC_FEATURE
<222> LOCATION: (15)..(15)
<223> OTHER INFORMATION: X=L or P or V
<220> FEATURE:
<221> NAME/KEY: MISC_FEATURE
<222> LOCATION: (17)..(17)
<223> OTHER INFORMATION: X=D or Q or E
<220> FEATURE:
<221> NAME/KEY: MISC_FEATURE
<222> LOCATION: (18)..(18)
<223> OTHER INFORMATION: X=Q or P or R
```

```
<220> FEATURE:
<221> NAME/KEY: MISC_FEATURE
<222> LOCATION: (19)..(19)
<223> OTHER INFORMATION: X=A or V
<220> FEATURE:
<221> NAME/KEY: MISC_FEATURE
<222> LOCATION: (20)..(20)
<223> OTHER INFORMATION: X=S or T
<220> FEATURE:
<221> NAME/KEY: MISC_FEATURE
<222> LOCATION: (21)..(21)
<223> OTHER INFORMATION: X=I or L
<220> FEATURE:
<221> NAME/KEY: MISC_FEATURE
<222> LOCATION: (22)..(22)
<223> OTHER INFORMATION: X=S or T
<220> FEATURE:
<221> NAME/KEY: MISC_FEATURE
<222> LOCATION: (25)..(25)
<223> OTHER INFORMATION: X=S or A
<220> FEATURE:
<221> NAME/KEY: MISC_FEATURE
<222> LOCATION: (29)..(29)
<223> OTHER INFORMATION: X=L or V
<220> FEATURE:
<221> NAME/KEY: MISC_FEATURE
<222> LOCATION: (30)..(30)
<223> OTHER INFORMATION: X=L or V
<220> FEATURE:
<221> NAME/KEY: MISC_FEATURE
<222> LOCATION: (32)..(32)
<223> OTHER INFORMATION: X=N or S
<220> FEATURE:
<221> NAME/KEY: MISC_FEATURE
<222> LOCATION: (33)..(33)
<223> OTHER INFORMATION: X=N or Q
<220> FEATURE:
<221> NAME/KEY: MISC_FEATURE
<222> LOCATION: (34)..(34)
<223> OTHER INFORMATION: X=G or A or S
<220> FEATURE:
<221> NAME/KEY: MISC_FEATURE
<222> LOCATION: (35)..(35)
<223> OTHER INFORMATION: X=N or Y or S
<220> FEATURE:
<221> NAME/KEY: MISC_FEATURE
<222> LOCATION: (36)..(36)
<223> OTHER INFORMATION: X=T or N or S
<220> FEATURE:
<221> NAME/KEY: MISC_FEATURE
<222> LOCATION: (37)..(37)
<223> OTHER INFORMATION: X=F or Y
<220> FEATURE:
<221> NAME/KEY: MISC_FEATURE
<222> LOCATION: (39)..(39)
<223> OTHER INFORMATION: X= H or N or S or A or D or Y or G
<220> FEATURE:
<221> NAME/KEY: MISC_FEATURE
<222> LOCATION: (41)..(41)
<223> OTHER INFORMATION: X=Y or F
<220> FEATURE:
<221> NAME/KEY: MISC_FEATURE
<222> LOCATION: (42)..(42)
<223> OTHER INFORMATION: X=L or Q
<220> FEATURE:
<221> NAME/KEY: MISC_FEATURE
<222> LOCATION: (44)..(44)
<223> OTHER INFORMATION: X=K or R
<220> FEATURE:
<221> NAME/KEY: MISC_FEATURE
<222> LOCATION: (47)..(47)
<223> OTHER INFORMATION: X=Q or K
<220> FEATURE:
<221> NAME/KEY: MISC_FEATURE
<222> LOCATION: (48)..(48)
<223> OTHER INFORMATION: X=S or A
<220> FEATURE:
<221> NAME/KEY: MISC_FEATURE
<222> LOCATION: (50)..(50)
```

```
<223> OTHER INFORMATION: X=K or Q or R
<220> FEATURE:
<221> NAME/KEY: MISC_FEATURE
<222> LOCATION: (51)..(51)
<223> OTHER INFORMATION: X=L or R
<220> FEATURE:
<221> NAME/KEY: MISC_FEATURE
<222> LOCATION: (55)..(55)
<223> OTHER INFORMATION: X=K or G or L
<220> FEATURE:
<221> NAME/KEY: MISC_FEATURE
<222> LOCATION: (56)..(56)
<223> OTHER INFORMATION: X=V or A or G
<220> FEATURE:
<221> NAME/KEY: MISC_FEATURE
<222> LOCATION: (58)..(58)
<223> OTHER INFORMATION: X=N or T
<220> FEATURE:
<221> NAME/KEY: MISC_FEATURE
<222> LOCATION: (60)..(60)
<223> OTHER INFORMATION: X=L or D or A
<220> FEATURE:
<221> NAME/KEY: MISC_FEATURE
<222> LOCATION: (61)..(61)
<223> OTHER INFORMATION: X=S or T
<220> FEATURE:
<221> NAME/KEY: MISC_FEATURE
<222> LOCATION: (63)..(63)
<223> OTHER INFORMATION: X=V or I
<220> FEATURE:
<221> NAME/KEY: MISC_FEATURE
<222> LOCATION: (65)..(65)
<223> OTHER INFORMATION: X=D or A or S
<220> FEATURE:
<221> NAME/KEY: MISC_FEATURE
<222> LOCATION: (75)..(75)
<223> OTHER INFORMATION: X=Y or D
<220> FEATURE:
<221> NAME/KEY: MISC_FEATURE
<222> LOCATION: (79)..(79)
<223> OTHER INFORMATION: X=K or T
<220> FEATURE:
<221> NAME/KEY: MISC_FEATURE
<222> LOCATION: (82)..(82)
<223> OTHER INFORMATION: X=R or S
<220> FEATURE:
<221> NAME/KEY: MISC_FEATURE
<222> LOCATION: (83)..(83)
<223> OTHER INFORMATION: X=V or L
<220> FEATURE:
<221> NAME/KEY: MISC_FEATURE
<222> LOCATION: (84)..(84)
<223> OTHER INFORMATION: X=E or Q
<220> FEATURE:
<221> NAME/KEY: MISC_FEATURE
<222> LOCATION: (85)..(85)
<223> OTHER INFORMATION: X=A or P
<220> FEATURE:
<221> NAME/KEY: MISC_FEATURE
<222> LOCATION: (88)..(88)
<223> OTHER INFORMATION: X=L or V or F
<220> FEATURE:
<221> NAME/KEY: MISC_FEATURE
<222> LOCATION: (89)..(89)
<223> OTHER INFORMATION: X=G or A
<220> FEATURE:
<221> NAME/KEY: MISC_FEATURE
<222> LOCATION: (90)..(90)
<223> OTHER INFORMATION: X=V or T
<220> FEATURE:
<221> NAME/KEY: MISC_FEATURE
<222> LOCATION: (92)..(92)
<223> OTHER INFORMATION: X=Y or F
<220> FEATURE:
<221> NAME/KEY: MISC_FEATURE
<222> LOCATION: (94)..(94)
<223> OTHER INFORMATION: X=S or M or Q
<220> FEATURE:
<221> NAME/KEY: MISC_FEATURE
```

-continued

```
<222> LOCATION: (96)..(96)
<223> OTHER INFORMATION: X=S or A
<220> FEATURE:
<221> NAME/KEY: MISC_FEATURE
<222> LOCATION: (97)..(97)
<223> OTHER INFORMATION: X=T or Y  or L
<220> FEATURE:
<221> NAME/KEY: MISC_FEATURE
<222> LOCATION: (98)..(98)
<223> OTHER INFORMATION: X=H or Q  or N
<220> FEATURE:
<221> NAME/KEY: MISC_FEATURE
<222> LOCATION: (99)..(99)
<223> OTHER INFORMATION: X=I or T
<220> FEATURE:
<221> NAME/KEY: MISC_FEATURE
<222> LOCATION: (100)..(100)
<223> OTHER INFORMATION: X= P or S
<220> FEATURE:
<221> NAME/KEY: misc_feature
<222> LOCATION: (101)..(101)
<223> OTHER INFORMATION: Xaa can be any naturally occurring amino acid
<220> FEATURE:
<221> NAME/KEY: MISC_FEATURE
<222> LOCATION: (105)..(105)
<223> OTHER INFORMATION: X=G or Q
<220> FEATURE:
<221> NAME/KEY: misc_feature
<222> LOCATION: (106)..(106)
<223> OTHER INFORMATION: Xaa can be any naturally occurring amino acid

<400> SEQUENCE: 1

Xaa Val Val Met Thr Gln Ser Pro Xaa Xaa Leu Xaa Xaa Xaa Xaa Gly
1               5                   10                  15

Xaa Xaa Xaa Xaa Xaa Xaa Cys Arg Xaa Ser Gln Ser Xaa Xaa Lys Xaa
            20                  25                  30

Xaa Xaa Xaa Xaa Xaa Leu Xaa Trp Xaa Xaa Gln Xaa Pro Gly Xaa Xaa
        35                  40                  45

Pro Xaa Xaa Leu Ile Tyr Xaa Xaa Ser Xaa Arg Xaa Xaa Gly Xaa Pro
    50                  55                  60

Xaa Arg Phe Ser Gly Ser Gly Ser Gly Thr Xaa Phe Thr Leu Xaa Ile
65                  70                  75                  80

Ser Xaa Xaa Xaa Xaa Glu Asp Xaa Xaa Xaa Tyr Xaa Cys Xaa Gln Ser
                85                  90                  95

Xaa Xaa Xaa Xaa Xaa Tyr Thr Phe Gly Xaa Gly Thr Lys Val Glu Ile
            100                 105                 110

Lys

<210> SEQ ID NO 2
<211> LENGTH: 119
<212> TYPE: PRT
<213> ORGANISM: Artificial Sequence
<220> FEATURE:
<223> OTHER INFORMATION: OGD201 Consensus sequence for third humanized
      VH sequence
<220> FEATURE:
<221> NAME/KEY: MISC_FEATURE
<222> LOCATION: (1)..(1)
<223> OTHER INFORMATION: X=E or Q
<220> FEATURE:
<221> NAME/KEY: MISC_FEATURE
<222> LOCATION: (5)..(5)
<223> OTHER INFORMATION: X=V or L
<220> FEATURE:
<221> NAME/KEY: MISC_FEATURE
<222> LOCATION: (13)..(13)
<223> OTHER INFORMATION: X=Q or K
<220> FEATURE:
<221> NAME/KEY: MISC_FEATURE
<222> LOCATION: (16)..(16)
```

```
<223> OTHER INFORMATION: X= G or R
<220> FEATURE:
<221> NAME/KEY: MISC_FEATURE
<222> LOCATION: (23)..(23)
<223> OTHER INFORMATION: X= A or T
<220> FEATURE:
<221> NAME/KEY: MISC_FEATURE
<222> LOCATION: (24)..(24)
<223> OTHER INFORMATION: X= T or A
<220> FEATURE:
<221> NAME/KEY: MISC_FEATURE
<222> LOCATION: (26)..(26)
<223> OTHER INFORMATION: X= E or G
<220> FEATURE:
<221> NAME/KEY: MISC_FEATURE
<222> LOCATION: (30)..(30)
<223> OTHER INFORMATION: X= T or S or G
<220> FEATURE:
<221> NAME/KEY: MISC_FEATURE
<222> LOCATION: (32)..(32)
<223> OTHER INFORMATION: X= Y or H
<220> FEATURE:
<221> NAME/KEY: MISC_FEATURE
<222> LOCATION: (35)..(35)
<223> OTHER INFORMATION: X= T or D or S or H or N
<220> FEATURE:
<221> NAME/KEY: MISC_FEATURE
<222> LOCATION: (48)..(48)
<223> OTHER INFORMATION: X= L or V
<220> FEATURE:
<221> NAME/KEY: MISC_FEATURE
<222> LOCATION: (49)..(49)
<223> OTHER INFORMATION: X= G or S
<220> FEATURE:
<221> NAME/KEY: MISC_FEATURE
<222> LOCATION: (50)..(50)
<223> OTHER INFORMATION: X= F or Y
<220> FEATURE:
<221> NAME/KEY: MISC_FEATURE
<222> LOCATION: (51)..(51)
<223> OTHER INFORMATION: X= I or T
<220> FEATURE:
<221> NAME/KEY: MISC_FEATURE
<222> LOCATION: (54)..(54)
<223> OTHER INFORMATION: X= R or K or S
<220> FEATURE:
<221> NAME/KEY: MISC_FEATURE
<222> LOCATION: (55)..(55)
<223> OTHER INFORMATION: X= A or S
<220> FEATURE:
<221> NAME/KEY: MISC_FEATURE
<222> LOCATION: (57)..(57)
<223> OTHER INFORMATION: X= G or A or S
<220> FEATURE:
<221> NAME/KEY: MISC_FEATURE
<222> LOCATION: (58)..(58)
<223> OTHER INFORMATION: X= Y or S or G
<220> FEATURE:
<221> NAME/KEY: MISC_FEATURE
<222> LOCATION: (59)..(59)
<223> OTHER INFORMATION: X= T or I
<220> FEATURE:
<221> NAME/KEY: MISC_FEATURE
<222> LOCATION: (60)..(60)
<223> OTHER INFORMATION: X= T or I
<220> FEATURE:
<221> NAME/KEY: MISC_FEATURE
<222> LOCATION: (61)..(61)
<223> OTHER INFORMATION: X= E or Y
<220> FEATURE:
<221> NAME/KEY: MISC_FEATURE
<222> LOCATION: (63)..(63)
<223> OTHER INFORMATION: X= N or A
<220> FEATURE:
<221> NAME/KEY: MISC_FEATURE
<222> LOCATION: (64)..(64)
<223> OTHER INFORMATION: X= P or A or D
<220> FEATURE:
<221> NAME/KEY: MISC_FEATURE
```

```
<222> LOCATION: (76)..(76)
<223> OTHER INFORMATION: X= N or G
<220> FEATURE:
<221> NAME/KEY: MISC_FEATURE
<222> LOCATION: (77)..(77)
<223> OTHER INFORMATION: X= S or A
<220> FEATURE:
<221> NAME/KEY: MISC_FEATURE
<222> LOCATION: (79)..(79)
<223> OTHER INFORMATION: X= S or N
<220> FEATURE:
<221> NAME/KEY: MISC_FEATURE
<222> LOCATION: (80)..(80)
<223> OTHER INFORMATION: X= I or S or T
<220> FEATURE:
<221> NAME/KEY: MISC_FEATURE
<222> LOCATION: (81)..(81)
<223> OTHER INFORMATION: X= L or T or A
<220> FEATURE:
<221> NAME/KEY: MISC_FEATURE
<222> LOCATION: (89)..(89)
<223> OTHER INFORMATION: X= R or K or Q
<220> FEATURE:
<221> NAME/KEY: MISC_FEATURE
<222> LOCATION: (90)..(90)
<223> OTHER INFORMATION: X= T or A
<220> FEATURE:
<221> NAME/KEY: MISC_FEATURE
<222> LOCATION: (95)..(95)
<223> OTHER INFORMATION: X= V or I or L
<220> FEATURE:
<221> NAME/KEY: MISC_FEATURE
<222> LOCATION: (99)..(99)
<223> OTHER INFORMATION: X= T or A
<220> FEATURE:
<221> NAME/KEY: MISC_FEATURE
<222> LOCATION: (114)..(114)
<223> OTHER INFORMATION: X= T or L
<220> FEATURE:
<221> NAME/KEY: MISC_FEATURE
<222> LOCATION: (115)..(115)
<223> OTHER INFORMATION: X= L or V

<400> SEQUENCE: 2

Xaa Val Gln Leu Xaa Glu Ser Gly Gly Gly Leu Val Xaa Pro Gly Xaa
1               5                   10                  15

Ser Leu Arg Leu Ser Cys Xaa Xaa Ser Xaa Phe Thr Phe Xaa Asp Xaa
            20                  25                  30

Tyr Met Xaa Trp Val Arg Gln Ala Pro Gly Lys Gly Leu Glu Trp Xaa
        35                  40                  45

Xaa Xaa Xaa Arg Asn Xaa Xaa Asn Xaa Xaa Xaa Xaa Xaa Tyr Xaa Xaa
    50                  55                  60

Ser Val Lys Gly Arg Phe Thr Ile Ser Arg Asp Xaa Xaa Lys Xaa Xaa
65                  70                  75                  80

Xaa Tyr Leu Gln Met Asn Ser Leu Xaa Xaa Glu Asp Thr Ala Xaa Tyr
                85                  90                  95

Tyr Cys Xaa Arg Val Ser Asn Trp Ala Phe Asp Tyr Trp Gly Gln Gly
            100                 105                 110

Thr Xaa Xaa Thr Val Ser Ser
        115

<210> SEQ ID NO 3
<211> LENGTH: 112
<212> TYPE: PRT
<213> ORGANISM: Artificial Sequence
<220> FEATURE:
<223> OTHER INFORMATION: OGD201 Consensus sequence for second humanized
      VL sequence
<220> FEATURE:
<221> NAME/KEY: MISC_FEATURE
```

```
<222> LOCATION: (1)..(1)
<223> OTHER INFORMATION: X=D or E
<220> FEATURE:
<221> NAME/KEY: MISC_FEATURE
<222> LOCATION: (9)..(9)
<223> OTHER INFORMATION: X=L or A
<220> FEATURE:
<221> NAME/KEY: MISC_FEATURE
<222> LOCATION: (10)..(10)
<223> OTHER INFORMATION: X=S or T
<220> FEATURE:
<221> NAME/KEY: MISC_FEATURE
<222> LOCATION: (12)..(12)
<223> OTHER INFORMATION: X=P or S
<220> FEATURE:
<221> NAME/KEY: MISC_FEATURE
<222> LOCATION: (13)..(13)
<223> OTHER INFORMATION: X=V or L or A
<220> FEATURE:
<221> NAME/KEY: MISC_FEATURE
<222> LOCATION: (14)..(14)
<223> OTHER INFORMATION: X=S or T
<220> FEATURE:
<221> NAME/KEY: MISC_FEATURE
<222> LOCATION: (15)..(15)
<223> OTHER INFORMATION: X=L or P or V
<220> FEATURE:
<221> NAME/KEY: MISC_FEATURE
<222> LOCATION: (17)..(17)
<223> OTHER INFORMATION: X=D or Q or E
<220> FEATURE:
<221> NAME/KEY: MISC_FEATURE
<222> LOCATION: (18)..(18)
<223> OTHER INFORMATION: X=Q or P or R
<220> FEATURE:
<221> NAME/KEY: MISC_FEATURE
<222> LOCATION: (19)..(19)
<223> OTHER INFORMATION: X=A or V
<220> FEATURE:
<221> NAME/KEY: MISC_FEATURE
<222> LOCATION: (20)..(20)
<223> OTHER INFORMATION: X=S or T
<220> FEATURE:
<221> NAME/KEY: MISC_FEATURE
<222> LOCATION: (21)..(21)
<223> OTHER INFORMATION: X=I or L
<220> FEATURE:
<221> NAME/KEY: MISC_FEATURE
<222> LOCATION: (22)..(22)
<223> OTHER INFORMATION: X=S or T
<220> FEATURE:
<221> NAME/KEY: MISC_FEATURE
<222> LOCATION: (25)..(25)
<223> OTHER INFORMATION: X=S or A
<220> FEATURE:
<221> NAME/KEY: MISC_FEATURE
<222> LOCATION: (29)..(29)
<223> OTHER INFORMATION: X=L or V
<220> FEATURE:
<221> NAME/KEY: MISC_FEATURE
<222> LOCATION: (30)..(30)
<223> OTHER INFORMATION: X=L or V
<220> FEATURE:
<221> NAME/KEY: MISC_FEATURE
<222> LOCATION: (32)..(32)
<223> OTHER INFORMATION: X=N or S
<220> FEATURE:
<221> NAME/KEY: MISC_FEATURE
<222> LOCATION: (33)..(33)
<223> OTHER INFORMATION: X=N or Q or D
<220> FEATURE:
<221> NAME/KEY: MISC_FEATURE
<222> LOCATION: (34)..(34)
<223> OTHER INFORMATION: X=G or A or S
<220> FEATURE:
<221> NAME/KEY: MISC_FEATURE
<222> LOCATION: (35)..(35)
<223> OTHER INFORMATION: X=N or Y or S
<220> FEATURE:
```

```
-continued

<221> NAME/KEY: MISC_FEATURE
<222> LOCATION: (36)..(36)
<223> OTHER INFORMATION: X=N or T or S
<220> FEATURE:
<221> NAME/KEY: MISC_FEATURE
<222> LOCATION: (37)..(37)
<223> OTHER INFORMATION: X=F or Y
<220> FEATURE:
<221> NAME/KEY: MISC_FEATURE
<222> LOCATION: (39)..(39)
<223> OTHER INFORMATION: X= H or N or S or A or D or Y or G
<220> FEATURE:
<221> NAME/KEY: MISC_FEATURE
<222> LOCATION: (41)..(41)
<223> OTHER INFORMATION: X=Y or F
<220> FEATURE:
<221> NAME/KEY: MISC_FEATURE
<222> LOCATION: (42)..(42)
<223> OTHER INFORMATION: X=L or Q
<220> FEATURE:
<221> NAME/KEY: MISC_FEATURE
<222> LOCATION: (44)..(44)
<223> OTHER INFORMATION: X=K or R
<220> FEATURE:
<221> NAME/KEY: MISC_FEATURE
<222> LOCATION: (47)..(47)
<223> OTHER INFORMATION: X=Q or K
<220> FEATURE:
<221> NAME/KEY: MISC_FEATURE
<222> LOCATION: (48)..(48)
<223> OTHER INFORMATION: X=S or A or V
<220> FEATURE:
<221> NAME/KEY: MISC_FEATURE
<222> LOCATION: (50)..(50)
<223> OTHER INFORMATION: X=K or Q or R
<220> FEATURE:
<221> NAME/KEY: MISC_FEATURE
<222> LOCATION: (51)..(51)
<223> OTHER INFORMATION: X=L or R or V
<220> FEATURE:
<221> NAME/KEY: MISC_FEATURE
<222> LOCATION: (55)..(55)
<223> OTHER INFORMATION: X=K or G or L
<220> FEATURE:
<221> NAME/KEY: MISC_FEATURE
<222> LOCATION: (56)..(56)
<223> OTHER INFORMATION: X= V or A or G
<220> FEATURE:
<221> NAME/KEY: MISC_FEATURE
<222> LOCATION: (58)..(58)
<223> OTHER INFORMATION: X= N or T
<220> FEATURE:
<221> NAME/KEY: MISC_FEATURE
<222> LOCATION: (60)..(60)
<223> OTHER INFORMATION: X= L or D or A
<220> FEATURE:
<221> NAME/KEY: MISC_FEATURE
<222> LOCATION: (61)..(61)
<223> OTHER INFORMATION: X=S or T
<220> FEATURE:
<221> NAME/KEY: MISC_FEATURE
<222> LOCATION: (63)..(63)
<223> OTHER INFORMATION: X=V or I
<220> FEATURE:
<221> NAME/KEY: MISC_FEATURE
<222> LOCATION: (65)..(65)
<223> OTHER INFORMATION: X=D or A or S
<220> FEATURE:
<221> NAME/KEY: MISC_FEATURE
<222> LOCATION: (75)..(75)
<223> OTHER INFORMATION: X=Y or D
<220> FEATURE:
<221> NAME/KEY: MISC_FEATURE
<222> LOCATION: (79)..(79)
<223> OTHER INFORMATION: X=K or T
<220> FEATURE:
<221> NAME/KEY: MISC_FEATURE
<222> LOCATION: (81)..(81)
<223> OTHER INFORMATION: X=S or N
```

```
<220> FEATURE:
<221> NAME/KEY: MISC_FEATURE
<222> LOCATION: (82)..(82)
<223> OTHER INFORMATION: X=R or S
<220> FEATURE:
<221> NAME/KEY: MISC_FEATURE
<222> LOCATION: (83)..(83)
<223> OTHER INFORMATION: X=V or L
<220> FEATURE:
<221> NAME/KEY: MISC_FEATURE
<222> LOCATION: (84)..(84)
<223> OTHER INFORMATION: X=E or Q
<220> FEATURE:
<221> NAME/KEY: MISC_FEATURE
<222> LOCATION: (85)..(85)
<223> OTHER INFORMATION: X=A or P
<220> FEATURE:
<221> NAME/KEY: MISC_FEATURE
<222> LOCATION: (88)..(88)
<223> OTHER INFORMATION: X=L or V or F
<220> FEATURE:
<221> NAME/KEY: MISC_FEATURE
<222> LOCATION: (89)..(89)
<223> OTHER INFORMATION: X=G or A
<220> FEATURE:
<221> NAME/KEY: MISC_FEATURE
<222> LOCATION: (90)..(90)
<223> OTHER INFORMATION: X=V or T
<220> FEATURE:
<221> NAME/KEY: MISC_FEATURE
<222> LOCATION: (92)..(92)
<223> OTHER INFORMATION: X=Y or F
<220> FEATURE:
<221> NAME/KEY: misc_feature
<222> LOCATION: (94)..(94)
<223> OTHER INFORMATION: Xaa can be any naturally occurring amino acid
<220> FEATURE:
<221> NAME/KEY: MISC_FEATURE
<222> LOCATION: (96)..(96)
<223> OTHER INFORMATION: X=S or G or A
<220> FEATURE:
<221> NAME/KEY: MISC_FEATURE
<222> LOCATION: (97)..(97)
<223> OTHER INFORMATION: X=T or Y or L
<220> FEATURE:
<221> NAME/KEY: MISC_FEATURE
<222> LOCATION: (98)..(98)
<223> OTHER INFORMATION: X=H or Q or N
<220> FEATURE:
<221> NAME/KEY: MISC_FEATURE
<222> LOCATION: (98)..(98)
<223> OTHER INFORMATION: X=H or Q or N
<220> FEATURE:
<221> NAME/KEY: MISC_FEATURE
<222> LOCATION: (99)..(99)
<223> OTHER INFORMATION: X= I or W or T
<220> FEATURE:
<221> NAME/KEY: MISC_FEATURE
<222> LOCATION: (100)..(100)
<223> OTHER INFORMATION: X= P or S
<220> FEATURE:
<221> NAME/KEY: MISC_FEATURE
<222> LOCATION: (105)..(105)
<223> OTHER INFORMATION: X=G or Q

<400> SEQUENCE: 3

Xaa Val Val Met Thr Gln Ser Pro Xaa Xaa Leu Xaa Xaa Xaa Xaa Gly
1               5                   10                  15

Xaa Xaa Xaa Xaa Xaa Xaa Cys Arg Xaa Ser Gln Ser Xaa Xaa Lys Xaa
            20                  25                  30

Xaa Xaa Xaa Xaa Xaa Leu Xaa Trp Xaa Xaa Gln Xaa Pro Gly Xaa Xaa
        35                  40                  45

Pro Xaa Xaa Leu Ile Tyr Xaa Xaa Ser Xaa Arg Xaa Xaa Gly Xaa Pro
    50                  55                  60
```

```
Xaa Arg Phe Ser Gly Ser Gly Ser Gly Thr Xaa Phe Thr Leu Xaa Ile
 65                  70                  75                  80

Xaa Xaa Xaa Xaa Xaa Glu Asp Xaa Xaa Xaa Tyr Xaa Cys Xaa Gln Xaa
                 85                  90                  95

Xaa Xaa Xaa Xaa Tyr Thr Phe Gly Xaa Gly Thr Lys Val Glu Ile Lys
            100                 105                 110
```

<210> SEQ ID NO 4
<211> LENGTH: 112
<212> TYPE: PRT
<213> ORGANISM: Artificial Sequence
<220> FEATURE:
<223> OTHER INFORMATION: OGD201 VL15

<400> SEQUENCE: 4

```
Asp Val Val Met Thr Gln Ser Pro Leu Ser Leu Pro Val Thr Leu Gly
  1               5                  10                  15

Gln Pro Ala Ser Ile Ser Cys Arg Ser Ser Gln Ser Leu Val Lys Asn
             20                  25                  30

Gln Ala Asn Thr Tyr Leu His Trp Phe Gln Gln Arg Pro Gly Gln Ser
         35                  40                  45

Pro Arg Leu Leu Ile Tyr Lys Val Ser Asn Arg Leu Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95

Thr His Ile Pro Tyr Thr Phe Gly Gly Gly Thr Lys Val Glu Ile Lys
            100                 105                 110
```

<210> SEQ ID NO 5
<211> LENGTH: 112
<212> TYPE: PRT
<213> ORGANISM: Artificial Sequence
<220> FEATURE:
<223> OTHER INFORMATION: OGD201 VL16

<400> SEQUENCE: 5

```
Glu Val Val Met Thr Gln Ser Pro Ala Thr Leu Ser Leu Thr Pro Gly
  1               5                  10                  15

Gln Pro Ala Thr Leu Ser Cys Arg Ser Ser Gln Ser Leu Val Lys Asn
             20                  25                  30

Gln Ala Asn Thr Tyr Leu His Trp Phe Gln Gln Arg Pro Gly Gln Ala
         35                  40                  45

Pro Arg Leu Leu Ile Tyr Lys Val Ser Asn Arg Leu Thr Gly Ile Pro
 50                  55                  60

Ala Arg Phe Ser Gly Ser Gly Ser Gly Thr Asp Phe Thr Leu Thr Ile
 65                  70                  75                  80

Ser Ser Leu Gln Pro Glu Asp Val Ala Val Tyr Tyr Cys Ser Gln Ser
                 85                  90                  95

Thr His Ile Pro Tyr Thr Phe Gly Gly Gly Thr Lys Val Glu Ile Lys
            100                 105                 110
```

<210> SEQ ID NO 6
<211> LENGTH: 112
<212> TYPE: PRT
<213> ORGANISM: Artificial Sequence
<220> FEATURE:
<223> OTHER INFORMATION: OGD201 VL17

-continued

<400> SEQUENCE: 6

Glu Val Val Met Thr Gln Ser Pro Ala Thr Leu Ser Leu Ser Pro Gly
1               5                   10                  15

Glu Arg Ala Thr Leu Ser Cys Arg Ser Ser Gln Ser Leu Val Lys Asn
            20                  25                  30

Gln Ala Asn Thr Tyr Leu His Trp Tyr Gln Gln Lys Pro Gly Gln Ala
        35                  40                  45

Pro Arg Leu Leu Ile Tyr Lys Val Ser Asn Arg Leu Thr Gly Ile Pro
    50                  55                  60

Ala Arg Phe Ser Gly Ser Gly Ser Gly Thr Asp Phe Thr Leu Thr Ile
65                  70                  75                  80

Ser Ser Leu Gln Ala Glu Asp Phe Ala Val Tyr Tyr Cys Ser Gln Ser
                85                  90                  95

Thr His Ile Pro Tyr Thr Phe Gly Gly Gly Thr Lys Val Glu Ile Lys
            100                 105                 110

<210> SEQ ID NO 7
<211> LENGTH: 112
<212> TYPE: PRT
<213> ORGANISM: Artificial Sequence
<220> FEATURE:
<223> OTHER INFORMATION: OGD201 VL18

<400> SEQUENCE: 7

Glu Val Val Met Thr Gln Ser Pro Ala Thr Leu Ser Leu Thr Pro Gly
1               5                   10                  15

Glu Arg Ala Thr Leu Ser Cys Arg Ser Ser Gln Ser Leu Val Lys Asn
            20                  25                  30

Gln Ala Asn Thr Tyr Leu His Trp Phe Gln Gln Arg Pro Gly Gln Ala
        35                  40                  45

Pro Arg Leu Leu Ile Tyr Lys Val Ser Asn Arg Leu Thr Gly Ile Pro
    50                  55                  60

Ala Arg Phe Ser Gly Ser Gly Ser Gly Thr Asp Phe Thr Leu Thr Ile
65                  70                  75                  80

Ser Ser Leu Gln Pro Glu Asp Phe Ala Val Tyr Tyr Cys Ser Gln Ser
                85                  90                  95

Thr His Ile Pro Tyr Thr Phe Gly Gly Gly Thr Lys Val Glu Ile Lys
            100                 105                 110

<210> SEQ ID NO 8
<211> LENGTH: 119
<212> TYPE: PRT
<213> ORGANISM: Artificial Sequence
<220> FEATURE:
<223> OTHER INFORMATION: OGD201 Consensus sequence for second humanized
      VH sequence
<220> FEATURE:
<221> NAME/KEY: MISC_FEATURE
<222> LOCATION: (1)..(1)
<223> OTHER INFORMATION: X=E or Q
<220> FEATURE:
<221> NAME/KEY: MISC_FEATURE
<222> LOCATION: (5)..(5)
<223> OTHER INFORMATION: X=V or L
<220> FEATURE:
<221> NAME/KEY: MISC_FEATURE
<222> LOCATION: (13)..(13)
<223> OTHER INFORMATION: X=Q or K
<220> FEATURE:
<221> NAME/KEY: MISC_FEATURE
<222> LOCATION: (16)..(16)
<223> OTHER INFORMATION: X= G or R
<220> FEATURE:

-continued

```
<221> NAME/KEY: MISC_FEATURE
<222> LOCATION: (23)..(23)
<223> OTHER INFORMATION: X= A or T
<220> FEATURE:
<221> NAME/KEY: MISC_FEATURE
<222> LOCATION: (24)..(24)
<223> OTHER INFORMATION: X= T or A
<220> FEATURE:
<221> NAME/KEY: MISC_FEATURE
<222> LOCATION: (48)..(48)
<223> OTHER INFORMATION: X= L or V
<220> FEATURE:
<221> NAME/KEY: MISC_FEATURE
<222> LOCATION: (49)..(49)
<223> OTHER INFORMATION: X= G or S
<220> FEATURE:
<221> NAME/KEY: MISC_FEATURE
<222> LOCATION: (57)..(57)
<223> OTHER INFORMATION: X= G or A
<220> FEATURE:
<221> NAME/KEY: MISC_FEATURE
<222> LOCATION: (63)..(63)
<223> OTHER INFORMATION: X= N or A
<220> FEATURE:
<221> NAME/KEY: MISC_FEATURE
<222> LOCATION: (64)..(64)
<223> OTHER INFORMATION: X= P or A
<220> FEATURE:
<221> NAME/KEY: MISC_FEATURE
<222> LOCATION: (77)..(77)
<223> OTHER INFORMATION: X= S or A
<220> FEATURE:
<221> NAME/KEY: MISC_FEATURE
<222> LOCATION: (79)..(79)
<223> OTHER INFORMATION: X= S or N
<220> FEATURE:
<221> NAME/KEY: MISC_FEATURE
<222> LOCATION: (80)..(80)
<223> OTHER INFORMATION: X= I or S or T
<220> FEATURE:
<221> NAME/KEY: MISC_FEATURE
<222> LOCATION: (81)..(81)
<223> OTHER INFORMATION: X= L or T
<220> FEATURE:
<221> NAME/KEY: MISC_FEATURE
<222> LOCATION: (89)..(89)
<223> OTHER INFORMATION: X= R or K or Q
<220> FEATURE:
<221> NAME/KEY: MISC_FEATURE
<222> LOCATION: (90)..(90)
<223> OTHER INFORMATION: X= T or A
<220> FEATURE:
<221> NAME/KEY: MISC_FEATURE
<222> LOCATION: (95)..(95)
<223> OTHER INFORMATION: X= V or I
<220> FEATURE:
<221> NAME/KEY: MISC_FEATURE
<222> LOCATION: (114)..(114)
<223> OTHER INFORMATION: X= T or L
<220> FEATURE:
<221> NAME/KEY: MISC_FEATURE
<222> LOCATION: (115)..(115)
<223> OTHER INFORMATION: X= L or V

<400> SEQUENCE: 8

Xaa Val Gln Leu Xaa Glu Ser Gly Gly Gly Leu Val Xaa Pro Gly Xaa
1               5                   10                  15

Ser Leu Arg Leu Ser Cys Xaa Xaa Ser Glu Phe Thr Phe Thr Asp Tyr
            20                  25                  30

Tyr Met Thr Trp Val Arg Gln Ala Pro Gly Lys Gly Leu Glu Trp Xaa
        35                  40                  45

Xaa Phe Ile Arg Asn Arg Ala Asn Xaa Tyr Thr Thr Glu Tyr Xaa Xaa
    50                  55                  60

Ser Val Lys Gly Arg Phe Thr Ile Ser Arg Asp Asn Xaa Lys Xaa Xaa
```

```
                 65                  70                  75                  80
Xaa Tyr Leu Gln Met Asn Ser Leu Xaa Xaa Glu Asp Thr Ala Xaa Tyr
                     85                  90                  95

Tyr Cys Ala Arg Val Ser Asn Trp Ala Phe Asp Tyr Trp Gly Gln Gly
                100                 105                 110

Thr Xaa Xaa Thr Val Ser Ser
        115

<210> SEQ ID NO 9
<211> LENGTH: 119
<212> TYPE: PRT
<213> ORGANISM: Artificial Sequence
<220> FEATURE:
<223> OTHER INFORMATION: OGD201 VH19

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Glu Phe Thr Phe Thr Asp Tyr
                20                  25                  30

Tyr Met Thr Trp Val Arg Gln Ala Pro Gly Lys Gly Leu Glu Trp Val
                35                  40                  45

Gly Phe Ile Arg Asn Arg Ala Asn Ala Tyr Thr Thr Glu Tyr Ala Ala
            50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                    85                  90                  95

Tyr Cys Ala Arg Val Ser Asn Trp Ala Phe Asp Tyr Trp Gly Gln Gly
                100                 105                 110

Thr Leu Val Thr Val Ser Ser
        115

<210> SEQ ID NO 10
<211> LENGTH: 119
<212> TYPE: PRT
<213> ORGANISM: Artificial Sequence
<220> FEATURE:
<223> OTHER INFORMATION: OGD201 VH20

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Glu Phe Thr Phe Thr Asp Tyr
                20                  25                  30

Tyr Met Thr Trp Val Arg Gln Ala Pro Gly Lys Gly Leu Glu Trp Leu
                35                  40                  45

Gly Phe Ile Arg Asn Arg Ala Asn Ala Tyr Thr Thr Glu Tyr Ala Ala
            50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                    85                  90                  95

Tyr Cys Ala Arg Val Ser Asn Trp Ala Phe Asp Tyr Trp Gly Gln Gly
                100                 105                 110

Thr Leu Val Thr Val Ser Ser
        115
```

```
<210> SEQ ID NO 11
<211> LENGTH: 119
<212> TYPE: PRT
<213> ORGANISM: Artificial Sequence
<220> FEATURE:
<223> OTHER INFORMATION: OGD201 VH21

<400> SEQUENCE: 11

Glu Val Gln Leu Val Glu Ser Gly Gly Gly Leu Val Gln Pro Gly Arg
1               5                   10                  15

Ser Leu Arg Leu Ser Cys Thr Ala Ser Glu Phe Thr Phe Thr Asp Tyr
            20                  25                  30

Tyr Met Thr Trp Val Arg Gln Ala Pro Gly Lys Gly Leu Glu Trp Leu
        35                  40                  45

Gly Phe Ile Arg Asn Arg Ala Asn Ala Tyr Thr Thr Glu Tyr Ala Ala
    50                  55                  60

Ser Val Lys Gly Arg Phe Thr Ile Ser Arg Asp Asn Ser Lys Ser Ile
65                  70                  75                  80

Leu Tyr Leu Gln Met Asn Ser Leu Lys Thr Glu Asp Thr Ala Val Tyr
                85                  90                  95

Tyr Cys Ala Arg Val Ser Asn Trp Ala Phe Asp Tyr Trp Gly Gln Gly
            100                 105                 110

Thr Leu Val Thr Val Ser Ser
        115

<210> SEQ ID NO 12
<211> LENGTH: 112
<212> TYPE: PRT
<213> ORGANISM: Artificial Sequence
<220> FEATURE:
<223> OTHER INFORMATION: OGD201 Consensus sequence for first humanized
      VL sequence
<220> FEATURE:
<221> NAME/KEY: MISC_FEATURE
<222> LOCATION: (1)..(1)
<223> OTHER INFORMATION: X = D or E
<220> FEATURE:
<221> NAME/KEY: MISC_FEATURE
<222> LOCATION: (3)..(3)
<223> OTHER INFORMATION: X = V or Q
<220> FEATURE:
<221> NAME/KEY: MISC_FEATURE
<222> LOCATION: (9)..(9)
<223> OTHER INFORMATION: X = L or A
<220> FEATURE:
<221> NAME/KEY: MISC_FEATURE
<222> LOCATION: (10)..(10)
<223> OTHER INFORMATION: X = S or T
<220> FEATURE:
<221> NAME/KEY: MISC_FEATURE
<222> LOCATION: (12)..(12)
<223> OTHER INFORMATION: X = P or S
<220> FEATURE:
<221> NAME/KEY: MISC_FEATURE
<222> LOCATION: (13)..(13)
<223> OTHER INFORMATION: X = V or L or A
<220> FEATURE:
<221> NAME/KEY: MISC_FEATURE
<222> LOCATION: (14)..(14)
<223> OTHER INFORMATION: X = S or T
<220> FEATURE:
<221> NAME/KEY: MISC_FEATURE
<222> LOCATION: (15)..(15)
<223> OTHER INFORMATION: X = L or P or V
<220> FEATURE:
<221> NAME/KEY: MISC_FEATURE
<222> LOCATION: (17)..(17)
<223> OTHER INFORMATION: X = D or Q or E
<220> FEATURE:
```

```
<221> NAME/KEY: MISC_FEATURE
<222> LOCATION: (18)..(18)
<223> OTHER INFORMATION: X =Q or P or R
<220> FEATURE:
<221> NAME/KEY: MISC_FEATURE
<222> LOCATION: (19)..(19)
<223> OTHER INFORMATION: X = A or V
<220> FEATURE:
<221> NAME/KEY: MISC_FEATURE
<222> LOCATION: (20)..(20)
<223> OTHER INFORMATION: X = S or T
<220> FEATURE:
<221> NAME/KEY: MISC_FEATURE
<222> LOCATION: (21)..(21)
<223> OTHER INFORMATION: X = I or L
<220> FEATURE:
<221> NAME/KEY: MISC_FEATURE
<222> LOCATION: (22)..(22)
<223> OTHER INFORMATION: X = S or T
<220> FEATURE:
<221> NAME/KEY: MISC_FEATURE
<222> LOCATION: (42)..(42)
<223> OTHER INFORMATION: X = L or Q
<220> FEATURE:
<221> NAME/KEY: MISC_FEATURE
<222> LOCATION: (44)..(44)
<223> OTHER INFORMATION: X = K or R
<220> FEATURE:
<221> NAME/KEY: MISC_FEATURE
<222> LOCATION: (47)..(47)
<223> OTHER INFORMATION: X = Q or K
<220> FEATURE:
<221> NAME/KEY: MISC_FEATURE
<222> LOCATION: (48)..(48)
<223> OTHER INFORMATION: X = S or A
<220> FEATURE:
<221> NAME/KEY: MISC_FEATURE
<222> LOCATION: (50)..(50)
<223> OTHER INFORMATION: X = K or Q or R
<220> FEATURE:
<221> NAME/KEY: MISC_FEATURE
<222> LOCATION: (61)..(61)
<223> OTHER INFORMATION: X = S or T
<220> FEATURE:
<221> NAME/KEY: MISC_FEATURE
<222> LOCATION: (63)..(63)
<223> OTHER INFORMATION: X = V or I
<220> FEATURE:
<221> NAME/KEY: MISC_FEATURE
<222> LOCATION: (65)..(65)
<223> OTHER INFORMATION: X =D or A or S
<220> FEATURE:
<221> NAME/KEY: MISC_FEATURE
<222> LOCATION: (75)..(75)
<223> OTHER INFORMATION: X =Y or D
<220> FEATURE:
<221> NAME/KEY: MISC_FEATURE
<222> LOCATION: (79)..(79)
<223> OTHER INFORMATION: X =K or T
<220> FEATURE:
<221> NAME/KEY: MISC_FEATURE
<222> LOCATION: (82)..(82)
<223> OTHER INFORMATION: X = R or S
<220> FEATURE:
<221> NAME/KEY: MISC_FEATURE
<222> LOCATION: (83)..(83)
<223> OTHER INFORMATION: X = V or L
<220> FEATURE:
<221> NAME/KEY: MISC_FEATURE
<222> LOCATION: (84)..(84)
<223> OTHER INFORMATION: X = E or Q
<220> FEATURE:
<221> NAME/KEY: MISC_FEATURE
<222> LOCATION: (85)..(85)
<223> OTHER INFORMATION: X = A or P
<220> FEATURE:
<221> NAME/KEY: MISC_FEATURE
<222> LOCATION: (88)..(88)
<223> OTHER INFORMATION: X = L or V or F
```

```
<220> FEATURE:
<221> NAME/KEY: MISC_FEATURE
<222> LOCATION: (89)..(89)
<223> OTHER INFORMATION: X = G or A
<220> FEATURE:
<221> NAME/KEY: MISC_FEATURE
<222> LOCATION: (90)..(90)
<223> OTHER INFORMATION: X = V or T
<220> FEATURE:
<221> NAME/KEY: MISC_FEATURE
<222> LOCATION: (92)..(92)
<223> OTHER INFORMATION: X = Y or F
<220> FEATURE:
<221> NAME/KEY: MISC_FEATURE
<222> LOCATION: (105)..(105)
<223> OTHER INFORMATION: X = G or Q

<400> SEQUENCE: 12

Xaa Val Xaa Met Thr Gln Ser Pro Xaa Xaa Leu Xaa Xaa Xaa Xaa Gly
 1               5                  10                  15

Xaa Xaa Xaa Xaa Xaa Xaa Cys Arg Ser Ser Gln Ser Leu Leu Lys Asn
             20                  25                  30

Asn Gly Asn Thr Phe Leu His Trp Tyr Xaa Gln Xaa Pro Gly Xaa Xaa
         35                  40                  45

Pro Xaa Leu Leu Ile Tyr Lys Val Ser Asn Arg Leu Xaa Gly Xaa Pro
     50                  55                  60

Xaa Arg Phe Ser Gly Ser Gly Ser Gly Thr Xaa Phe Thr Leu Xaa Ile
65                  70                  75                  80

Ser Xaa Xaa Xaa Xaa Glu Asp Xaa Xaa Xaa Tyr Xaa Cys Ser Gln Ser
             85                  90                  95

Thr His Ile Pro Tyr Thr Phe Gly Xaa Gly Thr Lys Val Glu Ile Lys
            100                 105                 110

<210> SEQ ID NO 13
<211> LENGTH: 119
<212> TYPE: PRT
<213> ORGANISM: Artificial Sequence
<220> FEATURE:
<223> OTHER INFORMATION: OGD201 Consensus sequence for first humanized
      VH sequence
<220> FEATURE:
<221> NAME/KEY: MISC_FEATURE
<222> LOCATION: (1)..(1)
<223> OTHER INFORMATION: X = E or Q
<220> FEATURE:
<221> NAME/KEY: MISC_FEATURE
<222> LOCATION: (13)..(13)
<223> OTHER INFORMATION: X = Q or K
<220> FEATURE:
<221> NAME/KEY: MISC_FEATURE
<222> LOCATION: (16)..(16)
<223> OTHER INFORMATION: X = G or R
<220> FEATURE:
<221> NAME/KEY: MISC_FEATURE
<222> LOCATION: (23)..(23)
<223> OTHER INFORMATION: X = A or T
<220> FEATURE:
<221> NAME/KEY: MISC_FEATURE
<222> LOCATION: (77)..(77)
<223> OTHER INFORMATION: X = S or A
<220> FEATURE:
<221> NAME/KEY: MISC_FEATURE
<222> LOCATION: (79)..(79)
<223> OTHER INFORMATION: X = S or N
<220> FEATURE:
<221> NAME/KEY: MISC_FEATURE
<222> LOCATION: (80)..(80)
<223> OTHER INFORMATION: X = I or S
<220> FEATURE:
<221> NAME/KEY: MISC_FEATURE
<222> LOCATION: (89)..(89)
```

```
<223> OTHER INFORMATION: X = R or K
<220> FEATURE:
<221> NAME/KEY: MISC_FEATURE
<222> LOCATION: (90)..(90)
<223> OTHER INFORMATION: X = T or A

<400> SEQUENCE: 13

Xaa Val Gln Leu Val Glu Ser Gly Gly Gly Leu Val Xaa Pro Gly Xaa
1               5                   10                  15

Ser Leu Arg Leu Ser Cys Xaa Thr Ser Glu Phe Thr Phe Thr Asp Tyr
            20                  25                  30

Tyr Met Thr Trp Val Arg Gln Ala Pro Gly Lys Gly Leu Glu Trp Leu
        35                  40                  45

Gly Phe Ile Arg Asn Arg Ala Asn Gly Tyr Thr Thr Glu Tyr Asn Pro
    50                  55                  60

Ser Val Lys Gly Arg Phe Thr Ile Ser Arg Asp Asn Xaa Lys Xaa Xaa
65                  70                  75                  80

Leu Tyr Leu Gln Met Asn Ser Leu Xaa Xaa Glu Asp Thr Ala Val Tyr
                85                  90                  95

Tyr Cys Ala Arg Val Ser Asn Trp Ala Phe Asp Tyr Trp Gly Gln Gly
            100                 105                 110

Thr Thr Leu Thr Val Ser Ser
            115

<210> SEQ ID NO 14
<211> LENGTH: 112
<212> TYPE: PRT
<213> ORGANISM: Mus musculus

<400> SEQUENCE: 14

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Asn
            20                  25                  30

Asn Gly Asn Thr Phe Leu His Trp Tyr Leu Gln Lys Ser Gly Gln Ser
        35                  40                  45

Pro Lys Leu Leu Ile Tyr Lys Val Ser Asn Arg Leu Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Ser Gln Ser
                85                  90                  95

Thr His Ile Pro Tyr Thr Phe Gly Gly Gly Thr Lys Leu Glu Ile Lys
            100                 105                 110

<210> SEQ ID NO 15
<211> LENGTH: 119
<212> TYPE: PRT
<213> ORGANISM: Mus musculus

<400> SEQUENCE: 15

Glu Val Lys Leu Val Glu Ser Gly Gly Gly Leu Val Leu Pro Gly Asp
1               5                   10                  15

Ser Leu Arg Leu Ser Cys Ala Thr Ser Glu Phe Thr Phe Thr Asp Tyr
            20                  25                  30

Tyr Met Thr Trp Val Arg Gln Pro Pro Arg Lys Ala Leu Glu Trp Leu
        35                  40                  45

Gly Phe Ile Arg Asn Arg Ala Asn Gly Tyr Thr Thr Glu Tyr Asn Pro
```

```
                    50                  55                  60
Ser Val Lys Gly Arg Phe Thr Ile Ser Arg Asp Asn Ser Gln Ser Ile
 65                  70                  75                  80

Leu Tyr Leu Gln Met Asn Thr Leu Arg Thr Glu Asp Ser Ala Thr Tyr
                 85                  90                  95

Tyr Cys Ala Arg Val Ser Asn Trp Ala Phe Asp Tyr Trp Gly Gln Gly
            100                 105                 110

Thr Thr Leu Thr Val Ser Ser
        115

<210> SEQ ID NO 16
<211> LENGTH: 10
<212> TYPE: PRT
<213> ORGANISM: Artificial Sequence
<220> FEATURE:
<223> OTHER INFORMATION: CDR1_VH

<400> SEQUENCE: 16

Glu Phe Thr Phe Thr Asp Tyr Tyr Met Thr
 1               5                  10

<210> SEQ ID NO 17
<211> LENGTH: 19
<212> TYPE: PRT
<213> ORGANISM: Artificial Sequence
<220> FEATURE:
<223> OTHER INFORMATION: CDR2_VH

<400> SEQUENCE: 17

Phe Ile Arg Asn Arg Ala Asn Gly Tyr Thr Thr Glu Tyr Asn Pro Ser
 1               5                  10                  15

Val Lys Gly

<210> SEQ ID NO 18
<211> LENGTH: 10
<212> TYPE: PRT
<213> ORGANISM: Artificial Sequence
<220> FEATURE:
<223> OTHER INFORMATION: CDR3_VH

<400> SEQUENCE: 18

Ala Arg Val Ser Asn Trp Ala Phe Asp Tyr
 1               5                  10

<210> SEQ ID NO 19
<211> LENGTH: 16
<212> TYPE: PRT
<213> ORGANISM: Artificial Sequence
<220> FEATURE:
<223> OTHER INFORMATION: CDR1_VL

<400> SEQUENCE: 19

Arg Ser Ser Gln Ser Leu Leu Lys Asn Asn Gly Asn Thr Phe Leu His
 1               5                  10                  15

<210> SEQ ID NO 20
<211> LENGTH: 7
<212> TYPE: PRT
<213> ORGANISM: Artificial Sequence
<220> FEATURE:
<223> OTHER INFORMATION: CDR2_VL

<400> SEQUENCE: 20

Tyr Lys Val Ser Asn Arg Leu
```

```
<210> SEQ ID NO 21
<211> LENGTH: 9
<212> TYPE: PRT
<213> ORGANISM: Artificial Sequence
<220> FEATURE:
<223> OTHER INFORMATION: CDR3_VL

<400> SEQUENCE: 21

Ser Gln Ser Thr His Ile Pro Tyr Thr
1               5

<210> SEQ ID NO 22
<211> LENGTH: 5
<212> TYPE: PRT
<213> ORGANISM: Artificial Sequence
<220> FEATURE:
<223> OTHER INFORMATION: scFv linker

<400> SEQUENCE: 22

Gly Ser Gly Gly Ser
1               5

<210> SEQ ID NO 23
<211> LENGTH: 4
<212> TYPE: PRT
<213> ORGANISM: Artificial Sequence
<220> FEATURE:
<223> OTHER INFORMATION: scFv linker

<400> SEQUENCE: 23

Gly Gly Gly Ser
1

<210> SEQ ID NO 24
<211> LENGTH: 5
<212> TYPE: PRT
<213> ORGANISM: Artificial Sequence
<220> FEATURE:
<223> OTHER INFORMATION: scFv linker

<400> SEQUENCE: 24

Gly Gly Gly Gly Ser
1               5

<210> SEQ ID NO 25
<211> LENGTH: 15
<212> TYPE: PRT
<213> ORGANISM: Artificial Sequence
<220> FEATURE:
<223> OTHER INFORMATION: ((G4S)3 linker

<400> SEQUENCE: 25

Gly Gly Gly Gly Ser Gly Gly Gly Gly Ser Gly Gly Gly Gly Ser
1               5                   10                  15

<210> SEQ ID NO 26
<211> LENGTH: 18
<212> TYPE: PRT
<213> ORGANISM: Artificial Sequence
<220> FEATURE:
<223> OTHER INFORMATION: CD19 linker

<400> SEQUENCE: 26

Gly Ser Thr Ser Gly Ser Gly Lys Pro Gly Ser Gly Glu Gly Ser Thr
1               5                   10                  15
```

Lys Gly

<210> SEQ ID NO 27
<211> LENGTH: 18
<212> TYPE: PRT
<213> ORGANISM: Artificial Sequence
<220> FEATURE:
<223> OTHER INFORMATION: 18mer

<400> SEQUENCE: 27

Gly Gly Ser Ser Arg Ser Ser Ser Gly Gly Gly Ser Gly Gly
1               5                   10                  15

Gly Gly

<210> SEQ ID NO 28
<211> LENGTH: 20
<212> TYPE: PRT
<213> ORGANISM: Artificial Sequence
<220> FEATURE:
<223> OTHER INFORMATION: (G4S)4 linker

<400> SEQUENCE: 28

Gly Gly Gly Gly Ser Gly Gly Gly Gly Ser Gly Gly Gly Gly Ser Gly
1               5                   10                  15

Gly Gly Gly Ser
            20

<210> SEQ ID NO 29
<211> LENGTH: 18
<212> TYPE: PRT
<213> ORGANISM: Artificial Sequence
<220> FEATURE:
<223> OTHER INFORMATION: linker

<400> SEQUENCE: 29

Lys Glu Ser Gly Ser Val Ser Ser Glu Gln Leu Ala Gln Phe Arg Ser
1               5                   10                  15

Leu Asp

<210> SEQ ID NO 30
<211> LENGTH: 14
<212> TYPE: PRT
<213> ORGANISM: Artificial Sequence
<220> FEATURE:
<223> OTHER INFORMATION: linker

<400> SEQUENCE: 30

Glu Gly Lys Ser Ser Gly Ser Gly Ser Glu Ser Lys Ser Thr
1               5                   10

<210> SEQ ID NO 31
<211> LENGTH: 12
<212> TYPE: PRT
<213> ORGANISM: Artificial Sequence
<220> FEATURE:
<223> OTHER INFORMATION: linker

<400> SEQUENCE: 31

Gly Ser Ala Gly Ser Ala Ala Gly Ser Gly Glu Phe
1               5                   10

<210> SEQ ID NO 32
<211> LENGTH: 8
<212> TYPE: PRT

```
<213> ORGANISM: Artificial Sequence
<220> FEATURE:
<223> OTHER INFORMATION: linker

<400> SEQUENCE: 32

Gly Gly Gly Gly Gly Gly Gly
1               5

<210> SEQ ID NO 33
<211> LENGTH: 6
<212> TYPE: PRT
<213> ORGANISM: Artificial Sequence
<220> FEATURE:
<223> OTHER INFORMATION: linker

<400> SEQUENCE: 33

Gly Gly Gly Gly Gly Gly
1               5

<210> SEQ ID NO 34
<211> LENGTH: 112
<212> TYPE: PRT
<213> ORGANISM: Artificial Sequence
<220> FEATURE:
<223> OTHER INFORMATION: OGD201 VL1

<400> SEQUENCE: 34

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Lys Asn
            20                  25                  30

Asn Gly Asn Thr Phe Leu His Trp Tyr Gln Gln Arg Pro Gly Gln Ser
        35                  40                  45

Pro Arg Leu Leu Ile Tyr Lys Val Ser Asn Arg Leu Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Ile Pro Tyr Thr Phe Gly Gly Thr Lys Val Glu Ile Lys
            100                 105                 110

<210> SEQ ID NO 35
<211> LENGTH: 112
<212> TYPE: PRT
<213> ORGANISM: Artificial Sequence
<220> FEATURE:
<223> OTHER INFORMATION: OGD201 VL2

<400> SEQUENCE: 35

Glu Val Val Met Thr Gln Ser Pro Ala Thr Leu Ser Leu Ser Pro Gly
1               5                   10                  15

Glu Arg Ala Thr Leu Ser Cys Arg Ser Ser Gln Ser Leu Leu Lys Asn
            20                  25                  30

Asn Gly Asn Thr Phe Leu His Trp Tyr Gln Gln Lys Pro Gly Gln Ala
        35                  40                  45

Pro Arg Leu Leu Ile Tyr Lys Val Ser Asn Arg Leu Thr Gly Ile Pro
    50                  55                  60

Ala Arg Phe Ser Gly Ser Gly Ser Gly Thr Asp Phe Thr Leu Thr Ile
65                  70                  75                  80

Ser Ser Leu Gln Pro Glu Asp Phe Ala Val Tyr Phe Cys Ser Gln Ser
```

```
                    85                  90                  95

Thr His Ile Pro Tyr Thr Phe Gly Gly Gly Thr Lys Val Glu Ile Lys
                100                 105                 110

<210> SEQ ID NO 36
<211> LENGTH: 112
<212> TYPE: PRT
<213> ORGANISM: Artificial Sequence
<220> FEATURE:
<223> OTHER INFORMATION: OGD201 VL3

<400> SEQUENCE: 36

Asp Val Val Met Thr Gln Ser Pro Leu Ser Leu Pro Val Thr Pro Gly
1               5                   10                  15

Glu Pro Ala Ser Ile Ser Cys Arg Ser Gln Ser Leu Leu Lys Asn
            20                  25                  30

Asn Gly Asn Thr Phe Leu His Trp Tyr Leu Gln Lys Pro Gly Gln Ser
        35                  40                  45

Pro Gln Leu Leu Ile Tyr Lys Val Ser Asn Arg Leu Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Ile Pro Tyr Thr Phe Gly Gln Gly Thr Lys Val Glu Ile Lys
                100                 105                 110

<210> SEQ ID NO 37
<211> LENGTH: 112
<212> TYPE: PRT
<213> ORGANISM: Artificial Sequence
<220> FEATURE:
<223> OTHER INFORMATION: OGD201 VL4

<400> SEQUENCE: 37

Asp Val Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Leu Lys Asn
            20                  25                  30

Asn Gly Asn Thr Phe Leu His Trp Tyr Gln Gln Lys Pro Gly Lys Ala
        35                  40                  45

Pro Lys Leu Leu Ile Tyr Lys Val Ser Asn Arg Leu Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Val Ala Thr Tyr Tyr Cys Ser Gln Ser
                85                  90                  95

Thr His Ile Pro Tyr Thr Phe Gly Gln Gly Thr Lys Val Glu Ile Lys
                100                 105                 110

<210> SEQ ID NO 38
<211> LENGTH: 112
<212> TYPE: PRT
<213> ORGANISM: Artificial Sequence
<220> FEATURE:
<223> OTHER INFORMATION: OGD201 VL28BH

<400> SEQUENCE: 38

Asp Val Val Met Thr Gln Ser Pro Leu Ser Leu Pro Val Thr Pro Gly
1               5                   10                  15
```

Glu Pro Ala Ser Ile Ser Cys Arg Ser Ser Gln Ser Leu Leu Lys Asn
                20                  25                  30

Asn Ala Asn Thr Phe Leu His Trp Tyr Leu Gln Lys Pro Gly Gln Ser
            35                  40                  45

Pro Gln Leu Leu Ile Tyr Lys Val Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Ile Pro Tyr Thr Phe Gly Gly Gly Thr Lys Val Glu Ile Lys
            100                 105                 110

<210> SEQ ID NO 39
<211> LENGTH: 112
<212> TYPE: PRT
<213> ORGANISM: Artificial Sequence
<220> FEATURE:
<223> OTHER INFORMATION: OGD201 VL30BH

<400> SEQUENCE: 39

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Lys Asn
                20                  25                  30

Gln Gly Asn Thr Phe Leu His Trp Phe Gln Gln Arg Pro Gly Gln Ser
            35                  40                  45

Pro Arg Leu Leu Ile Tyr Lys Val Ser Asn Arg Leu Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Ile Pro Tyr Thr Phe Gly Gly Gly Thr Lys Val Glu Ile Lys
            100                 105                 110

<210> SEQ ID NO 40
<211> LENGTH: 112
<212> TYPE: PRT
<213> ORGANISM: Artificial Sequence
<220> FEATURE:
<223> OTHER INFORMATION: OGD201 VL28Bs01/A2

<400> SEQUENCE: 40

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Lys Ser
                20                  25                  30

Asn Ala Asn Thr Phe Leu His Trp Tyr Leu Gln Lys Pro Gly Gln Ser
            35                  40                  45

Pro Gln Leu Leu Ile Tyr Lys Val Ser Asn Arg Leu Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Thr His Ile Pro Tyr Thr Phe Gly Gln Gly Thr Lys Val Glu Ile Lys

-continued

```
                   100                 105                 110
```

<210> SEQ ID NO 41
<211> LENGTH: 119
<212> TYPE: PRT
<213> ORGANISM: Artificial Sequence
<220> FEATURE:
<223> OTHER INFORMATION: OGD201 VH1

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Thr Ser Glu Phe Thr Phe Thr Asp Tyr
            20                  25                  30

Tyr Met Thr Trp Val Arg Gln Ala Pro Gly Lys Gly Leu Glu Trp Leu
        35                  40                  45

Gly Phe Ile Arg Asn Arg Ala Asn Gly Tyr Thr Thr Glu Tyr Asn Pro
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Val Ser Asn Trp Ala Phe Asp Tyr Trp Gly Gln Gly
            100                 105                 110

Thr Leu Val Thr Val Ser Ser
        115

<210> SEQ ID NO 42
<211> LENGTH: 119
<212> TYPE: PRT
<213> ORGANISM: Artificial Sequence
<220> FEATURE:
<223> OTHER INFORMATION: OGD201 VH2

<400> SEQUENCE: 42

Glu Val Gln Leu Val Glu Ser Gly Gly Gly Leu Val Gln Pro Gly Arg
1               5                   10                  15

Ser Leu Arg Leu Ser Cys Thr Thr Ser Glu Phe Thr Phe Thr Asp Tyr
            20                  25                  30

Tyr Met Thr Trp Val Arg Gln Ala Pro Gly Lys Gly Leu Glu Trp Leu
        35                  40                  45

Gly Phe Ile Arg Asn Arg Ala Asn Gly Tyr Thr Thr Glu Tyr Asn Pro
    50                  55                  60

Ser Val Lys Gly Arg Phe Thr Ile Ser Arg Asp Asn Ser Lys Ser Ile
65                  70                  75                  80

Leu Tyr Leu Gln Met Asn Ser Leu Lys Thr Glu Asp Thr Ala Val Tyr
                85                  90                  95

Tyr Cys Ala Arg Val Ser Asn Trp Ala Phe Asp Tyr Trp Gly Gln Gly
            100                 105                 110

Thr Leu Val Thr Val Ser Ser
        115

<210> SEQ ID NO 43
<211> LENGTH: 119
<212> TYPE: PRT
<213> ORGANISM: Artificial Sequence
<220> FEATURE:
<223> OTHER INFORMATION: 201 VH3-11*01A

<400> SEQUENCE: 43
```

Gln Val Gln Leu Val Glu Ser Gly Gly Gly Leu Val Lys Pro Gly Gly
1               5                   10                  15

Ser Leu Arg Leu Ser Cys Ala Thr Ser Glu Phe Thr Phe Thr Asp Tyr
            20                  25                  30

Tyr Met Thr Trp Val Arg Gln Ala Pro Gly Lys Gly Leu Glu Trp Leu
        35                  40                  45

Gly Phe Ile Arg Asn Arg Ala Asn Gly Tyr Thr Thr Glu Tyr Asn Pro
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Val Ser Asn Trp Ala Phe Asp Tyr Trp Gly Gln Gly
                100                 105                 110

Thr Leu Val Thr Val Ser Ser
        115

<210> SEQ ID NO 44
<211> LENGTH: 118
<212> TYPE: PRT
<213> ORGANISM: Artificial Sequence
<220> FEATURE:
<223> OTHER INFORMATION: OGD201 VH 72BCDR

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Glu Phe Thr Phe Thr Asp Tyr
            20                  25                  30

Tyr Met Thr Trp Val Arg Gln Ala Pro Gly Lys Gly Leu Glu Trp Leu
        35                  40                  45

Gly Phe Ile Arg Asn Arg Ala Asn Gly Tyr Thr Thr Glu Tyr Asn Pro
    50                  55                  60

Ser Val Lys Gly Arg Phe Thr Ile Ser Arg Asp Asn Ser Lys Asn Ser
65                  70                  75                  80

Leu Tyr Leu Gln Met Asn Leu Lys Thr Glu Asp Thr Ala Val Tyr Tyr
                85                  90                  95

Cys Ala Arg Val Ser Asn Trp Ala Phe Asp Tyr Trp Gly Gln Gly Thr
                100                 105                 110

Leu Val Thr Val Ser Ser
        115

<210> SEQ ID NO 45
<211> LENGTH: 118
<212> TYPE: PRT
<213> ORGANISM: Artificial Sequence
<220> FEATURE:
<223> OTHER INFORMATION: OGD201 72BH

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Thr Ser Glu Phe Thr Phe Ser Asp Tyr
            20                  25                  30

Tyr Met Thr Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ala Ala

```
                     50                  55                  60
Ser Val Lys Gly Arg Phe Thr Ile Ser Arg Asp Asn Ser Lys Asn Ser
 65                  70                  75                  80

Leu Tyr Leu Gln Met Asn Leu Lys Thr Glu Asp Thr Ala Val Tyr Tyr
                     85                  90                  95

Cys Ala Arg Val Ser Asn Trp Ala Phe Asp Tyr Trp Gly Gln Gly Thr
                100                 105                 110

Leu Val Thr Val Ser Ser
            115
```

<210> SEQ ID NO 46
<211> LENGTH: 118
<212> TYPE: PRT
<213> ORGANISM: Artificial Sequence
<220> FEATURE:
<223> OTHER INFORMATION: OGD201 VH49BCDR

<400> SEQUENCE: 46

```
Glu Val Gln Leu Val Glu Ser Gly Gly Gly Leu Val Gln Pro Gly Arg
 1               5                  10                  15

Ser Leu Arg Leu Ser Cys Thr Ala Ser Glu Phe Thr Phe Thr Asp Tyr
                20                  25                  30

Tyr Met Thr Trp Val Arg Gln Ala Pro Gly Lys Gly Leu Glu Trp Leu
            35                  40                  45

Gly Phe Ile Arg Asn Arg Ala Asn Gly Tyr Thr Thr Glu Tyr Ala Ala
        50                  55                  60

Ser Val Lys Gly Arg Phe Thr Ile Ser Arg Asp Asn Ser Lys Ser Ile
 65                  70                  75                  80

Leu Tyr Leu Gln Met Asn Leu Lys Thr Glu Asp Thr Ala Val Tyr Tyr
                     85                  90                  95

Cys Ala Arg Val Ser Asn Trp Ala Phe Asp Tyr Trp Gly Gln Gly Thr
                100                 105                 110

Leu Val Thr Val Ser Ser
            115
```

<210> SEQ ID NO 47
<211> LENGTH: 118
<212> TYPE: PRT
<213> ORGANISM: Artificial Sequence
<220> FEATURE:
<223> OTHER INFORMATION: OGD201 VH49BH

<400> SEQUENCE: 47

```
Glu Val Gln Leu Val Glu Ser Gly Gly Gly Leu Val Gln Pro Gly Arg
 1               5                  10                  15

Ser Leu Arg Leu Ser Cys Thr Ser Glu Phe Thr Phe Thr Asp Tyr
                20                  25                  30

Tyr Met Thr Trp Val Arg Gln Ala Pro Gly Lys Gly Leu Glu Trp Leu
            35                  40                  45

Gly Phe Ile Arg Asn Lys Ala Asn Gly Tyr Thr Thr Glu Tyr Asn Pro
        50                  55                  60

Ser Val Lys Gly Arg Phe Thr Ile Ser Arg Asp Asn Ser Lys Ser Ile
 65                  70                  75                  80

Leu Tyr Leu Gln Met Asn Leu Lys Thr Glu Asp Thr Ala Val Tyr Tyr
                     85                  90                  95

Cys Ala Arg Val Ser Asn Trp Ala Phe Asp Tyr Trp Gly Gln Gly Thr
                100                 105                 110
```

-continued

```
Leu Val Thr Val Ser Ser
        115

<210> SEQ ID NO 48
<211> LENGTH: 119
<212> TYPE: PRT
<213> ORGANISM: Artificial Sequence
<220> FEATURE:
<223> OTHER INFORMATION: OGD201 VH72max

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Tyr Met Thr Trp Val Arg Gln Ala Pro Gly Lys Gly Leu Glu Trp Leu
        35                  40                  45

Gly Phe Ile Arg Asn Lys Ala Asn Ser Tyr Thr Thr Glu Tyr Ala Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Val Ser Asn Trp Ala Phe Asp Tyr Trp Gly Gln Gly
            100                 105                 110

Thr Leu Val Thr Val Ser Ser
        115

<210> SEQ ID NO 49
<211> LENGTH: 119
<212> TYPE: PRT
<213> ORGANISM: Artificial Sequence
<220> FEATURE:
<223> OTHER INFORMATION: OGD201 VH49B

<400> SEQUENCE: 49

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Thr Asp Tyr
            20                  25                  30

Tyr Met Thr Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ala Ala
    50                  55                  60

Ser Val Lys Gly Arg Phe Thr Ile Ser Arg Asp Asn Ser Lys Ser Ile
65                  70                  75                  80

Leu Tyr Leu Gln Met Asn Ser Leu Lys Thr Glu Asp Thr Ala Val Tyr
                85                  90                  95

Tyr Cys Ala Arg Val Ser Asn Trp Ala Phe Asp Tyr Trp Gly Gln Gly
            100                 105                 110

Thr Leu Val Thr Val Ser Ser
        115

<210> SEQ ID NO 50
<211> LENGTH: 119
<212> TYPE: PRT
<213> ORGANISM: Artificial Sequence
<220> FEATURE:
<223> OTHER INFORMATION: OGD201 VH49Bmax
```

-continued

```
<400> SEQUENCE: 50

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Gly Thr Thr Glu Tyr Ala Ala
    50                  55                  60

Ser Val Lys Gly Arg Phe Thr Ile Ser Arg Asp Asn Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Thr Arg Val Ser Asn Trp Ala Phe Asp Tyr Trp Gly Gln Gly
            100                 105                 110

Thr Leu Val Thr Val Ser Ser
            115
```

The invention claimed is:

1. A method for delivery of an anti-cancer agent into a cell expressing the OAcGD2 ganglioside comprising contacting the cell with a composition comprising (i) at least one anti-cancer agent having a molecular mass ranging from 100 Daltons to 200,000 Daltons, and (ii) at least one multimeric antibody or multimeric fragment thereof recognizing the OAcGD2 ganglioside, in an amount and concentration effective to enhance uptake of the anti-cancer agent by the cell, wherein the antibody causes permeability defects within the cell membrane and wherein said multimeric antibody recognizing the OAcGD2 ganglioside comprises a) a light chain variable region (VL) polypeptide having the amino acid sequence SEQ ID NO: 1 and b) a heavy chain variable region (VH) having the amino acid sequence SEQ ID NO: 2.

2. The method of claim 1, wherein the cell expressing the OAcGD2 ganglioside is a cancer cell.

3. The method of claim 1, wherein said method is for further treating cancer expressing the OAcGD2 ganglioside in a patient, comprising administering to a patient in need thereof an effective amount of the composition.

4. A method for delivery of an anti-cancer agent into a cell expressing the OAcGD2 ganglioside comprising contacting the cell with a composition comprising (i) at least one anti-cancer agent having a molecular mass ranging from 100 Daltons to 200,000 Daltons, and (ii) at least one multimeric antibody or multimeric fragment thereof recognizing the OAcGD2 ganglioside in an amount and concentration effective to enhance uptake of the anti-cancer agent by the cell, wherein the antibody causes permeability defects within the cell membrane and wherein the at least one multimeric antibody or multimeric fragment thereof recognizing the OAcGD2 ganglioside comprises:

the light chain variable region (VL) polypeptide having the amino acid sequence selected in the group comprising or consisting of SEQ ID NO: 39 and SEQ ID NO: 40; and the heavy chain variable region (VH) having the amino acid sequence selected in the group comprising or consisting of SEQ ID NO: 48, SEQ ID NO: 49, SEQ ID NO: 50 and SEQ ID NO: 51.

5. The method of claim 1, wherein the multimeric fragment of the antibody recognizing the OAcGD2 ganglioside is in the form of single chain fragments of heavy and light chain variable regions (scFv).

6. The method of claim 1, wherein the multimeric fragment of the antibody recognizing the OAcGD2 ganglioside is a single-chain part of a chimeric antigen receptor (CAR).

7. A method for delivery of an anti-cancer agent into a cell expressing the OAcGD2 ganglioside comprising contacting the cell with a composition comprising (i) at least one anti-cancer agent having a molecular mass ranging from 100 Daltons to 200,000 Daltons, and (ii) at least one multimeric antibody or multimeric fragment thereof recognizing the OAcGD2 ganglioside in an amount and concentration effective to enhance uptake of the anti-cancer agent by the cell, wherein the antibody causes permeability defects within the cell membrane and wherein the at least one multimeric antibody or multimeric fragment thereof recognizing the OAcGD2 ganglioside comprises:

the light chain variable region (VL) polypeptide having the amino acid sequence selected in the group comprising or consisting of SEQ ID NO: 34, SEQ ID NO: 35, SEQ ID NO: 36, SEQ ID NO: 37, SEQ ID NO: 38, SEQ ID NO:39 and SEQ ID NO: 40, and the heavy chain variable region (VH) having the amino acid sequence selected in the group comprising or consisting of SEQ ID NO: 41, SEQ ID NO: 42, SEQ ID NO: 43, SEQ ID NO:44, SEQ ID NO:45, SEQ ID NO:46, SEQ ID NO: 47, SEQ ID NO:48, SEQ ID NO:49, SEQ ID NO:50 and SEQ ID NO: 51.

8. A method for delivery of an anti-cancer agent into a cell expressing the OAcGD2 ganglioside comprising contacting the cell with a composition comprising (i) at least one anti-cancer agent having a molecular mass ranging from 100 Daltons to 200,000 Daltons, and (ii) at least one multimeric antibody or multimeric fragment thereof recognizing the OAcGD2 ganglioside in an amount and concentration effective to enhance uptake of the anti-cancer agent by the cell, wherein the antibody causes permeability defects within the cell membrane and wherein the at least one multimeric antibody or multimeric fragment thereof recognizing the OAcGD2 ganglioside comprises:

a) a light chain variable region (VL) polypeptide having the amino acid sequence SEQ ID NO: 14; and
b) a heavy chain variable region (VH) having the amino acid sequence SEQ ID NO: 15.

9. The method of claim 1, wherein the at least one multimeric antibody or multimeric fragment thereof recognizing the OAcGD2 ganglioside comprises:
   a) a heavy chain comprising three heavy chain complementary regions (CDRs) having the amino acid sequences SEQ ID NO:16, SEQ ID NO:17 and SEQ ID NO:18, and a heavy chain framework sequence from an immunoglobulin heavy chain, and
   b) a light chain comprising three light chain complementary regions (CDRs) having the amino acid sequences SEQ ID NO:19, SEQ ID NO:20 and SEQ ID NO:21, and a light chain framework sequence from an immunoglobulin light chain.

10. The method of claim 1, wherein said at least one multimeric antibody or multimeric fragment thereof recognizing the OAcGD2 ganglioside is an immunoconjugate.

11. The method of claim 1, wherein the at least one anti-cancer agent having a molecular mass ranging from 100 Daltons to 200,000 Daltons is selected from the group comprising or consisting of anti-cancer agents such as alkylating agents, anti-metabolites, anti-tumor antibodies, anti-tumor antibiotics, topoisomerase inhibitors, mitotic inhibitors, tyrosine kinase inhibitors, corticosteroids, hormones or hormone-like drugs, cytokines, nucleoside analogs, nucleic acids, such double-stranded synthetic short RNA molecules (miRNAs) or synthetic DNA/RNA-like oligonucleotides (ASOs).

12. The method of claim 1, wherein the at least one anti-cancer agent having a molecular mass ranging from 100 Daltons to 200,000 Daltons is unable to cross the cell membrane of cancer cells by itself.

13. The method of claim 3, wherein the cancer expressing the OAcGD2 ganglioside is selected from the group comprising or consisting of neuroblastoma, glioma, retinoblastoma, Ewing's family of tumors, sarcoma small cell lung cancer, breast cancer, melanoma, metastatic renal carcinoma, head and neck cancer and hematological cancers.

14. The method of claim 13, wherein the at least one anti-cancer agent is selected from the group comprising or consisting of cyclophosphamide, doxorubicin, topotecan, irinotecan, temozolomide (TMZ), retinoic acid (RA), 5-Fluorouracil (5-FU), fludarabine, carboplatin and cisplatin.

15. The method of claim 3, wherein the at least one anti-cancer agent is temozolomide, topotecan, irinotecan, fludarabine, cyclophosphamide or a mixture thereof and the cancer expressing the OAcGD2 ganglioside is neuroblastoma.

16. The method of claim 3, wherein said method is for further increasing the efficacy of a cancer expressing the OAcGD2 ganglioside treatment comprising an anti-cancer agent, wherein the at least one anti-cancer agent has a molecular mass ranging from 100 Daltons to 200,000 Daltons.

17. The method of claim 3, wherein said method is for further increasing sensitivity to an anti-cancer agent in a patient suffering from a cancer expressing the OAcGD2 ganglioside, wherein the at least one anti-cancer agent has a molecular mass ranging from 100 Daltons to 200,000 Daltons.

18. A method of delaying development of cancer resistant to an anti-cancer agent in a patient suffering from a cancer expressing the OAcGD2 ganglioside, comprising administering to a patient in need thereof an effective amount of a composition comprising: (i) at least one anti-cancer agent having a molecular mass ranging from 100 Daltons to 200,000 Daltons, (ii) at least one multimeric antibody or multimeric fragment thereof recognizing the OAcGD2 ganglioside, wherein the multimeric antibody recognizing the OAcGD2 ganglioside comprises a) a light chain variable region (VL) polypeptide having the amino acid sequence SEQ ID NO: 1 and b) a heavy chain variable region (VH) having the amino acid sequence SEQ ID NO: 2.

* * * * *

UNITED STATES PATENT AND TRADEMARK OFFICE
CERTIFICATE OF CORRECTION

| | | |
|---|---|---|
| PATENT NO. | : 11,697,689 B2 | |
| APPLICATION NO. | : 16/466769 | |
| DATED | : July 11, 2023 | |
| INVENTOR(S) | : Stéphane Birkle et al. | |

It is certified that error appears in the above-identified patent and that said Letters Patent is hereby corrected as shown below:

In the Specification

Please replace the Sequence ID Listing appearing from the end of Column 40 to the top of Column 93 with the following corrected Sequence ID Listing:

SEQUENCE LISTING

<160> 51

<170> BiSSAP 1.3.6

<210> 1
<211> 112
<212> PRT
<213> Artificial Sequence

Signed and Sealed this
Seventh Day of November, 2023

*Katherine Kelly Vidal*

Katherine Kelly Vidal
*Director of the United States Patent and Trademark Office*

```
<220>
<223> OGD201 Consensus sequence for third humanized VL sequence

<220>
<221> SITE
<222> 1
<223> X = D or E

<220>
<221> SITE
<222> 2
<223> X = V or I

<220>
<221> SITE
<222> 9
<223> X = L or A

<220>
<221> SITE
<222> 10
<223> X = S or T

<220>
<221> SITE
<222> 12
<223> X = P or S

<220>
<221> SITE
<222> 13
<223> X = V or L or A

<220>
<221> SITE
<222> 14
<223> X = S or T

<220>
<221> SITE
<222> 15
<223> X = L or P or V

<220>
<221> SITE
<222> 17
<223> X = D or Q or E

<220>
<221> SITE
<222> 18
<223> X = Q or P or R
```

```
<220>
<221> SITE
<222> 19
<223> X = A or V

<220>
<221> SITE
<222> 20
<223> X = S or T

<220>
<221> SITE
<222> 21
<223> X = I or L

<220>
<221> SITE
<222> 22
<223> X = S or T

<220>
<221> SITE
<222> 25
<223> X = S or A

<220>
<221> SITE
<222> 29
<223> X = L or V

<220>
<221> SITE
<222> 30
<223> X = L or V

<220>
<221> SITE
<222> 32
<223> X = N or S

<220>
<221> SITE
<222> 33
<223> X = N or Q

<220>
<221> SITE
<222> 34
<223> X = G or A or S
```

```
<220>
<221> SITE
<222> 35
<223> X = N or Y or S

<220>
<221> SITE
<222> 36
<223> X = T or N or S

<220>
<221> SITE
<222> 37
<223> X = F or Y

<220>
<221> SITE
<222> 39
<223> X = H or N or S or A or Y or G

<220>
<221> SITE
<222> 41
<223> X = Y or F

<220>
<221> SITE
<222> 42
<223> X = L or Q

<220>
<221> SITE
<222> 44
<223> X = K or R

<220>
<221> SITE
<222> 47
<223> X = Q or K

<220>
<221> SITE
<222> 48
<223> X = S or A or V

<220>
<221> SITE
<222> 50
<223> X = K or Q or R
```

<220>
<221> SITE
<222> 51
<223> X = L or R or V

<220>
<221> SITE
<222> 55
<223> X = K or G or L

<220>
<221> SITE
<222> 56
<223> X = V or A or G

<220>
<221> SITE
<222> 58
<223> X = N or T

<220>
<221> SITE
<222> 60
<223> X = L or D or A

<220>
<221> SITE
<222> 61
<223> X = S or T

<220>
<221> SITE
<222> 63
<223> X = V or I

<220>
<221> SITE
<222> 65
<223> X = D or A or S

<220>
<221> SITE
<222> 75
<223> X = Y or D

<220>
<221> SITE
<222> 79
<223> X = K or T

```
<220>
<221> SITE
<222> 81
<223> X = S or N

<220>
<221> SITE
<222> 82
<223> X = R or S

<220>
<221> SITE
<222> 83
<223> X = V or L

<220>
<221> SITE
<222> 84
<223> X = E or Q

<220>
<221> SITE
<222> 85
<223> X = A or P

<220>
<221> SITE
<222> 88
<223> X = L or V or F

<220>
<221> SITE
<222> 89
<223> X = G or A

<220>
<221> SITE
<222> 90
<223> X = V or T

<220>
<221> SITE
<222> 92
<223> X = Y or F

<220>
<221> SITE
<222> 94
<223> X = S or M or Q
```

```
<220>
<221> SITE
<222> 96
<223> X = S or A

<220>
<221> SITE
<222> 97
<223> X = T or Y

<220>
<221> SITE
<222> 98
<223> X = H or Q or N

<220>
<221> SITE
<222> 99
<223> X = I or T

<220>
<221> SITE
<222> 100
<223> X = P or S

<220>
<221> SITE
<222> 105
<223> X = G or Q

<400> 1
Xaa Xaa Val Met Thr Gln Ser Pro Xaa Xaa Leu Xaa Xaa Xaa Xaa Gly
1               5                   10                  15
Xaa Xaa Xaa Xaa Xaa Xaa Cys Arg Xaa Ser Gln Ser Xaa Xaa Lys Xaa
            20                  25                  30
Xaa Xaa Xaa Xaa Xaa Leu Xaa Trp Xaa Xaa Gln Xaa Pro Gly Xaa Xaa
            35                  40                  45
Pro Xaa Xaa Leu Ile Tyr Xaa Xaa Ser Xaa Arg Xaa Xaa Gly Xaa Pro
    50                  55                  60
Xaa Arg Phe Ser Gly Ser Gly Ser Gly Thr Xaa Phe Thr Leu Xaa Ile
65                  70                  75                  80
Xaa Xaa Xaa Xaa Xaa Glu Asp Xaa Xaa Xaa Tyr Xaa Cys Xaa Gln Xaa
                85                  90                  95
Xaa Xaa Xaa Xaa Tyr Thr Phe Gly Xaa Gly Thr Lys Val Glu Ile Lys
        100                 105                 110

<210> 2
<211> 119
<212> PRT
<213> Artificial Sequence
```

<220>
<223> OGD201 Consensus sequence for third humanized VH sequence

<220>
<221> SITE
<222> 1
<223> X = E or Q

<220>
<221> SITE
<222> 5
<223> X = V or L

<220>
<221> SITE
<222> 13
<223> X = Q or K

<220>
<221> SITE
<222> 16
<223> X = G or R

<220>
<221> SITE
<222> 23
<223> X = A or T

<220>
<221> SITE
<222> 24
<223> X = T or A

<220>
<221> SITE
<222> 26
<223> X = E or G

<220>
<221> SITE
<222> 30
<223> X = T or S or G

<220>
<221> SITE
<222> 32
<223> X = Y or H

<220>
<221> SITE
<222> 35
<223> X = T or S or H or N

```
<220>
<221> SITE
<222> 37
<223> X = V or I

<220>
<221> SITE
<222> 48
<223> X = L or V

<220>
<221> SITE
<222> 49
<223> X = G or S

<220>
<221> SITE
<222> 50
<223> X = F or Y

<220>
<221> SITE
<222> 51
<223> X = I or T

<220>
<221> SITE
<222> 54
<223> X = R or K or S

<220>
<221> SITE
<222> 55
<223> X = A or S

<220>
<221> SITE
<222> 57
<223> X = G or A or S

<220>
<221> SITE
<222> 58
<223> X = Y or G

<220>
<221> SITE
<222> 59
<223> X = T or I
```

```
<220>
<221> SITE
<222> 60
<223> X = T or I

<220>
<221> SITE
<222> 61
<223> X = E or Y

<220>
<221> SITE
<222> 63
<223> X = N or A

<220>
<221> SITE
<222> 64
<223> X = P or A or D

<220>
<221> SITE
<222> 76
<223> X = N or G

<220>
<221> SITE
<222> 77
<223> X = S or A

<220>
<221> SITE
<222> 79
<223> X = S or N

<220>
<221> SITE
<222> 80
<223> X = I or S or T

<220>
<221> SITE
<222> 81
<223> X = L or T or A

<220>
<221> SITE
<222> 89
<223> X = R or K or Q
```

```
<220>
<221> SITE
<222> 90
<223> X = T or A

<220>
<221> SITE
<222> 95
<223> X = V or I or L

<220>
<221> SITE
<222> 99
<223> X = T or A

<220>
<221> SITE
<222> 104
<223> X = W or Y

<220>
<221> SITE
<222> 105
<223> X = A or Y

<220>
<221> SITE
<222> 114
<223> X = T or L

<220>
<221> SITE
<222> 115
<223> X = L or V

<400> 2
Xaa Val Gln Leu Xaa Glu Ser Gly Gly Gly Leu Val Xaa Pro Gly Xaa
1               5                   10                  15
Ser Leu Arg Leu Ser Cys Xaa Xaa Ser Xaa Phe Thr Phe Xaa Asp Xaa
            20                  25                  30
Tyr Met Xaa Trp Xaa Arg Gln Ala Pro Gly Lys Gly Leu Glu Trp Xaa
        35                  40                  45
Xaa Xaa Xaa Arg Asn Xaa Xaa Asn Xaa Xaa Xaa Xaa Xaa Tyr Xaa Xaa
    50                  55                  60
Ser Val Lys Gly Arg Phe Thr Ile Ser Arg Asp Xaa Xaa Lys Xaa Xaa
65                  70                  75                  80
Xaa Tyr Leu Gln Met Asn Ser Leu Xaa Xaa Glu Asp Thr Ala Xaa Tyr
            85                  90                  95
Tyr Cys Xaa Arg Val Ser Asn Xaa Xaa Phe Asp Tyr Trp Gly Gln Gly
        100                 105                 110
Thr Xaa Xaa Thr Val Ser Ser
        115
```

<210> 3
<211> 112
<212> PRT
<213> Artificial Sequence

<220>
<223> OGD201 Consensus sequence for second humanized VL sequence

<220>
<221> SITE
<222> 1
<223> X = D or E

<220>
<221> SITE
<222> 9
<223> X = L or A

<220>
<221> SITE
<222> 10
<223> X = S or T

<220>
<221> SITE
<222> 1
<223> X = D or E

<220>
<221> SITE
<222> 9
<223> X = L or A

<220>
<221> SITE
<222> 10
<223> X = S or T

<220>
<221> SITE
<222> 13
<223> X = V or L or A

<220>
<221> SITE
<222> 14
<223> X = S or T

<220>
<221> SITE
<222> 15
<223> X = L or P or V

```
<220>
<221> SITE
<222> 17
<223> X = D or Q or E

<220>
<221> SITE
<222> 18
<223> X = Q or P or R

<220>
<221> SITE
<222> 19
<223> X = A or V

<220>
<221> SITE
<222> 20
<223> X = S or T

<220>
<221> SITE
<222> 21
<223> X = I or L

<220>
<221> SITE
<222> 22
<223> X = S or T

<220>
<221> SITE
<222> 30
<223> X = L or V

<220>
<221> SITE
<222> 33
<223> X = N or Q

<220>
<221> SITE
<222> 34
<223> X = G or A

<220>
<221> SITE
<222> 37
<223> X = F or Y
```

```
<220>
<221> SITE
<222> 41
<223> X = Y or F

<220>
<221> SITE
<222> 42
<223> X = L or Q

<220>
<221> SITE
<222> 44
<223> X = K or R

<220>
<221> SITE
<222> 47
<223> X = Q or K

<220>
<221> SITE
<222> 48
<223> X = S or A

<220>
<221> SITE
<222> 50
<223> X = K or Q or R

<220>
<221> SITE
<222> 51
<223> X = L or R or V

<220>
<221> SITE
<222> 61
<223> X = S or T

<220>
<221> SITE
<222> 63
<223> X = V or I

<220>
<221> SITE
<222> 65
<223> X = D or A or S
```

```
<220>
<221> SITE
<222> 75
<223> X = Y or D

<220>
<221> SITE
<222> 79
<223> X = K or T

<220>
<221> SITE
<222> 81
<223> X = S or N

<220>
<221> SITE
<222> 82
<223> X = R or S

<220>
<221> SITE
<222> 83
<223> X = V or L

<220>
<221> SITE
<222> 84
<223> X = E or Q

<220>
<221> SITE
<222> 85
<223> X = A or P

<220>
<221> SITE
<222> 88
<223> X = L or V or F

<220>
<221> SITE
<222> 89
<223> X = G or A

<220>
<221> SITE
<222> 90
<223> X = V or T
```

<220>
<221> SITE
<222> 92
<223> X = Y or F

<220>
<221> SITE
<222> 105
<223> X = G or Q

<400> 3
Xaa Val Val Met Thr Gln Ser Pro Xaa Xaa Leu Xaa Xaa Xaa Xaa Gly
1               5                   10                  15
Xaa Xaa Xaa Xaa Xaa Xaa Cys Arg Ser Ser Gln Ser Leu Xaa Lys Asn
            20                  25                  30
Xaa Xaa Asn Thr Xaa Leu His Trp Xaa Xaa Gln Xaa Pro Gly Xaa Xaa
        35                  40                  45
Pro Xaa Xaa Leu Ile Tyr Lys Val Ser Asn Arg Leu Xaa Gly Xaa Pro
    50                  55                  60
Xaa Arg Phe Ser Gly Ser Gly Ser Gly Thr Xaa Phe Thr Leu Xaa Ile
65              70                  75                  80
Xaa Xaa Xaa Xaa Xaa Glu Asp Xaa Xaa Xaa Tyr Xaa Cys Ser Gln Ser
                85                  90                  95
Thr His Ile Pro Tyr Thr Phe Gly Xaa Gly Thr Lys Val Glu Ile Lys
            100                 105                 110

<210> 4
<211> 112
<212> PRT
<213> Artificial Sequence

<220>
<223> OGD201 VL15

<400> 4
Asp Val Val Met Thr Gln Ser Pro Leu Ser Leu Pro Val Thr Leu Gly
1               5                   10                  15
Gln Pro Ala Ser Ile Ser Cys Arg Ser Ser Gln Ser Leu Val Lys Asn
            20                  25                  30
Gln Ala Asn Thr Tyr Leu His Trp Phe Gln Gln Arg Pro Gly Gln Ser
        35                  40                  45
Pro Arg Leu Leu Ile Tyr Lys Val Ser Asn Arg Leu Ser Gly Val Pro
    50                  55                  60
Asp Arg Phe Ser Gly Ser Gly Ser Gly Thr Asp Phe Thr Leu Lys Ile
65              70                  75                  80
Ser Arg Val Glu Ala Glu Asp Val Gly Val Tyr Tyr Cys Ser Gln Ser
                85                  90                  95
Thr His Ile Pro Tyr Thr Phe Gly Gly Gly Thr Lys Val Glu Ile Lys
            100                 105                 110

<210> 5
<211> 112
<212> PRT
<213> Artificial Sequence

<220>
<223> OGD201 VL16

<400> 5
Glu Val Val Met Thr Gln Ser Pro Ala Thr Leu Ser Leu Thr Pro Gly
1               5                   10                  15
Gln Pro Ala Thr Leu Ser Cys Arg Ser Ser Gln Ser Leu Val Lys Asn
            20                  25                  30
Gln Ala Asn Thr Tyr Leu His Trp Phe Gln Gln Arg Pro Gly Gln Ala
        35                  40                  45
Pro Arg Leu Leu Ile Tyr Lys Val Ser Asn Arg Leu Thr Gly Ile Pro
    50                  55                  60
Ala Arg Phe Ser Gly Ser Gly Ser Gly Thr Asp Phe Thr Leu Thr Ile
65                  70                  75                  80
Ser Ser Leu Gln Pro Glu Asp Val Ala Val Tyr Tyr Cys Ser Gln Ser
            85                  90                  95
Thr His Ile Pro Tyr Thr Phe Gly Gly Gly Thr Lys Val Glu Ile Lys
            100                 105                 110

<210> 6
<211> 112
<212> PRT
<213> Artificial Sequence

<220>
<223> OGD201 VL17

<400> 6
Glu Val Val Met Thr Gln Ser Pro Ala Thr Leu Ser Leu Ser Pro Gly
1               5                   10                  15
Glu Arg Ala Thr Leu Ser Cys Arg Ser Ser Gln Ser Leu Val Lys Asn
            20                  25                  30
Gln Ala Asn Thr Tyr Leu His Trp Tyr Gln Gln Lys Pro Gly Gln Ala
        35                  40                  45
Pro Arg Leu Leu Ile Tyr Lys Val Ser Asn Arg Leu Thr Gly Ile Pro
    50                  55                  60
Ala Arg Phe Ser Gly Ser Gly Ser Gly Thr Asp Phe Thr Leu Thr Ile
65                  70                  75                  80
Ser Ser Leu Gln Ala Glu Asp Phe Ala Val Tyr Tyr Cys Ser Gln Ser
            85                  90                  95
Thr His Ile Pro Tyr Thr Phe Gly Gly Gly Thr Lys Val Glu Ile Lys
            100                 105                 110

<210> 7
<211> 112
<212> PRT
<213> Artificial Sequence

<220>
<223> OGD201 VL18

<400> 7
Glu Val Val Met Thr Gln Ser Pro Ala Thr Leu Ser Leu Thr Pro Gly
1               5                   10                  15
Glu Arg Ala Thr Leu Ser Cys Arg Ser Ser Gln Ser Leu Val Lys Asn
            20                  25                  30
Gln Ala Asn Thr Tyr Leu His Trp Phe Gln Gln Arg Pro Gly Gln Ala
        35                  40                  45
Pro Arg Leu Leu Ile Tyr Lys Val Ser Asn Arg Leu Thr Gly Ile Pro
    50                  55                  60
Ala Arg Phe Ser Gly Ser Gly Ser Gly Thr Asp Phe Thr Leu Thr Ile
65                  70                  75                  80
Ser Ser Leu Gln Pro Glu Asp Phe Ala Val Tyr Tyr Cys Ser Gln Ser
            85                  90                  95
Thr His Ile Pro Tyr Thr Phe Gly Gly Gly Thr Lys Val Glu Ile Lys
            100                 105                 110

<210> 8
<211> 119
<212> PRT
<213> Artificial Sequence

<220>
<223> OGD201 Consensus sequence for second humanized VH sequence

<220>
<221> SITE
<222> 1
<223> X = E or Q

<220>
<221> SITE
<222> 5
<223> X = V or L

<220>
<221> SITE
<222> 13
<223> X = Q or K

```
<220>
<221> SITE
<222> 16
<223> X = G or R

<220>
<221> SITE
<222> 23
<223> X = A or T

<220>
<221> SITE
<222> 24
<223> X = T or A

<220>
<221> SITE
<222> 48
<223> X = L or V

<220>
<221> SITE
<222> 49
<223> X = G or S

<220>
<221> SITE
<222> 57
<223> X = G or A

<220>
<221> SITE
<222> 63
<223> X = N or A

<220>
<221> SITE
<222> 64
<223> X = P or A

<220>
<221> SITE
<222> 77
<223> X = S or A

<220>
<221> SITE
<222> 79
<223> X = S or N
```

```
<220>
<221> SITE
<222> 80
<223> X = I or S or T

<220>
<221> SITE
<222> 81
<223> X = L or T

<220>
<221> SITE
<222> 89
<223> X = R or K or Q

<220>
<221> SITE
<222> 90
<223> X = T or A

<220>
<221> SITE
<222> 95
<223> X = V or I

<220>
<221> SITE
<222> 114
<223> X = T or L

<220>
<221> SITE
<222> 115
<223> X = L or V
```

<400> 8
Xaa Val Gln Leu Xaa Glu Ser Gly Gly Gly Leu Val Xaa Pro Gly Xaa
1               5                   10                  15
Ser Leu Arg Leu Ser Cys Xaa Xaa Ser Glu Phe Thr Phe Thr Asp Tyr
            20                  25                  30
Tyr Met Thr Trp Val Arg Gln Ala Pro Gly Lys Gly Leu Glu Trp Xaa
        35                  40                  45
Xaa Phe Ile Arg Asn Arg Ala Asn Xaa Tyr Thr Thr Glu Tyr Xaa Xaa
    50                  55                  60
Ser Val Lys Gly Arg Phe Thr Ile Ser Arg Asp Asn Xaa Lys Xaa Xaa
65                  70                  75                  80
Xaa Tyr Leu Gln Met Asn Ser Leu Xaa Xaa Glu Asp Thr Ala Xaa Tyr
                85                  90                  95
Tyr Cys Ala Arg Val Ser Asn Trp Ala Phe Asp Tyr Trp Gly Gln Gly
            100                 105                 110
Thr Xaa Xaa Thr Val Ser Ser
        115

<210> 9
<211> 119
<212> PRT
<213> Artificial Sequence

<220>
<223> OGD201 VH19

<400> 9
Glu Val Gln Leu Val Glu Ser Gly Gly Gly Leu Val Gln Pro Gly Gly
1               5                   10                  15
Ser Leu Arg Leu Ser Cys Ala Ala Ser Glu Phe Thr Phe Thr Asp Tyr
            20                  25                  30
Tyr Met Thr Trp Val Arg Gln Ala Pro Gly Lys Gly Leu Glu Trp Val
        35                  40                  45
Gly Phe Ile Arg Asn Arg Ala Asn Ala Tyr Thr Thr Glu Tyr Ala Ala
    50                  55                  60
Ser Val Lys Gly Arg Phe Thr Ile Ser Arg Asp Asn Ser Lys Asn Ser
65                  70                  75                  80
Leu Tyr Leu Gln Met Asn Ser Leu Lys Thr Glu Asp Thr Ala Val Tyr
                85                  90                  95
Tyr Cys Ala Arg Val Ser Asn Trp Ala Phe Asp Tyr Trp Gly Gln Gly
            100                 105                 110
Thr Leu Val Thr Val Ser Ser
        115

<210> 10
<211> 119
<212> PRT
<213> Artificial Sequence

<220>
<223> OGD201 VH20

<400> 10
Glu Val Gln Leu Val Glu Ser Gly Gly Gly Leu Val Gln Pro Gly Gly
1               5                   10                  15
Ser Leu Arg Leu Ser Cys Ala Ala Ser Glu Phe Thr Phe Thr Asp Tyr
            20                  25                  30
Tyr Met Thr Trp Val Arg Gln Ala Pro Gly Lys Gly Leu Glu Trp Leu
        35                  40                  45
Gly Phe Ile Arg Asn Arg Ala Asn Ala Tyr Thr Thr Glu Tyr Ala Ala
    50                  55                  60
Ser Val Lys Gly Arg Phe Thr Ile Ser Arg Asp Asn Ser Lys Asn Ser
65                  70                  75                  80
Leu Tyr Leu Gln Met Asn Ser Leu Lys Thr Glu Asp Thr Ala Val Tyr
                85                  90                  95
Tyr Cys Ala Arg Val Ser Asn Trp Ala Phe Asp Tyr Trp Gly Gln Gly
            100                 105                 110
Thr Leu Val Thr Val Ser Ser
        115

<210> 11
<211> 119
<212> PRT
<213> Artificial Sequence

<220>
<223> OGD201 VH21

<400> 11
Glu Val Gln Leu Val Glu Ser Gly Gly Gly Leu Val Gln Pro Gly Arg
1               5                   10                  15
Ser Leu Arg Leu Ser Cys Thr Ala Ser Glu Phe Thr Phe Thr Asp Tyr
            20                  25                  30
Tyr Met Thr Trp Val Arg Gln Ala Pro Gly Lys Gly Leu Glu Trp Leu
        35                  40                  45
Gly Phe Ile Arg Asn Arg Ala Asn Ala Tyr Thr Thr Glu Tyr Ala Ala
    50                  55                  60
Ser Val Lys Gly Arg Phe Thr Ile Ser Arg Asp Asn Ser Lys Ser Ile
65                  70                  75                  80
Leu Tyr Leu Gln Met Asn Ser Leu Lys Thr Glu Asp Thr Ala Val Tyr
                85                  90                  95
Tyr Cys Ala Arg Val Ser Asn Trp Ala Phe Asp Tyr Trp Gly Gln Gly
            100                 105                 110
Thr Leu Val Thr Val Ser Ser
        115

<210> 12
<211> 112
<212> PRT
<213> Artificial Sequence

<220>
<223> OGD201 Consensus sequence for first humanized VL sequence

<220>
<221> SITE
<222> 1
<223> X = D or E

<220>
<221> SITE
<222> 3
<223> X = V or Q

<220>
<221> SITE
<222> 9
<223> X = L or A

<220>
<221> SITE
<222> 10
<223> X = S or T

```
<220>
<221> SITE
<222> 12
<223> X = P or S

<220>
<221> SITE
<222> 13
<223> X = V or L or A

<220>
<221> SITE
<222> 14
<223> X = S or T

<220>
<221> SITE
<222> 15
<223> X = L or P or V

<220>
<221> SITE
<222> 17
<223> X = D or Q or E

<220>
<221> SITE
<222> 18
<223> X = Q or P or R

<220>
<221> SITE
<222> 19
<223> X = A or V

<220>
<221> SITE
<222> 20
<223> X = S or T

<220>
<221> SITE
<222> 21
<223> X = I or L

<220>
<221> SITE
<222> 22
<223> X = S or T
```

```
<220>
<221> SITE
<222> 42
<223> X = L or Q

<220>
<221> SITE
<222> 44
<223> X = K or R

<220>
<221> SITE
<222> 47
<223> X = Q or K

<220>
<221> SITE
<222> 48
<223> X = S or A

<220>
<221> SITE
<222> 50
<223> X = K or Q or R

<220>
<221> SITE
<222> 61
<223> X = S or T

<220>
<221> SITE
<222> 63
<223> X = V or I

<220>
<221> SITE
<222> 65
<223> X = D or A or S

<220>
<221> SITE
<222> 75
<223> X = Y or D

<220>
<221> SITE
<222> 79
<223> X = K or T
```

<220>
<221> SITE
<222> 82
<223> X = R or S

<220>
<221> SITE
<222> 83
<223> X = V or L

<220>
<221> SITE
<222> 84
<223> X = E or Q

<220>
<221> SITE
<222> 85
<223> X = A or P

<220>
<221> SITE
<222> 88
<223> X = L or V or F

<220>
<221> SITE
<222> 89
<223> X = G or A

<220>
<221> SITE
<222> 90
<223> X = V or T

<220>
<221> SITE
<222> 92
<223> X = Y or F

<220>
<221> SITE
<222> 105
<223> X = G or Q

<400> 12
Xaa Val Xaa Met Thr Gln Ser Pro Xaa Xaa Leu Xaa Xaa Xaa Xaa Gly
1               5                   10                  15
Xaa Xaa Xaa Xaa Xaa Xaa Cys Arg Ser Ser Gln Ser Leu Leu Lys Asn
            20                  25                  30
Asn Gly Asn Thr Phe Leu His Trp Tyr Xaa Gln Xaa Pro Gly Xaa Xaa
            35                  40                  45
Pro Xaa Leu Leu Ile Tyr Lys Val Ser Asn Arg Leu Xaa Gly Xaa Pro
        50                  55                  60
Xaa Arg Phe Ser Gly Ser Gly Ser Gly Thr Xaa Phe Thr Leu Xaa Ile
65                  70                  75                  80
Ser Xaa Xaa Xaa Xaa Glu Asp Xaa Xaa Xaa Tyr Xaa Cys Ser Gln Ser
            85                  90                  95
Thr His Ile Pro Tyr Thr Phe Gly Xaa Gly Thr Lys Val Glu Ile Lys
            100                 105                 110

<210> 13
<211> 119
<212> PRT
<213> Artificial Sequence

<220>
<223> OGD201 Consensus sequence for first humanized VH sequence

<220>
<221> SITE
<222> 1
<223> X = E or Q

<220>
<221> SITE
<222> 13
<223> X = Q or K

<220>
<221> SITE
<222> 16
<223> X = G or R

<220>
<221> SITE
<222> 23
<223> X = A or T

<220>
<221> SITE
<222> 77
<223> X = S or A

<220>
<221> SITE
<222> 79
<223> X = S or N

<220>
<221> SITE
<222> 80
<223> X = I or S

<220>
<221> SITE
<222> 89
<223> X = R or K

<220>
<221> SITE
<222> 90
<223> X = T or A

<400> 13
Xaa Val Gln Leu Val Glu Ser Gly Gly Gly Leu Val Xaa Pro Gly Xaa
1               5                   10                  15
Ser Leu Arg Leu Ser Cys Xaa Thr Ser Glu Phe Thr Phe Thr Asp Tyr
            20                  25                  30
Tyr Met Thr Trp Val Arg Gln Ala Pro Gly Lys Gly Leu Glu Trp Leu
        35                  40                  45
Gly Phe Ile Arg Asn Arg Ala Asn Gly Tyr Thr Thr Glu Tyr Asn Pro
    50                  55                  60
Ser Val Lys Gly Arg Phe Thr Ile Ser Arg Asp Asn Xaa Lys Xaa Xaa
65                  70                  75                  80
Leu Tyr Leu Gln Met Asn Ser Leu Xaa Xaa Glu Asp Thr Ala Val Tyr
            85                  90                  95
Tyr Cys Ala Arg Val Ser Asn Trp Ala Phe Asp Tyr Trp Gly Gln Gly
            100                 105                 110
Thr Thr Leu Thr Val Ser Ser
        115

<210> 14
<211> 112
<212> PRT
<213> Mus musculus

<400> 14
Asp Val Val Met Thr Gln Thr Pro Leu Ser Leu Pro Val Ser Leu Gly
1               5                   10                  15
Asp Gln Ala Ser Ile Ser Cys Arg Ser Ser Gln Ser Leu Leu Lys Asn
                20                  25                  30
Asn Gly Asn Thr Phe Leu His Trp Tyr Leu Gln Lys Ser Gly Gln Ser
            35                  40                  45
Pro Lys Leu Leu Ile Tyr Lys Val Ser Asn Arg Leu Ser Gly Val Pro
        50                  55                  60
Asp Arg Phe Ser Gly Ser Gly Ser Gly Thr Tyr Phe Thr Leu Lys Ile
65                  70                  75                  80
Ser Arg Val Glu Ala Glu Asp Leu Gly Val Tyr Phe Cys Ser Gln Ser
                85                  90                  95
Thr His Ile Pro Tyr Thr Phe Gly Gly Gly Thr Lys Leu Glu Ile Lys
            100                 105                 110

<210> 15
<211> 119
<212> PRT
<213> Mus musculus

<400> 15
Glu Val Lys Leu Val Glu Ser Gly Gly Gly Leu Val Leu Pro Gly Asp
1               5                   10                  15
Ser Leu Arg Leu Ser Cys Ala Thr Ser Glu Phe Thr Phe Thr Asp Tyr
                20                  25                  30
Tyr Met Thr Trp Val Arg Gln Pro Pro Arg Lys Ala Leu Glu Trp Leu
            35                  40                  45
Gly Phe Ile Arg Asn Arg Ala Asn Gly Tyr Thr Thr Glu Tyr Asn Pro
        50                  55                  60
Ser Val Lys Gly Arg Phe Thr Ile Ser Arg Asp Asn Ser Gln Ser Ile
65                  70                  75                  80
Leu Tyr Leu Gln Met Asn Thr Leu Arg Thr Glu Asp Ser Ala Thr Tyr
                85                  90                  95
Tyr Cys Ala Arg Val Ser Asn Trp Ala Phe Asp Tyr Trp Gly Gln Gly
            100                 105                 110
Thr Thr Leu Thr Val Ser Ser
        115

<210> 16
<211> 10
<212> PRT
<213> Artificial Sequence

<220>
<223> CDR1_VH

<400> 16
Glu Phe Thr Phe Thr Asp Tyr Tyr Met Thr
1               5                   10

<210> 17
<211> 19
<212> PRT
<213> Artificial Sequence

<220>
<223> CDR2_VH

<400> 17
Phe Ile Arg Asn Arg Ala Asn Gly Tyr Thr Thr Glu Tyr Asn Pro Ser
1               5                   10                  15
Val Lys Gly

<210> 18
<211> 10
<212> PRT
<213> Artificial Sequence

<220>
<223> CDR3_VH

<400> 18
Ala Arg Val Ser Asn Trp Ala Phe Asp Tyr
1               5                   10

<210> 19
<211> 16
<212> PRT
<213> Artificial Sequence

<220>
<223> CDR1_VL

<400> 19
Arg Ser Ser Gln Ser Leu Leu Lys Asn Asn Gly Asn Thr Phe Leu His
1               5                   10                  15

<210> 20
<211> 7
<212> PRT
<213> Artificial Sequence

<220>
<223> CDR2_VL

<400> 20
Tyr Lys Val Ser Asn Arg Leu
1               5

<210> 21
<211> 9
<212> PRT
<213> Artificial Sequence

<220>
<223> CDR3_VL

<400> 21
Ser Gln Ser Thr His Ile Pro Tyr Thr
1               5

<210> 22
<211> 5
<212> PRT
<213> Artificial Sequence

<220>
<223> scFv linker

<400> 22
Gly Ser Gly Gly Ser
1               5

<210> 23
<211> 4
<212> PRT
<213> Artificial Sequence

<220>
<223> scFv linker

<400> 23
Gly Gly Gly Ser
1

<210> 24
<211> 5
<212> PRT
<213> Artificial Sequence

<220>
<223> scFv linker

<400> 24
Gly Gly Gly Gly Ser
1               5

<210> 25
<211> 15
<212> PRT
<213> Artificial Sequence

<220>
<223> ((G4S)3 linker

<400> 25
Gly Gly Gly Gly Ser Gly Gly Gly Gly Ser Gly Gly Gly Gly Ser
1               5                   10                  15

<210> 26
<211> 18
<212> PRT
<213> Artificial Sequence

<220>
<223> CD19 linker

<400> 26
Gly Ser Thr Ser Gly Ser Gly Lys Pro Gly Ser Gly Glu Gly Ser Thr
1               5                   10                  15
Lys Gly

<210> 27
<211> 18
<212> PRT
<213> Artificial Sequence

<220>
<223> 18mer

<400> 27
Gly Gly Ser Ser Arg Ser Ser Ser Ser Gly Gly Gly Gly Ser Gly Gly
1               5                   10                  15
Gly Gly

<210> 28
<211> 20
<212> PRT
<213> Artificial Sequence

<220>
<223> (G4S)4 linker

<400> 28
Gly Gly Gly Gly Ser Gly Gly Gly Gly Ser Gly Gly Gly Gly Ser Gly
1               5                   10                  15
Gly Gly Gly Ser
            20

<210> 29
<211> 18
<212> PRT
<213> Artificial Sequence

<220>
<223> linker

<400> 29
Lys Glu Ser Gly Ser Val Ser Ser Glu Gln Leu Ala Gln Phe Arg Ser
1               5                   10                  15
Leu Asp

<210> 30
<211> 14
<212> PRT
<213> Artificial Sequence

<220>
<223> linker

<400> 30
Glu Gly Lys Ser Ser Gly Ser Gly Ser Glu Ser Lys Ser Thr
1               5                   10

<210> 31
<211> 12
<212> PRT
<213> Artificial Sequence

<220>
<223> linker

<400> 31
Gly Ser Ala Gly Ser Ala Ala Gly Ser Gly Glu Phe
1               5                   10

<210> 32
<211> 8
<212> PRT
<213> Artificial Sequence

<220>
<223> linker

<400> 32
Gly Gly Gly Gly Gly Gly Gly Gly
1               5

<210> 33
<211> 6
<212> PRT
<213> Artificial Sequence

<220>
<223> linker

<400> 33
Gly Gly Gly Gly Gly Gly
1               5

<210> 34
<211> 112
<212> PRT
<213> Artificial Sequence

<220>
<223> OGD201 VL1

<400> 34
Asp Val Val Met Thr Gln Ser Pro Leu Ser Leu Pro Val Thr Leu Gly
1               5                   10                  15
Gln Pro Ala Ser Ile Ser Cys Arg Ser Ser Gln Ser Leu Leu Lys Asn
            20                  25                  30
Asn Gly Asn Thr Phe Leu His Trp Tyr Gln Gln Arg Pro Gly Gln Ser
        35                  40                  45
Pro Arg Leu Leu Ile Tyr Lys Val Ser Asn Arg Leu Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Phe Cys Ser Gln Ser
                85                  90                  95
Thr His Ile Pro Tyr Thr Phe Gly Gly Gly Thr Lys Val Glu Ile Lys
            100                 105                 110

<210> 35
<211> 112
<212> PRT
<213> Artificial Sequence

<220>
<223> OGD201 VL2

<400> 35
Glu Val Val Met Thr Gln Ser Pro Ala Thr Leu Ser Leu Ser Pro Gly
1               5                   10                  15
Glu Arg Ala Thr Leu Ser Cys Arg Ser Ser Gln Ser Leu Leu Lys Asn
            20                  25                  30
Asn Gly Asn Thr Phe Leu His Trp Tyr Gln Gln Lys Pro Gly Gln Ala
        35                  40                  45
Pro Arg Leu Leu Ile Tyr Lys Val Ser Asn Arg Leu Thr Gly Ile Pro
    50                  55                  60
Ala Arg Phe Ser Gly Ser Gly Ser Gly Thr Asp Phe Thr Leu Thr Ile
65                  70                  75                  80
Ser Ser Leu Gln Pro Glu Asp Phe Ala Val Tyr Phe Cys Ser Gln Ser
                85                  90                  95
Thr His Ile Pro Tyr Thr Phe Gly Gly Gly Thr Lys Val Glu Ile Lys
            100                 105                 110

<210> 36
<211> 112
<212> PRT
<213> Artificial Sequence

<220>
<223> OGD201 VL3

<400> 36
Asp Val Val Met Thr Gln Ser Pro Leu Ser Leu Pro Val Thr Pro Gly
1               5                   10                  15
Glu Pro Ala Ser Ile Ser Cys Arg Ser Ser Gln Ser Leu Leu Lys Asn
            20                  25                  30
Asn Gly Asn Thr Phe Leu His Trp Tyr Leu Gln Lys Pro Gly Gln Ser
        35                  40                  45
Pro Gln Leu Leu Ile Tyr Lys Val Ser Asn Arg Leu Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Phe Cys Ser Gln Ser
                85                  90                  95
Thr His Ile Pro Tyr Thr Phe Gly Gln Gly Thr Lys Val Glu Ile Lys
            100                 105                 110

<210> 37
<211> 112
<212> PRT
<213> Artificial Sequence

<220>
<223> OGD201 VL4

<400> 37
Asp Val Gln Met Thr Gln Ser Pro Ser Ser Leu Ser Ala Ser Val Gly
1               5                   10                  15
Asp Arg Val Thr Ile Thr Cys Arg Ser Ser Gln Ser Leu Leu Lys Asn
            20                  25              30
Asn Gly Asn Thr Phe Leu His Trp Tyr Gln Gln Lys Pro Gly Lys Ala
        35              40              45
Pro Lys Leu Leu Ile Tyr Lys Val Ser Asn Arg Leu Ser Gly Val Pro
    50              55              60
Ser Arg Phe Ser Gly Ser Gly Ser Gly Thr Asp Phe Thr Leu Thr Ile
65              70              75              80
Ser Ser Leu Gln Pro Glu Asp Val Ala Thr Tyr Tyr Cys Ser Gln Ser
            85              90              95
Thr His Ile Pro Tyr Thr Phe Gly Gln Gly Thr Lys Val Glu Ile Lys
        100             105             110

<210> 38
<211> 112
<212> PRT
<213> Artificial Sequence

<220>
<223> OGD201 VL28BH

<400> 38
Asp Val Val Met Thr Gln Ser Pro Leu Ser Leu Pro Val Thr Pro Gly
1               5                   10                  15
Glu Pro Ala Ser Ile Ser Cys Arg Ser Ser Gln Ser Leu Leu Lys Asn
            20                  25              30
Asn Ala Asn Thr Phe Leu His Trp Tyr Leu Gln Lys Pro Gly Gln Ser
        35              40              45
Pro Gln Leu Leu Ile Tyr Lys Val Ser Asn Arg Ala Ser Gly Val Pro
    50              55              60
Asp Arg Phe Ser Gly Ser Gly Ser Gly Thr Asp Phe Thr Leu Lys Ile
65              70              75              80
Ser Arg Val Glu Ala Glu Asp Val Gly Val Tyr Tyr Cys Ser Gln Ser
            85              90              95
Thr His Ile Pro Tyr Thr Phe Gly Gln Gly Thr Lys Val Glu Ile Lys
        100             105             110

<210> 39
<211> 112
<212> PRT
<213> Artificial Sequence

<220>
<223> OGD201 VL30BH

<400> 39
Asp Val Val Met Thr Gln Ser Pro Leu Ser Leu Pro Val Thr Leu Gly
1               5                   10                  15
Gln Pro Ala Ser Ile Ser Cys Arg Ser Ser Gln Ser Leu Val Lys Asn
            20                  25                  30
Gln Gly Asn Thr Phe Leu His Trp Phe Gln Gln Arg Pro Gly Gln Ser
        35                  40                  45
Pro Arg Leu Leu Ile Tyr Lys Val Ser Asn Arg Leu Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Ser Gln Ser
                85                  90                  95
Thr His Ile Pro Tyr Thr Phe Gly Gly Gly Thr Lys Val Glu Ile Lys
            100                 105                 110

<210> 40
<211> 112
<212> PRT
<213> Artificial Sequence

<220>
<223> OGD201 VL28Bs01/A2

<400> 40
Asp Val Val Met Thr Gln Ser Pro Leu Ser Leu Pro Val Thr Pro Gly
1               5                   10                  15
Glu Pro Ala Ser Ile Ser Cys Arg Ser Ser Gln Ser Leu Leu Lys Ser
            20                  25                  30
Asn Ala Asn Thr Phe Leu His Trp Tyr Leu Gln Lys Pro Gly Gln Ser
        35                  40                  45
Pro Gln Leu Leu Ile Tyr Lys Val Ser Asn Arg Leu Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Met Gln Ser
                85                  90                  95
Thr His Ile Pro Tyr Thr Phe Gly Gln Gly Thr Lys Val Glu Ile Lys
            100                 105                 110

<210> 41
<211> 119
<212> PRT
<213> Artificial Sequence

<220>
<223> OGD201 VH1

<400> 41
Glu Val Gln Leu Val Glu Ser Gly Gly Gly Leu Val Gln Pro Gly Gly
1               5                   10                  15
Ser Leu Arg Leu Ser Cys Ala Thr Ser Glu Phe Thr Phe Thr Asp Tyr
                20                  25                  30
Tyr Met Thr Trp Val Arg Gln Ala Pro Gly Lys Gly Leu Glu Trp Leu
            35                  40              45
Gly Phe Ile Arg Asn Arg Ala Asn Gly Tyr Thr Thr Glu Tyr Asn Pro
        50              55              60
Ser Val Lys Gly Arg Phe Thr Ile Ser Arg Asp Asn Ser Lys Asn Ser
65              70              75              80
Leu Tyr Leu Gln Met Asn Ser Leu Lys Thr Glu Asp Thr Ala Val Tyr
            85                  90                  95
Tyr Cys Ala Arg Val Ser Asn Trp Ala Phe Asp Tyr Trp Gly Gln Gly
                100                 105                 110
Thr Leu Val Thr Val Ser Ser
        115

<210> 42
<211> 119
<212> PRT
<213> Artificial Sequence

<220>
<223> OGD201 VH2

<400> 42
Glu Val Gln Leu Val Glu Ser Gly Gly Gly Leu Val Gln Pro Gly Arg
1               5                   10                  15
Ser Leu Arg Leu Ser Cys Thr Thr Ser Glu Phe Thr Phe Thr Asp Tyr
                20                  25                  30
Tyr Met Thr Trp Val Arg Gln Ala Pro Gly Lys Gly Leu Glu Trp Leu
            35                  40              45
Gly Phe Ile Arg Asn Arg Ala Asn Gly Tyr Thr Thr Glu Tyr Asn Pro
        50              55              60
Ser Val Lys Gly Arg Phe Thr Ile Ser Arg Asp Asn Ser Lys Ser Ile
65              70              75              80
Leu Tyr Leu Gln Met Asn Ser Leu Lys Thr Glu Asp Thr Ala Val Tyr
            85                  90                  95
Tyr Cys Ala Arg Val Ser Asn Trp Ala Phe Asp Tyr Trp Gly Gln Gly
                100                 105                 110
Thr Leu Val Thr Val Ser Ser
        115

<210> 43
<211> 119
<212> PRT
<213> Artificial Sequence

<220>
<223> 201 VH3-11*01A

<400> 43
Gln Val Gln Leu Val Glu Ser Gly Gly Gly Leu Val Lys Pro Gly Gly
1               5                   10                  15
Ser Leu Arg Leu Ser Cys Ala Thr Ser Glu Phe Thr Phe Thr Asp Tyr
                20                  25                  30
Tyr Met Thr Trp Val Arg Gln Ala Pro Gly Lys Gly Leu Glu Trp Leu
            35                  40                  45
Gly Phe Ile Arg Asn Arg Ala Asn Gly Tyr Thr Thr Glu Tyr Asn Pro
        50                  55                  60
Ser Val Lys Gly Arg Phe Thr Ile Ser Arg Asp Asn Ala Lys Asn Ser
65                  70                  75                  80
Leu Tyr Leu Gln Met Asn Ser Leu Arg Ala Glu Asp Thr Ala Val Tyr
                85                  90                  95
Tyr Cys Ala Arg Val Ser Asn Trp Ala Phe Asp Tyr Trp Gly Gln Gly
            100                 105                 110
Thr Leu Val Thr Val Ser Ser
        115

<210> 44
<211> 119
<212> PRT
<213> Artificial Sequence

<220>
<223> OGD201 VH 72BCDR

<400> 44
Glu Val Gln Leu Val Glu Ser Gly Gly Gly Leu Val Gln Pro Gly Gly
1               5                   10                  15
Ser Leu Arg Leu Ser Cys Ala Ala Ser Glu Phe Thr Phe Thr Asp Tyr
                20                  25                  30
Tyr Met Thr Trp Val Arg Gln Ala Pro Gly Lys Gly Leu Glu Trp Leu
            35                  40                  45
Gly Phe Ile Arg Asn Arg Ala Asn Gly Tyr Thr Thr Glu Tyr Asn Pro
        50                  55                  60
Ser Val Lys Gly Arg Phe Thr Ile Ser Arg Asp Asn Ser Lys Asn Ser
65                  70                  75                  80
Leu Tyr Leu Gln Met Asn Ser Leu Lys Thr Glu Asp Thr Ala Val Tyr
                85                  90                  95
Tyr Cys Ala Arg Val Ser Asn Trp Ala Phe Asp Tyr Trp Gly Gln Gly
            100                 105                 110
Thr Leu Val Thr Val Ser Ser
        115

<210> 45
<211> 119
<212> PRT
<213> Artificial Sequence

<220>
<223> OGD201 72BH

<400> 45
Glu Val Gln Leu Val Glu Ser Gly Gly Gly Leu Val Gln Pro Gly Gly
1               5                   10                  15
Ser Leu Arg Leu Ser Cys Ala Thr Ser Glu Phe Thr Phe Ser Asp Tyr
                20                  25                  30
Tyr Met Thr Trp Val Arg Gln Ala Pro Gly Lys Gly Leu Glu Trp Leu
            35                  40                  45
Gly Phe Ile Arg Asn Lys Ala Asn Gly Tyr Thr Thr Glu Tyr Asn Pro
        50                  55                  60
Ser Val Lys Gly Arg Phe Thr Ile Ser Arg Asp Asn Ser Lys Asn Ser
65                  70                  75                  80
Leu Tyr Leu Gln Met Asn Ser Leu Lys Thr Glu Asp Thr Ala Val Tyr
                85                  90                  95
Tyr Cys Ala Arg Val Ser Asn Trp Ala Phe Asp Tyr Trp Gly Gln Gly
            100                 105                 110
Thr Leu Val Thr Val Ser Ser
        115

<210> 46
<211> 119
<212> PRT
<213> Artificial Sequence

<220>
<223> OGD201 VH49BCDR

<400> 46
Glu Val Gln Leu Val Glu Ser Gly Gly Gly Leu Val Gln Pro Gly Arg
1               5                   10                  15
Ser Leu Arg Leu Ser Cys Thr Ala Ser Glu Phe Thr Phe Thr Asp Tyr
                20                  25                  30
Tyr Met Thr Trp Val Arg Gln Ala Pro Gly Lys Gly Leu Glu Trp Leu
            35                  40                  45
Gly Phe Ile Arg Asn Arg Ala Asn Gly Tyr Thr Thr Glu Tyr Ala Ala
     50                  55                  60
Ser Val Lys Gly Arg Phe Thr Ile Ser Arg Asp Asn Ser Lys Ser Ile
65                  70                  75                  80
Leu Tyr Leu Gln Met Asn Ser Leu Lys Thr Glu Asp Thr Ala Val Tyr
                85                  90                  95
Tyr Cys Ala Arg Val Ser Asn Trp Ala Phe Asp Tyr Trp Gly Gln Gly
            100                 105                 110
Thr Leu Val Thr Val Ser Ser
        115

<210> 47
<211> 119
<212> PRT
<213> Artificial Sequence

<220>
<223> OGD201 VH49BH

<400> 47
Glu Val Gln Leu Val Glu Ser Gly Gly Gly Leu Val Gln Pro Gly Arg
1               5                   10                  15
Ser Leu Arg Leu Ser Cys Thr Thr Ser Glu Phe Thr Phe Thr Asp Tyr
            20                  25                  30
Tyr Met Thr Trp Val Arg Gln Ala Pro Gly Lys Gly Leu Glu Trp Leu
        35                  40                  45
Gly Phe Ile Arg Asn Lys Ala Asn Gly Tyr Thr Thr Glu Tyr Asn Pro
    50                  55                  60
Ser Val Lys Gly Arg Phe Thr Ile Ser Arg Asp Asn Ser Lys Ser Ile
65              70                  75                  80
Leu Tyr Leu Gln Met Asn Ser Leu Lys Thr Glu Asp Thr Ala Val Tyr
            85                  90                  95
Tyr Cys Ala Arg Val Ser Asn Trp Ala Phe Asp Tyr Trp Gly Gln Gly
        100                 105                 110
Thr Leu Val Thr Val Ser Ser
    115

<210> 48
<211> 119
<212> PRT
<213> Artificial Sequence

<220>
<223> OGD201 VH72max

<400> 48
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Asp His
            20                  25                  30
Tyr Met Thr Trp Val Arg Gln Ala Pro Gly Lys Gly Leu Glu Trp Leu
        35                  40                  45
Gly Phe Ile Arg Asn Lys Ala Asn Ser Tyr Thr Thr Glu Tyr Ala Ala
    50                  55                  60
Ser Val Lys Gly Arg Phe Thr Ile Ser Arg Asp Asn Ser Lys Asn Ser
65              70                  75                  80
Leu Tyr Leu Gln Met Asn Ser Leu Lys Thr Glu Asp Thr Ala Val Tyr
            85                  90                  95
Tyr Cys Ala Arg Val Ser Asn Trp Ala Phe Asp Tyr Trp Gly Gln Gly
        100                 105                 110
Thr Leu Val Thr Val Ser Ser
    115

<210> 49
<211> 119
<212> PRT
<213> Artificial Sequence

<220>
<223> OGD201 VH49B

<400> 49
Glu Val Gln Leu Val Glu Ser Gly Gly Gly Leu Val Gln Pro Gly Arg
1               5                   10                  15
Ser Leu Arg Leu Ser Cys Thr Ala Ser Gly Phe Thr Phe Thr Asp Tyr
            20                  25                  30
Tyr Met Thr Trp Val Arg Gln Ala Pro Gly Lys Gly Leu Glu Trp Leu
        35                  40              45
Gly Phe Ile Arg Asn Lys Ala Asn Gly Tyr Thr Thr Glu Tyr Ala Ala
    50                  55              60
Ser Val Lys Gly Arg Phe Thr Ile Ser Arg Asp Asn Ser Lys Ser Ile
65              70                  75              80
Leu Tyr Leu Gln Met Asn Ser Leu Lys Thr Glu Asp Thr Ala Val Tyr
            85                  90                  95
Tyr Cys Ala Arg Val Ser Asn Trp Ala Phe Asp Tyr Trp Gly Gln Gly
            100                 105                 110
Thr Leu Val Thr Val Ser Ser
    115

<210> 50
<211> 119
<212> PRT
<213> Artificial Sequence

<220>
<223> OGD201 VH49Bmax

<400> 50
Glu Val Gln Leu Val Glu Ser Gly Gly Gly Leu Val Gln Pro Gly Arg
1               5                   10                  15
Ser Leu Arg Leu Ser Cys Thr Ala Ser Gly Phe Thr Phe Gly Asp Tyr
            20                  25                  30
Tyr Met Ser Trp Val Arg Gln Ala Pro Gly Lys Gly Leu Glu Trp Leu
        35                  40              45
Gly Phe Ile Arg Asn Lys Ala Asn Gly Gly Thr Thr Glu Tyr Ala Ala
    50                  55              60
Ser Val Lys Gly Arg Phe Thr Ile Ser Arg Asp Asn Ser Lys Ser Ile
65              70                  75              80
Ala Tyr Leu Gln Met Asn Ser Leu Lys Thr Glu Asp Thr Ala Val Tyr
            85                  90                  95
Tyr Cys Thr Arg Val Ser Asn Trp Ala Phe Asp Tyr Trp Gly Gln Gly
            100                 105                 110
Thr Leu Val Thr Val Ser Ser
    115

<210> 51
<211> 119
<212> PRT
<213> Artificial Sequence

<220>
<223> VH72BH AA

<400> 51
Glu Val Gln Leu Val Glu Ser Gly Gly Gly Leu Val Gln Pro Gly Gly
1               5                   10                  15
Ser Leu Arg Leu Ser Cys Ala Thr Ser Glu Phe Thr Phe Ser Asp Tyr
            20                  25              30
Tyr Met Thr Trp Val Arg Gln Ala Pro Gly Lys Gly Leu Glu Trp Leu
        35                  40              45
Gly Phe Ile Arg Asn Lys Ala Asn Gly Tyr Thr Thr Glu Tyr Ala Ala
    50              55              60
Ser Val Lys Gly Arg Phe Thr Ile Ser Arg Asp Asn Ser Lys Asn Ser
65              70              75                  80
Leu Tyr Leu Gln Met Asn Ser Leu Lys Thr Glu Asp Thr Ala Val Tyr
                85              90              95
Tyr Cys Ala Arg Val Ser Asn Trp Ala Phe Asp Tyr Trp Gly Gln Gly
            100             105             110
Thr Leu Val Thr Val Ser Ser
    115